(12) United States Patent
Sutton et al.

(10) Patent No.: US 9,023,847 B2
(45) Date of Patent: May 5, 2015

(54) AZAHETEROCYCLIC COMPOUNDS

(75) Inventors: Amanda E. Sutton, Hingham, MA (US); Nadia Brugger, Cambridge, MA (US); Thomas E. Richardson, Durham, NC (US); Harold George Vandeveer, Indianapolis, IN (US); Bayard R. Huck, Sudbury, MA (US); Ruoxi Lan, Waltham, MA (US); Justin Potnick, Acton, MA (US)

(73) Assignee: Merck Patent GmbH, Darmstadt (DE)

( * ) Notice: Subject to any disclaimer, the term of this patent is extended or adjusted under 35 U.S.C. 154(b) by 139 days.

(21) Appl. No.: 13/388,690

(22) PCT Filed: Jul. 22, 2010

(86) PCT No.: PCT/US2010/042844
§ 371 (c)(1),
(2), (4) Date: Feb. 29, 2012

(87) PCT Pub. No.: WO2011/017009
PCT Pub. Date: Feb. 10, 2011

(65) Prior Publication Data
US 2012/0277228 A1    Nov. 1, 2012

Related U.S. Application Data

(60) Provisional application No. 61/232,179, filed on Aug. 7, 2009.

(51) Int. Cl.
*C07D 471/04* (2006.01)
*C07D 333/02* (2006.01)
*C07D 487/04* (2006.01)

(52) U.S. Cl.
CPC ............ *C07D 471/04* (2013.01); *C07D 333/02* (2013.01); *C07D 487/04* (2013.01)

(58) Field of Classification Search
None
See application file for complete search history.

(56) References Cited

U.S. PATENT DOCUMENTS

2007/0142402 A1   6/2007  Ding et al.

FOREIGN PATENT DOCUMENTS

| WO | 03064397 A1 | 8/2003 |
|---|---|---|
| WO | 2004092154 A1 | 10/2004 |
| WO | 2005033086 A1 | 4/2005 |
| WO | 2005039506 A2 | 5/2005 |
| WO | 2005054237 A1 | 6/2005 |
| WO | 2005056014 A1 | 6/2005 |
| WO | 2005117909 A2 | 12/2005 |
| WO | 2006071819 A1 | 7/2006 |
| WO | 2006120573 A2 | 11/2006 |
| WO | 2006127587 A1 | 11/2006 |
| WO | 2006131835 A2 | 12/2006 |
| WO | 2006136821 A1 | 12/2006 |
| WO | 2008140947 A1 | 11/2008 |

OTHER PUBLICATIONS

Ip et al. "Exploiting P70S6 kinase as a target for ovarian cancer", Expert Opin.Ther.Targets, Jun. 2012, vol. 16, issue 6, pp. 619-630.*
Hanks, S.K. and Hunter, T., FASEB J. (1995), 9:576-596.
Knighton, et al. Science (1991), 253:407-414.
Hiles, et al. Cell (1992), 70:419-429.
Kunz, et al. Cell (1993), 73:585-596.
Garcia-Bustos, et al. EMBO J. (1994), 13:2352-2361.
Barlund, M., et al. Cancer Res. (2000), 60:5340-5346.
Guo-Jun Wu, et al. Cancer Res. (2000), 60:5371-5375.
Banderage U. et al. Bioorganic & Medicinal Chemistry Letters (2009), 19(17):5191-5194.

* cited by examiner

*Primary Examiner* — Jeffrey S Lundgren
*Assistant Examiner* — Stephanie Springer
(74) *Attorney, Agent, or Firm* — EMD Serono Research and Development Institute, Inc.; Thomas W. Brown

(57) ABSTRACT

The invention provides novel substituted azaheterocyclic compounds according to Formula (I), their manufacture and use for the treatment of hyperproliferative diseases, such as cancer.

10 Claims, No Drawings

AZAHETEROCYCLIC COMPOUNDS

FIELD OF THE INVENTION

The invention relates to a series of substituted amino azaheterocyclic compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzyme PI3K is activated by a range of growth and survival factors e.g. EGF, PDGF and through the generation of polyphosphatidylinositols, initiates the activation of the downstream signalling events including the activity of the kinases PDK1 and protein kinase B (PKB) also known as Akt. This is also true in host tissues, e.g. vascular endothelial cells as well as neoplasias. Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/127587, WO 06/131835 and WO 08/140,947.

DESCRIPTION OF THE INVENTION

It is the object of the present invention to provide novel p70S6K inhibitors useful in the treatment of hyperproliferative diseases, especially those related to the hyperactivity of p70S6K as well as diseases modulated by the PI3K signalling pathway, such as cancer in mammals with superior pharmacological properties both with respect to their activities as well as their solubility, metabolic clearance and bioavailability characteristics.

As a result, this invention provides novel, substituted azaheterocyclic compounds and pharmaceutically acceptable salts, solvates or prodrugs thereof, that are p70S6K inhibitors and useful in the treatment of the above mentioned diseases.

The compounds are defined by Formula (I):

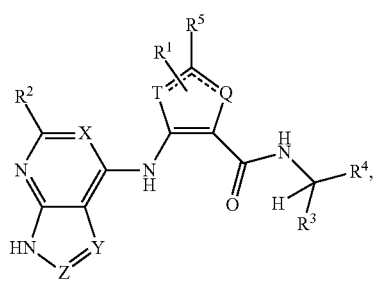

(I)

and pharmaceutically acceptable salts, solvates or prodrugs thereof, wherein:

X, Y, Z each, independently of one another, are N or $CR^2$, with the proviso that if Z is N, Y is $CR^2$, and if Y is N, Z is $CR^2$, T, Q are S, O or $CR^5$, with the proviso that if T is S or O, Q is $CR^5$, and if Q is S or O, T is $CR^5$, ----- denotes the presence or absence of a bond, with the proviso that one of the two dashed lines is always a bond, whereas the other one is always absent, $R^1$, $R^2$, $R^5$ each, independently of one another, are H, A, Hal, OH, SH, CN, $NH_2$, $NO_2$, $R^3$ is H or A, $R^4$ is A, Ar or A-Ar, or $R^3$ and $R^4$ together with the C atom to which they are attached, may form Ar, or cyclic A which may be unsubstituted or substituted by COO(LA) or CONH(LA), Ar is a mono- or bicyclic aromatic homo- or heterocycle having 1 to 4 N, O and/or S atoms and 5 to 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, CONH(LAr), $CONA_2$, NHCOA, NHCO(LAr), NHCONHA, $NHCONH_2$, $NHSO_2A$, CHO, COA, $SO_2NH_2$, $SO_2A$ and/or $SO_2Hal$, A is unbranched or branched, linear or cyclic alkyl having 1, 2, 3, 4, 5, 6, 7 or 8 C atoms, in which one or two $CH_2$ groups may be replaced by an O or S atom and/or by an NH, N(LA), $SO_2$, CONH, NHCO or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$, $N_3$, $NO_2$ or CN, LA is unbranched or branched, linear alkyl having 1, 2, 3 or 4 C atoms, LAr is a monocyclic aromatic homo- or heterocycle having 1 or 2 N, O and/or S atoms and 5 to 7 skeleton atoms, which may be unsubstituted or mono-, di- or trisubstituted by Hal, LA, OH, O(LA), $NH_2$ or NH(LA), Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

"A" further denotes alkyl as defined above, in which one or two $CH_2$ groups may be replaced by O or S atoms and/or by NH, NA, CONH, NHCO or —CH=CH— groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy.

In other examples of "A", one or two $CH_3$ groups is replaced by OH, SH, $NH_2$, N(LA)H, $N(LA)_2$, $N_3$, $NO_2$ or CN, such as, for example, N,N'-dimethylaminoalkyl, 2-aminoethyl, 3-aminopropyl, 4-aminobutyl, 5-aminopentyl, 3-aminomethylcyclobutyl or cyanoalkyl.

"A" may also be cyclic, wherein the cyclic moiety can be substituted by, or incorporated in an otherwise non-cyclic structure. Examples for cyclic "A" include 2- or 3-furyl, 2,3-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 2-, 3-, 5- or 6-piperidin-1 or 4-yl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoro-methylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl, indan-1-, 2-, 4- or 5-yl, 1,2,3,4-tetrahydro-naphthalenyl, tetrahydrofuran-2- or 3-yl or 2,3-dihydro-2-oxofuranyl, each of which is unsubstituted or may be mono-, di- or trisubstituted, for example, by carbonyl oxygen, F, Cl, Br, methyl, ethyl, propyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

"LA" denotes unbranched or branched, linear alkyl having 1, 2, 3 or 4 C atoms, i.e. methyl, ethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methyl-amino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl) phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methyl-sulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxy-phenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-tri-chlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6, -or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

"LAr" denotes a subsection of "Ar", wherein "Ar" is limited to a monocyclic aromatic homo- or heterocycle which may be unsubstituted or mono-, di- or trisubstituted. Preferred examples of "LAr" include 4-fluorophenyl or 2-chloropyridin-4-yl.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

A preferred group of compounds of Formula (I) conforms to Formulae (II), (III), (IV) or (V),

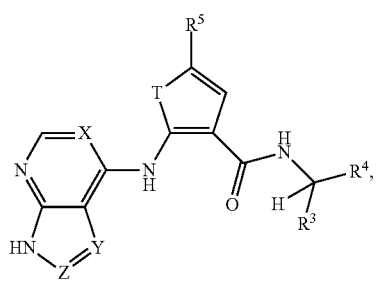
(II)

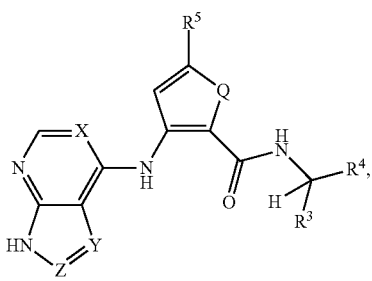
(III)

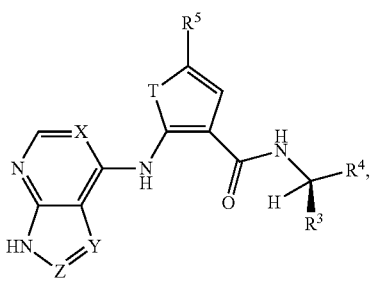
(IV)

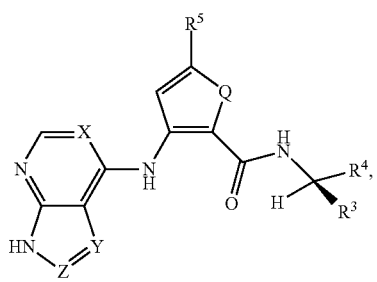
(V)

in which T and Q are S or O, and the remaining substituents have the meaning indicated for Formula (I) above.

Even more preferred are compounds of Subformulae A, B, C, D, E, F, G, H, J, K, L, M, N, O, P, Q, R, S, T, U, V and W of Formulae (I), (II), (III), (IV) and (V), and pharmaceutically acceptable salts, solvates or prodrugs thereof, wherein
in Subformula A
T, Q are S,
$R^5$ is H or methyl,
and the remaining residues have the meaning as indicated for Formula (I) above,
in Subformula B
T, Q are O,
$R^5$ is H or methyl,
and the remaining residues have the meaning as indicated for Formula (I) above,
in Subformula C
X, Y, Z are CH,
and the remaining residues have the meaning as indicated for Formula (I) above,
in Subformula D
X, Y, Z are CH,
T, Q are S,
$R^5$ is H or methyl,
and the remaining residues have the meaning as indicated for Formula (I) above,
in Subformula E
Y, Z are CH,
X is N,
T, Q are S,
$R^5$ is H or methyl,
and the remaining residues have the meaning as indicated for Formula (I) above,
in Subformula F
X, Y, Z are CH,
T, Q are S,
$R^5$ is H or methyl,
$R^3$ is H, hydroxymethyl, aminomethyl, azidomethyl or cyanomethyl,
and the remaining residues have the meaning as indicated for Formula (I) above,
in Subformula G
X, Y, Z are CH,
T, Q are S,
$R^5$ is H or methyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl,
and the remaining residues have the meaning as indicated for Formula (I) above,
in Subformula H
Y, Z are CH,
X is N,
$R^5$ is H or methyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula J Y, Z are CH,
X is N,
T, Q are S,
$R^5$ is H or methyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula K Y, Z are CH,
X is N,
T, Q are O,
$R^5$ is H or methyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula L X, Y, Z are CH,
T, Q are S,
$R^5$ is H or methyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula M X, Y, Z are CH,
T, Q are S,
$R^5$ is H,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula N X, Y, Z are CH,
T, Q are S,
$R^5$ is H or methyl,
$R^3$ is H, hydroxymethyl, aminomethyl, azidomethyl or cyanomethyl,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula O Y, Z are CH, X is N, $R^5$ is H or methyl, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula P Y, Z are CH, X is N, T, Q are S, $R^5$ is H or methyl, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula Q Y, Z are CH, X is N, T, Q are O, $R^5$ is H or methyl, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula R X, Y, Z are CH, T, Q are S, $R^5$ is H or methyl, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula S X, Y, Z are CH, T, Q are S, $R^5$ is H, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula T X, Y, Z are CH, T, Q are S, $R^5$ is H, $R^3$ is hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F, and the remaining residues have the meaning as indicated for Formula (I) above, in Subformula U X, Y, Z are CH, T, Q are S, $R^5$ is H, $R^3$ is H, $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, and the remaining residues have the meaning as indicated for Formula (I) above, in Subformula V X, Y, Z are CH, T, Q are S, $R^5$ is H, $R^3$ and $R^4$ together with the C atom to which they are attached, form piperidinyl, phenyl, pyrrolidinyl, tetrahydrofuranyl, each of which may be unsubstituted or, independently of one another, mono-, di- or trisubstituted by methyl, methoxy, $CF_3$, $OCF_3$, amino, Cl or F, and the remaining residues have the meaning as indicated for Formula (I) above, in Subformula W X, Z are CH, Y is $CR^2$, $R^2$ is methyl, T, Q are S, $R^5$ is H, $R^3$ is H, and the remaining residues have the meaning as indicated for Formula (I) above, Especially preferred compounds according to Formula (I) and/or Formula (II) include the compounds shown in the examples section below as well as those compounds listed in Table 1 below, or the pharmaceutically acceptable salts, solvates or prodrugs each thereof.

For the p70S6K inhibition the following classification is used:

$IC_{50} < 0.1\ \mu M$ "+++"

$0.1\ \mu m \leq IC_{50} < 1.0\ \mu M$ "++"

$1.0\ \mu m \leq IC_{50} < 10\ \mu M$ "+"

| No. | Structure | Chemical Name | p70S6K inhibition ($IC_{50}$) |
|---|---|---|---|
| 141 | 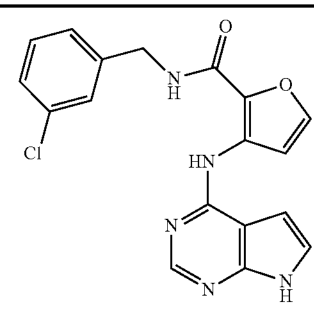 | 3-(7H-Pyrrolo[2,3-d]pyrimidin-4-ylamino)-furan-2-carboxylic acid 3-chloro-benzylamide | +++ |
| 142 | 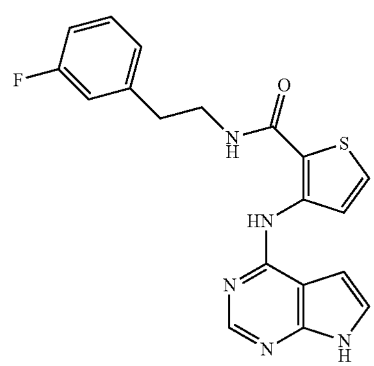 [SMILES: O=C(NCCc1cccc(F)c1)c1sccc1Nc1ncnc2[nH]ccc12] | 3-(7H-Pyrrolo[2,3-d]pyrimidin-4-ylamino)-thiophene-2-carboxylic acid [2-(3-fluoro-phenyl)-ethyl]-amide | +++ |

-continued

| No. | Structure | Chemical Name | p70S6K inhibition (IC$_{50}$) |
|---|---|---|---|
| 143 | 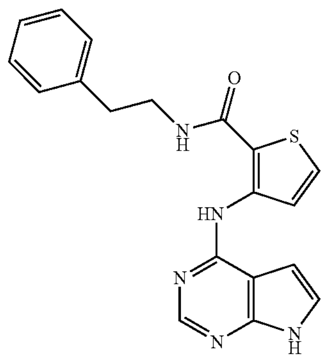 [SMILES: O=C(NCCc1ccccc1)c1sccc1Nc1ncnc2[nH]ccc12] | 3-(7H-Pyrrolo[2,3-d]pyrimidin-4-ylamino)-thiophene-2-carboxylic acid phenethyl-amide | +++ |
| 144 | 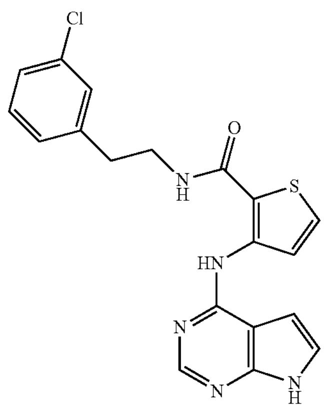 [SMILES: O=C(NCCc1cccc(Cl)c1)c1sccc1Nc1ncnc2[nH]ccc12] | 3-(7H-Pyrrolo[2,3-d]pyrimidin-4-ylamino)-thiophene-2-carboxylic acid [2-(3-chloro-phenyl)-ethyl]-amide | +++ |
| 145 | 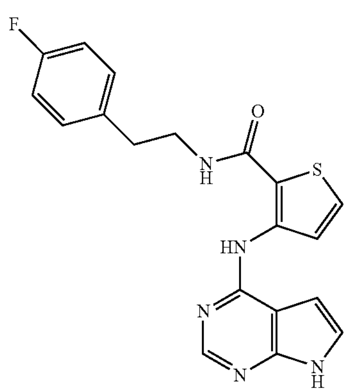 [SMILES: O=C(NCCc1ccc(F)cc1)c1sccc1Nc1ncnc2[nH]ccc12] | 3-(7H-Pyrrolo[2,3-d]pyrimidin-4-ylamino)-thiophene-2-carboxylic acid [2-(4-fluoro-phenyl)-ethyl]-amide | +++ |
| 146 | 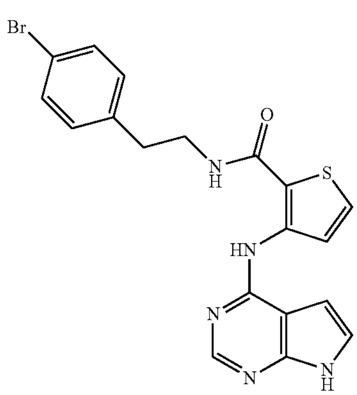 [SMILES: O=C(NCCc1ccc(Br)cc1)c1sccc1Nc1ncnc2[nH]ccc12] | 3-(7H-Pyrrolo[2,3-d]pyrimidin-4-ylamino)-thiophene-2-carboxylic acid [2-(4-bromo-phenyl)-ethyl]-amide | +++ |

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

Abbreviations

| Designation | |
|---|---|
| ATP | Adenosine triphosphate |
| B | Broad peak |
| BOC | Butyloxycarbonyl |
| d | Doublet |
| Dba | Tris(dibenzylideneacetone) |
| Dd | Doublet of doublets |
| DMF | N,N-Dimethylformamide |
| DMSO | dimethylsulfoxide |
| DTT | dithiothreitol |

-continued

| Designation | |
|---|---|
| EDTA | Ethylenediaminetetraacetic acid |
| ESI | Electrospray ionization |
| Et | ethyl |
| h | hour |
| HATU | 2-(7-Aza-1H-benzotriazole-1-yl)-1,1,3,3-tetramethyluronium hexafluorophosphate |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMR | Nuclear Magnetic Resonance |
| psi | Pounds per square inch |
| q | Quartette (or quartet) |
| Rf | Retention factor |
| rt | Room temperature |
| s | Singlet |
| Tert | Tertiary |
| TFA | Trifluoroacetic acid |
| THAB | Tetrahexylammonium bromide |
| THF | Tetrahydrofuran |
| Tips | Triisopropylsilyl |
| UV | Ultraviolet |
| VIS | Visible |
| XPhos | 2-Dicyclohexylphosphino-2',4',6'-triisopropylbiphenyl |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formulae (I), (II), Subformulae A-U as well as those disclosed in Table 1, according to the hereinafter described schemes and working examples.

General Synthetic Procedures

All temperatures are given in degrees Centigrade. Reagents were purchased from commercial sources or prepared following literature procedures.

Scheme 1
General Scheme for the thiophene carboxylic acid formation

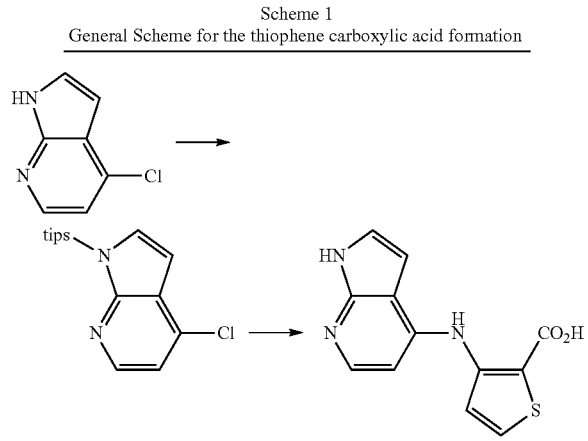

After protection of the azaindole NH group with "tips", the intermediate chloride is reacted with thiophene amino acid to yield the thiophene carboxylic acid.

Experimentals for Scheme 1

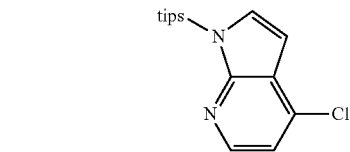

4-Chloro-1-trisopropylsilyl-1H-pyrrolo[2,3-b]pyridine

To a 1 L flask was added 4-chloroazaindole (23 g, 147 mmol) and THF (400 mL), cooled to 0° C. and NaH (60%, 18 g, 442 mmol) was added portion wise over 10 min. The temperature was allowed to warm to room temperature for 30 min then was re-cooled to 0° C. After addition of triisopropylsilyl chloride (31 mL, 147 mmol) the reaction was heated to 50° C. for 18 h. The reaction was cooled to room temperature and quenched by a slow addition of water. The aqueous layer was extracted with ethyl acetate (3×), dried over $Na_2SO_4$ and concentrated in vacuo. The material was purified ISCO companion (heptane to 50% ethyl acetate/heptane) to afford 30 g (66%) of the desired material. LCMS (ESI) 309 (M+H) $^1$H NMR (400 MHz, DMSO-$d_6$) δ ppm 8.17 (1H, d, J=5.27 Hz) 7.56 (1H, d, J=3.51 Hz) 7.20 (1H, d, J=5.08 Hz) 6.65 (1H, d, J=3.51 Hz) 1.78-1.90 (3H, m) 1.00-1.08 (18H, m)

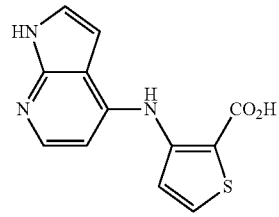 [SMILES: O=C(O)c1sccc1Nc1ccnc2[nH]ccc12]

3-(1H-Pyrrolo[2,3-b]pyridin-4-ylamino)-thiophene-2-carboxylic acid

A solution of the 4-Chloro-1-triisopropylsilyl-1H-pyrrolo[2,3-b]pyridine (20 g, 65 mmol), potassium carbonate (2.0 g, 143 mmol), XPhos (3.1 g, 6.5 mmol), methyl 3-aminothiophene-2-carboxylate (12.3 g, 78 mmol) in t-butanol (108 mL) was degassed with nitrogen for 30 min. $Pd_2(dba)_3$ (3.0 g, 3.3 mmol) was added to the reaction mixture and the resulting solution was evacuated and refilled with nitrogen 3× and then heated to 100° C. for 2 days. The reaction was filtered through a pad of celite, washed with ethyl acetate, concentrated in vacuo and carried on crude to the hydrolysis step.

The above crude material was dissolved in THF/MeOH/$H_2O$ (210/140/70 mL). Lithium hydroxide (14 g, 325 mmol) was added to the solution and heated to 85° C. overnight. The reaction was cooled to room temperature and filtered through a pad of celite. The pad of celite was washed with water and methanol. The filtrate was diluted with water (250 mL) and concentrated to remove organic solvents. The solution was filtered through a pad of celite and the basic aqueous solution was acidified to pH=5 to afford a white precipitate that was collected, washed with water and heptanes and dried in a vacuum oven for several day to afford 3-(1H-Pyrrolo[2,3-b]pyridin-4-ylamino)-thiophene-2-carboxylic acid (17.3 g, 99% for the two steps). LCMS (ESI) 260 (M+H) $^1$H NMR (400 MHz, DMSO-$d_6$) δ ppm 11.59 (1H, br. s.) 9.65 (1H, br. s.) 8.05 (1H, d, J=5.47 Hz) 7.86 (1H, d, J=5.47 Hz) 7.49 (8H, d, J=5.47 Hz) 7.33 (1H, dd, J=3.32, 2.54 Hz) 6.93 (1H, d, J=5.47 Hz) 6.42 (1H, dd, J=3.51, 1.76 Hz)

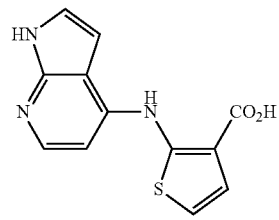 [SMILES: O=C(O)c1ccsc1Nc1ccnc2[nH]ccc12]

2-(1H-Pyrrolo[2,3-b]pyridin-4-ylamino)-thiophene-3-carboxylic acid

This compound was prepared in an analogous manner as 3-(1H-Pyrrolo[2,3-b]pyridin-4-ylamino)-thiophene-2-carboxylic acid using methyl 2-aminothiophene-3-carboxylate instead of methyl 3-aminothiophene-2-carboxylate.). LCMS (ESI) 260 (M+H) $^1$H NMR (400 MHz, DMSO-$d_6$) δ ppm 11.88 (1H, br. s.) 10.77 (1H, s) 8.16 (1H, d, J=5.66 Hz) 7.41 (1H, dd, J=3.22, 1.85 Hz) 7.23 (1H, d, J=5.86 Hz) 7.01 (1H, d, J=5.86 Hz) 6.94 (1H, d, J=5.66 Hz) 6.47 (1H, d, J=2.73 Hz)

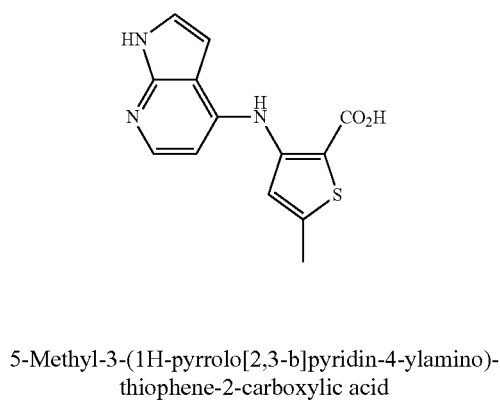

5-Methyl-3-(1H-pyrrolo[2,3-b]pyridin-4-ylamino)-thiophene-2-carboxylic acid

This compound was prepared in an analogous manner as 3-(1H-Pyrrolo[2,3-b]pyridin-4-ylamino)-thiophene-2-carboxylic acid using methyl 3-amino-5-methylthiophene-2-carboxylate instead of methyl 3-aminothiophene-2-carboxylate. LCMS (ESI) 274 (M+H) $^1$H NMR (400 MHz, DMSO-$d_6$) δ ppm 11.60 (1H, br. s.) 9.66 (1H, s) 8.06 (1H, d, J=4.49 Hz) 7.30-7.38 (1H, m) 6.95 (1H, d, J=5.47 Hz) 6.42 (1H, d, J=1.76 Hz) 2.50 (3H, s)

General Scheme for amide formation-Scheme 2

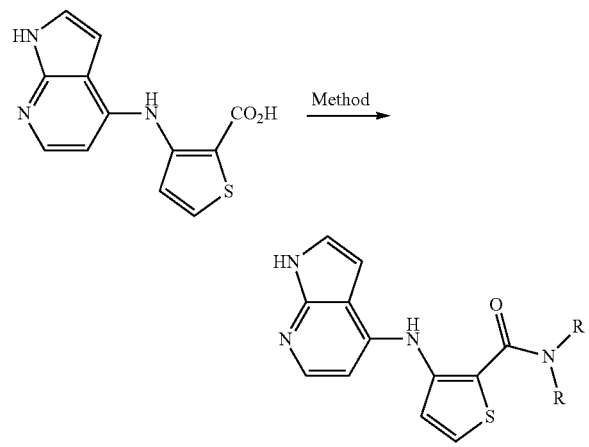

For the amide formation one the following methods can be used:

1. Acid chloride formation, followed by amine addition

An acid chloride is formed as an intermediate, which is quenched with an amine to form the desired amide 2. HATU carboxylic acid activation, followed by amine addition:

HATU is an amide bond coupling agent that allows direct amide formation from a carboxylic acid starting material, via a HATU-activated carboxylic acid intermediate.

3. AlMe$_3$ carboxylic acid activation, followed by amine addition:

AlMe$_3$ is a reagent used for direct amide formation from a carboxylic acid, via a Al-Me-carboxylic acid intermediate.

Since AlMe$_3$ is a harsh reagent, methods 1 and 2 are preferred.

Scheme 3
General Scheme for Reductive Amination

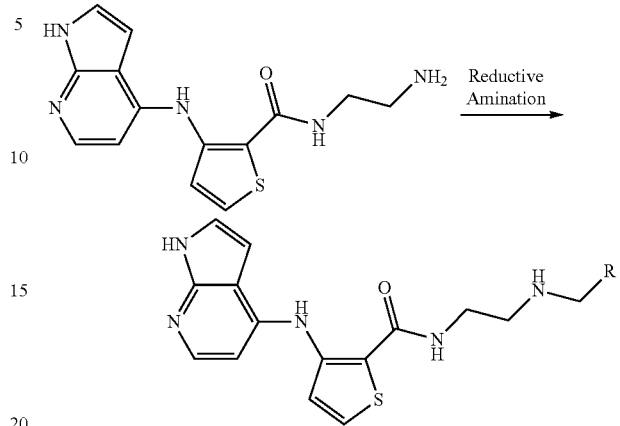

If desired, another substituted alkyl group may be introduced to the amine via reductive amination, by reacting the amine with an aldehyde (or ketone), and then reducing the resulting imine to the amine.

Analytical Methodology

LC/MS was Performed Using the Following Two Methods:

Method A (Rapid LC):

A Shimadzu Shim-pack XR-ODS, 3.0×30 mm, 2.2 m, was used at a temperature of 50° C. and at a flow rate of 1.5 mL/min, 2 μL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B).

Method B (Polar Stop-Gap):

An Agilent Zorbax Bonus RP, 2.1×50 mm, 3.5 m, was used at a temperature of 50° C. and at a flow rate of 0.8 mL/min, 2 μL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Preparative HPLC was performed using a system controlled by Chromeleon software and consisting of two Varian PrepStar Model 218 Pumps, a Varian ProStar Model 320 UV/Vis detector, a SEDEX 55 ELSD detector, and a Gilson 215 liquid handler. Typical HPLC mobile phases consist of water and methanol. The standard column is a Varian Dynamax 21.4 mm diameter Microsorb Guard-8 C18 column.

Routine purifications were performed using the Teledyne Isco CombiFlash® Companion® System using RediSep Rf silica gel columns. Typical mobile phase using one or two solvent isocratic, linear and/or step gradients are described within the experimental section. Peaks were detected using photodiode array absorbance detector (200-360 nm).

NMR Spectra were acquired on a Varian $^{Unity}$Inova 400 MHz NMR spectrometer equipped with an Automation Triple Broadband (ATB) probe. The ATB probe was simultaneously tuned to $^1$H, $^{13}$F and $^{13}$C. For typical $^1$H NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to 1 second. Spectra were collected at 25° C. 1H NMR Spectra are typically processed with 0.2 Hz line broadening and zero-filling to 131072 points prior to Fourier transformation.

EXAMPLES

The examples presented below are intended to illustrate particular embodiments of the invention, and are not intended to limit the scope of the specification or the claims in any way.

Chemical Synthesis 1. 3-(1H-Pyrrolo[2,3-b]pyridin-4-ylamino)-thiophene-2-carboxylic acid amide

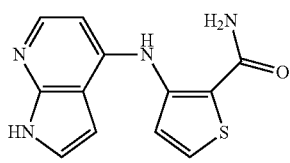 [SMILES: NC(=O)c1sccc1Nc1ccnc2[nH]ccc12]

4-Chloro-1H-pyrrolo-(2,3,b)-pyridine (150 mg, 0.90 mmol) and 3-aminothiophene-2-carboxamide (167 mg, 1.2 mmol) were dissolved in a ethanol:water solution (4:2 mL) and charged with 1 drop HCl (conc.), where it was heated to 100° C. for 48 h. The reaction mixture was poured into a NaHCO$_3$/EtOAc mixture where the organic layer was collected and the aqueous layer was extracted with EtOAc (×2). The organic layers were combined, dried over sodium sulfate, filtered and concentrated in vacuo. The residue was purified by ISCO Companion (silica, (10% methanol, methylene chloride, 0.5% ammonium hydroxide) to afford 3-(1H-Pyrrolo[2,3-b]pyridin-4-ylamino)-thiophene-2-carboxylic acid amide (75 mg, 32%) LCMS (ESI) 259 (M+H) $^1$H NMR (400 MHz, DMSO-d6) δ ppm 12.45 (1H, br. s.) 10.71 (1H, s) 8.09 (1H, d, J=7.03 Hz) 7.88 (1H, d, J=5.27 Hz) 7.61 (1H, br. s.) 7.43 (1H, dd, J=3.42, 2.44 Hz) 7.36 (1H, d, J=5.27 Hz) 6.77 (1H, d, J=6.83 Hz) 6.66 (1H, d, J=1.56 Hz)

2. 4-(1H-Pyrrolo[2,3-b]pyridin-4-ylamino)-thiophene-3-carboxylic acid methyl ester

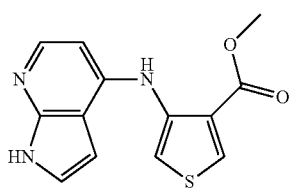 [SMILES: COC(=O)c1cscc1Nc1ccnc2[nH]ccc12]

4-Chloro-1H-pyrrolo-(2,3,b)-pyridine (250 mg, 1.6 mmol) and methyl-4-aminothiophene-3-carboxylate (632 mg, 3.3 mmol) were dissolved in a methanol:water solution (4:2 mL) and charged with 1 drop HCl (conc.), where it was heated to 100° C. for 16 hours. The reaction mixture was poured into a NaHCO$_3$/EtOAc mixture where the organic layer was collected and the aqueous layer was extracted with EtOAc (×2). The organic layers were combined, dried over sodium sulfate, filtered and concentrated in vacuo. The residue was purified by ISCO Companion (silica, (10% methanol, methylene chloride, 0.5% ammonium hydroxide) to afford 4-(1H-Pyrrolo[2,3-b]pyridin-4-ylamino)-thiophene-3-carboxylic acid methyl ester (32 mg, 7%) LCMS (ESI) 274 (M+H) 1H NMR (400 MHz, DMSO-d6) δ ppm 11.52 (1H, br. s.) 9.20 (1H, s) 8.45 (1H, d, J=3.32 Hz) 8.04 (1H, d, J=5.47 Hz) 7.39 (1H, d, J=3.32 Hz) 7.30 (1H, dd, J=3.32, 2.34 Hz) 6.95 (1H, d, J=5.47 Hz) 6.45 (1H, dd, J=3.51, 1.76 Hz) 3.87 (3H, s)

3. 3-(1H-Pyrrolo[2,3-b]pyridin-4-ylamino)-thiophene-2-carboxylic acid (tetrahydro-furan-2-ylmethyl)-amide

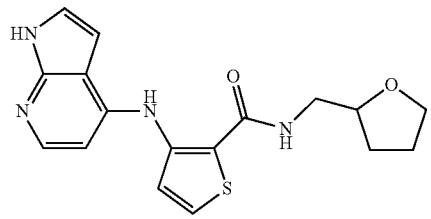 [SMILES: O=C(NCC1CCCO1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-(tetrahydrofuran-2-yl)methaneamine instead of 1-BOC-3-aminopyrrolidine. LCMS (ESI) 343 (M+H) $^1$H NMR (400 MHz, ACETONITRILE-d$_3$) δ ppm 10.54 (1H, s) 8.01 (1H, d, J=7.03 Hz) 7.67 (1H, d, J=5.27 Hz) 7.42 (1H, d, J=5.27 Hz) 7.39 (1H, dd, J=3.42, 1.85 Hz) 6.97 (1H, d, J=6.83 Hz) 6.66 (1H, dd, J=3.42, 1.66 Hz) 3.95 (1H, qd, J=6.80, 4.59 Hz) 3.72 (1H, dt, J=8.15, 6.56 Hz) 3.57-3.66 (1H, m) 3.29-3.48 (2H, m) 1.87-1.97 (3H, m) 1.77-1.86 (2H, m) 1.48-1.60 (1H, m)

IC$_{50}$ (p70S6K) "++"

4. Pyrrolidin-1-yl-[3-(1H-pyrrolo[2,3-b]pyridin-4-ylamino)-thiophen-2-yl]-methanone

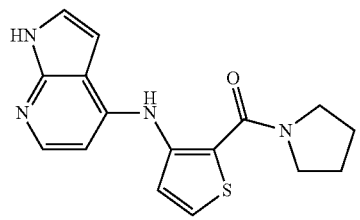 [SMILES: O=C(c1sccc1Nc1ccnc2[nH]ccc12)N1CCCC1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using pyrrolidine instead of 1-BOC-3-aminopyrrolidine. LCMS (ESI) 313 (M+H) $^1$H NMR (400 MHz, DMSO-d6) δ ppm 12.40 (1H, br. s.) 10.62 (1H, s) 8.07 (1H, d, J=6.83 Hz) 7.88 (1H, d, J=5.27 Hz) 7.39 (1H, d, J=3.51 Hz) 7.29 (1H, d, J=5.47 Hz) 6.72 (1H, d, J=3.32 Hz) 6.70 (1H, d, J=6.64 Hz) 3.42 (1H, br. s.) 2.47 (4H, dt, J=3.66, 1.78 Hz) 1.75 (4H, br. s.)

IC$_{50}$ (p70S6K) "++"

5. 3-{[3-(1H-Pyrrolo[2,3-b]pyridin-4-ylamino)-thiophene-2-carbonyl]-amino}-pyrrolidine-1-carboxylic acid tert-butyl ester

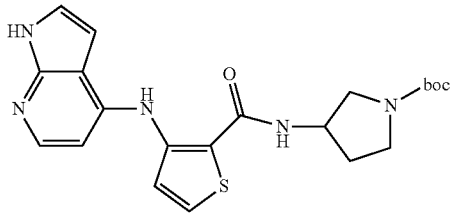

To a solution of 3-(1H-Pyrrolo[2,3-b]pyridin-4-ylamino)-thiophene-2-carboxylic acid (100 mg, 0.39 mmol), diisopropylethylamine (0.1 mL, 0.54 mmol), 1-BOC-3-aminopyrrolidine (143 mg, 0.77 mmol) in dimethylformamide (2 mL) was added HATU (176 mg, 0.463 mmol). The solution stirred at room temperature for 18 h then diluted with ethyl acetate and washed with aqueous 1% lithium chloride. The organic layer was dried, concentrated in vacuo and purified by ISCO Companion to provide 3-{[3-(1H-Pyrrolo[2,3-b]pyridin-4-ylamino)-thiophene-2-carbonyl]-amino}-pyrrolidine-1-carboxylic acid tert-butyl ester (161 mg, 95%). LCMS (ESI) 428 (M+H) 1H NMR (400 MHz, DMSO-d6) δ ppm 11.55 (1H, br. s.) 10.24 (1H, s) 8.20 (1H, d, J=6.83 Hz) 8.02 (1H, d, J=5.47 Hz) 7.81 (1H, d, J=5.47 Hz) 7.47 (1H, d, J=5.47 Hz) 7.31 (1H, dd, J=3.32, 2.54 Hz) 6.80 (1H, d, J=5.47 Hz) 6.44 (1H, dd, J=3.42, 1.85 Hz) 4.35-4.58 (1H, m) 3.47-3.65 (1H, m) 3.33-3.44 (1H, m) 3.26 (1H, t, J=9.08 Hz) 3.09-3.21 (1H, m) 1.99-2.14 (1H, m) 1.81-1.95 (1H, m) 1.39 (9H, s).

IC$_{50}$ (p70S6K) "++"

6. 3-(1H-Pyrrolo[2,3-b]pyridin-4-ylamino)-thiophene-2-carboxylic acid pyrrolidin-3-ylamide

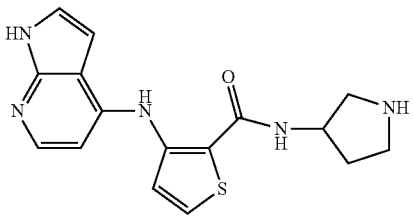 [SMILES: O=C(NC1CCNC1)c1sccc1Nc1ccnc2[nH]ccc12]

A solution of 3-{[3-(1H-Pyrrolo[2,3-b]pyridin-4-ylamino)-thiophene-2-carbonyl]-amino}-pyrrolidine-1-carboxylic acid tert-butyl ester (50 mg, 0.12 mmol) in methylene chloride (1.0 mL) was added trifluoromethyl acetic acid (1.0 mL). After 1H the solution was concentrated in vacuo, triturated with diethylether to afford 3-(1H-Pyrrolo[2,3-b]pyridin-4-ylamino)-thiophene-2-carboxylic acid pyrrolidin-3-ylamide (48 mg, 99%). LCMS (ESI) 328 (M+H) 1H NMR (400 MHz, DMSO-d6) δ ppm 11.54 (1H, br. s.) 10.25 (1H, s) 8.08 (1H, d, J=6.83 Hz) 8.02 (1H, d, J=5.47 Hz) 7.81 (1H, d, J=5.27 Hz) 7.48 (1H, d, J=5.47 Hz) 7.32 (1H, d, J=3.51 Hz) 6.81 (1H, d, J=5.47 Hz) 6.44 (1H, d, J=3.51 Hz) 4.32-4.51 (1H, m) 3.14 (1H, dd, J=11.62, 6.74 Hz) 3.02-3.11 (1H, m) 2.89-2.98 (1H, m) 2.86 (1H, dd, J=11.71, 5.08 Hz) 1.97-2.15 (1H, m) 1.68-1.84 (1H, m)

IC$_{50}$ (p70S6K) "+++"

7. 3-(1H-Pyrrolo[2,3-b]pyridin-4-ylamino)-thiophene-2-carboxylic acid (pyridin-2-ylmethyl)-amide

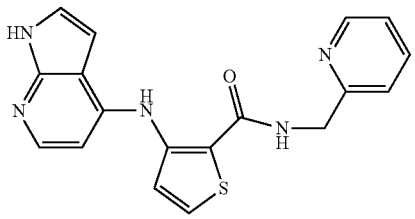 [SMILES: O=C(NCc1ccccn1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(aminomethyl)pyridine instead of 1-BOC-3-aminopyrrolidine. LCMS (ESI) 350 (M+H) 1H NMR (400 MHz, DMSO-d6) δ ppm 11.55 (1H, br. s.) 10.25 (1H, s) 8.75 (1H, t, J=5.95 Hz) 8.43-8.49 (1H, m) 8.02 (1H, d, J=5.47 Hz) 7.83 (1H, d, J=5.27 Hz) 7.69-7.77 (1H, m) 7.49 (1H, d, J=5.47 Hz) 7.28-7.34 (2H, m) 7.21-7.27 (1H, m) 6.82 (1H, d, J=5.47 Hz) 6.41 (1H, dd, J=3.51, 1.76 Hz) 4.55 (2H, d, J=6.05 Hz)

IC$_{50}$ (p70S6K) "++"

8. 3-(1H-Pyrrolo[2,3-b]pyridin-4-ylamino)-thiophene-2-carboxylic acid (pyridin-3-ylmethyl)-amide

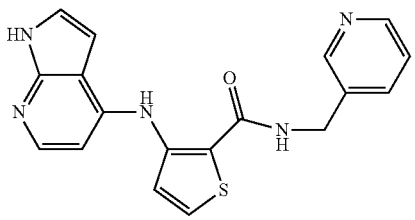 [SMILES: O=C(NCc1cccnc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-(aminomethyl)pyridine instead of 1-BOC-3-aminopyrrolidine. 1H NMR (400 MHz, DMSO-d6) δ ppm 11.54 (1H, br. s.) 10.28 (1H, s) 8.73 (1H, t, J=6.05 Hz) 8.55 (1H, d, J=1.76 Hz) 8.45 (1H, dd, J=4.78, 1.66 Hz) 8.02 (1H, d, J=5.47 Hz) 7.81 (1H, d, J=5.47 Hz) 7.67-7.74 (1H, m) 7.50 (1H, d, J=5.47 Hz) 7.28-7.38 (2H, m) 6.84 (1H, d, J=5.47 Hz) 6.42 (1H, dd, J=3.42, 1.85 Hz) 4.48 (2H, d, J=6.05 Hz)

IC$_{50}$ (p70S6K) "++"

9. 3-(1H-Pyrrolo[2,3-b]pyridin-4-ylamino)-thiophene-2-carboxylic acid piperidin-3-ylamide

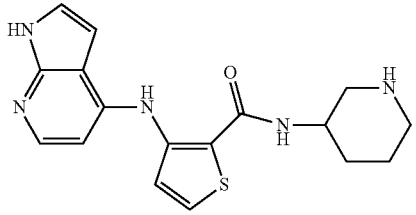 [SMILES: O=C(NC1CCCNC1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl 3-aminopiperidine-1-carboxylate instead of 1-BOC-3-aminopyrrolidine.

To a solution of N-Boc (664 mg, 1.5 mmol) in methylene chloride (2.0 mL) was added trifluoroacetic acid (2.0 mL). The reaction stirred at room temperature for 4 h then concentrated to dryness in vacuo. The residue was re-dissolved in ethyl acetate then washed with 1N NaOH. The organic layer was dried with sodium sulfate, filtered then concentrated. The residue was purified by ISCO silica flash column (9:1:1 methylene chloride:methanol:ammonium hydroxide) to afford 500 mg (98%). LCMS (ESI) 342 (M+H) 1H NMR (400 MHz, DMSO-d6) δ ppm 11.53 (1H, s) 10.21 (1H, s) 8.01 (1H, d, J=5.27 Hz) 7.88 (1H, d, J=7.81 Hz) 7.80 (1H, d, J=5.47 Hz) 7.46 (1H, d, J=5.27 Hz) 7.31 (1H, d, J=3.51 Hz) 6.78 (1H, d, J=5.27 Hz) 6.43 (1H, d, J=3.51 Hz) 3.88-4.00 (1H, m, J=3.71 Hz) 2.99-3.07 (1H, m, J=3.90 Hz) 2.85-2.93 (1H, m, J=12.10 Hz) 2.46-2.57 (2H, m) 1.76-1.85 (1H, m) 1.60-1.69 (1H, m) 1.39-1.56 (2H, m)

IC$_{50}$ (p70S6K) "++"

10. 3-(1H-Pyrrolo[2,3-b]pyridin-4-ylamino)-thiophene-2-carboxylic acid (2-hydroxy-1-methyl-ethyl)-amide

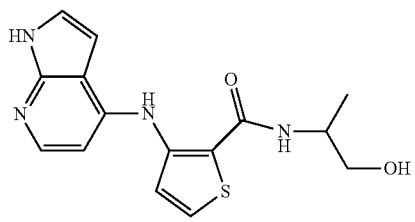 [SMILES: CC(CO)NC(=O)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-amino-2-propanol instead of 1-BOC-3-aminopyrrolidine. LCMS (ESI) 317 (M+H) 1H NMR (400 MHz, DMSO-d6) δ ppm 11.52 (1H, s) 10.29 (1H, s) 8.01 (1H, d, J=5.47 Hz) 7.78 (1H, d, J=5.27 Hz) 7.69 (1H, d, J=8.00 Hz) 7.46 (1H, d, J=5.27 Hz) 7.27-7.33 (1H, m) 6.79 (1H, d, J=5.47 Hz) 6.43 (1H, dd, J=3.51, 1.95 Hz) 4.71 (1H, t, J=5.76 Hz) 3.97-4.09 (1H, m) 3.27-3.48 (2H, m) 1.09 (3H, d, J=6.64 Hz)

IC$_{50}$ (p70S6K) "++"

11. 3-(1H-Pyrrolo[2,3-b]pyridin-4-ylamino)-thiophene-2-carboxylic acid (2-hydroxy-propyl)-amide

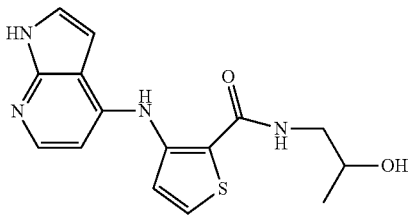 [SMILES: CC(O)CNC(=O)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-amino-2-propanol instead of 1-BOC-3-aminopyrrolidine. LCMS (ESI) 317 (M+H) 1H NMR (400 MHz, DMSO-d6) δ ppm 11.49 (1H, s) 10.22 (1H, s) 7.99 (1H, d, J=5.47 Hz) 7.94-7.98 (1H, m) 7.75 (1H, d, J=5.47 Hz) 7.44 (1H, d, J=5.27 Hz) 7.28 (1H, dd, J=3.42, 2.44 Hz) 6.77 (1H, d, J=5.47 Hz) 6.40 (1H, dd, J=3.42, 1.85 Hz) 4.70 (1H, d, J=4.69 Hz) 3.69-3.79 (1H, m) 3.09-3.20 (2H, m) 1.01 (3H, d, J=6.05 Hz)

IC$_{50}$ (p70S6K) "++"

12. 3-(1H-Pyrrolo[2,3-b]pyridin-4-ylamino)-thiophene-2-carboxylic acid (2-phenoxy-ethyl)-amide

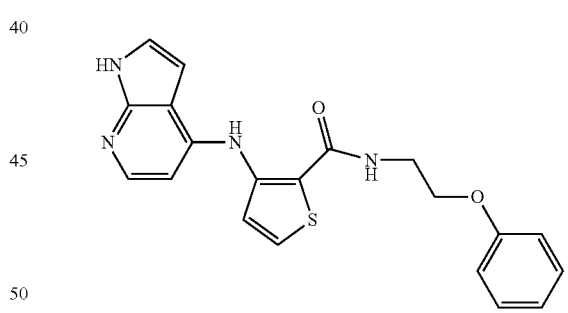

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-phenoxyethylamine instead of 1-BOC-3-aminopyrrolidine. LCMS (ESI) 379 (M+H) 1H NMR (400 MHz, DMSO-d6) δ ppm 11.93 (1H, br. s.) 10.42 (1H, s) 8.34 (1H, t, J=5.47 Hz) 8.04 (1H, d, J=6.15 Hz) 7.85 (1H, d, J=5.37 Hz) 7.42 (1H, d, J=5.37 Hz) 7.37 (1H, d, J=3.51 Hz) 7.21-7.28 (2H, m) 6.89-6.97 (1H, m) 6.87 (2H, dd, J=8.74, 1.02 Hz) 6.77 (1H, d, J=6.25 Hz) 6.58 (1H, d, J=3.32 Hz) 4.04 (2H, t, J=5.95 Hz) 3.60 (2H, q, J=5.92 Hz)

IC$_{50}$ (p70S6K) "++"

13. 3-(1H-Pyrrolo[2,3-b]pyridin-4-ylamino)-thiophene-2-carboxylic acid (2-cyclohex-1-enyl-ethyl)-amide

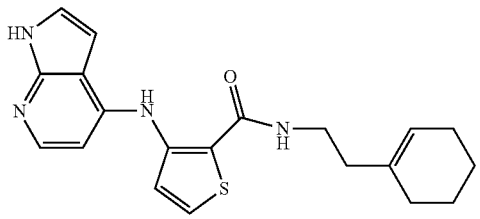 [SMILES: O=C(NCCC1=CCCCC1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(1-cyclohexenyl)ethylamine instead of 1-BOC-3-aminopyrrolidine. LCMS (ESI) 367 (M+H) 1H NMR (400 MHz, DMSO-d6) δ ppm 11.51 (1H, br. s.) 10.20 (1H, s) 7.94-8.06 (2H, m) 7.76 (1H, d, J=5.37 Hz) 7.44 (1H, d, J=5.37 Hz) 7.30 (1H, dd, J=3.37, 2.49 Hz) 6.77 (1H, d, J=5.37 Hz) 6.43 (1H, dd, J=3.47, 1.90 Hz) 5.37 (1H, br. s.) 3.25-3.37 (2H, m) 2.11 (2H, t, J=7.96 Hz) 1.91 (2H, t, J=5.81 Hz) 1.84 (2H, br. s.) 1.49-1.60 (2H, m) 1.36-1.47 (2H, m)

IC$_{50}$ (p70S6K) "+++"

14. 3-(1H-Pyrrolo[2,3-b]pyridin-4-ylamino)-thiophene-2-carboxylic acid [2-(4-sulfamoyl-phenyl)-ethyl]-amide

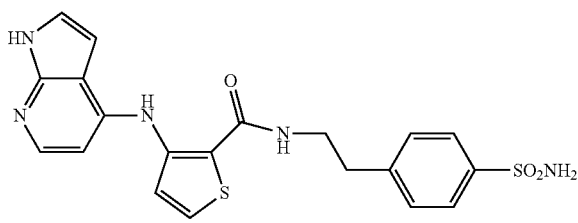 [SMILES: NS(=O)(=O)c1ccc(CCNC(=O)c2sccc2Nc2ccnc3[nH]ccc23)cc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-(2-aminoethyl)benzenesulfonamide instead of 1-BOC-3-aminopyrrolidine. LCMS (ESI) 422 (M+H) 1H NMR (400 MHz, DMSO-d6) δ ppm 11.54 (1H, br. s.) 10.31 (1H, s) 8.23 (1H, t, J=5.86 Hz) 8.02 (1H, d, J=5.37 Hz) 7.68-7.83 (3H, m) 7.48 (1H, d, J=5.47 Hz) 7.42 (2H, d, J=8.30 Hz) 7.32 (1H, d, J=2.93 Hz) 7.28 (2H, s) 6.83 (1H, d, J=5.37 Hz) 6.44 (1H, dd, J=3.51, 1.95 Hz) 3.50 (2H, q, J=7.13 Hz) 2.91 (2H, t, J=7.27 Hz)

IC$_{50}$ (p70S6K) "+++"

15. 3-(1H-Pyrrolo[2,3-b]pyridin-4-ylamino)-thiophene-2-carboxylic acid [2-(1H-imidazol-4-yl)-ethyl]-amide

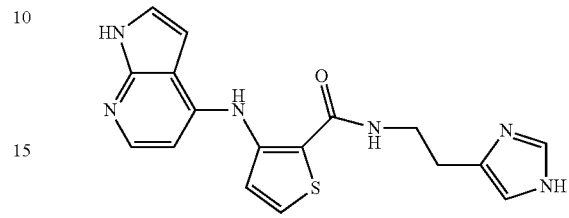

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using histamine instead of 1-BOC-3-aminopyrrolidine. LCMS (ESI) 353 (M+H) 1H NMR (400 MHz, DMSO-d6) δ ppm 11.69-11.97 (1H, m) 11.52 (1H, br. s.) 10.35 (1H, s) 8.24 (1H, br. s.) 8.02 (1H, d, J=5.37 Hz) 7.77 (1H, d, J=5.47 Hz) 7.44-7.54 (2H, m) 7.31 (1H, dd, J=3.32, 2.83 Hz) 6.88 (1H, br. s.) 6.82 (1H, d, J=5.37 Hz) 6.44 (1H, dd, J=3.47, 1.71 Hz) 3.41-3.52 (2H, m) 2.71 (2H, t, J=6.98 Hz)

IC$_{50}$ (p70S6K) "++"

16. 3-(1H-Pyrrolo[2,3-b]pyridin-4-ylamino)-thiophene-2-carboxylic acid (2-morpholin-4-yl-ethyl)-amide

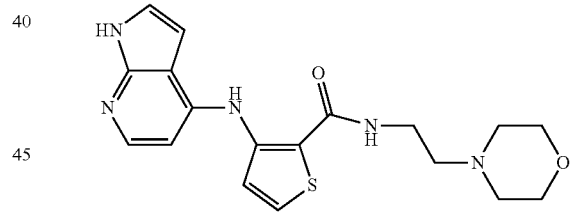

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-(2-aminoethyl)morpholine instead of 1-BOC-3-aminopyrrolidine. LCMS (ESI) 372 (M+H) 1H NMR (400 MHz, DMSO-d6) δ ppm 11.50 (1H, br. s.) 10.03 (1H, s) 8.00 (2H, d, J=5.47 Hz) 7.77 (1H, d, J=5.37 Hz) 7.41 (1H, d, J=5.37 Hz) 7.29 (1H, dd, J=3.42, 2.44 Hz) 6.72 (1H, d, J=5.47 Hz) 6.44 (1H, dd, J=3.47, 1.90 Hz) 3.39-3.46 (4H, m) 3.33-3.39 (2H, m) 2.41 (2H, t, J=6.64 Hz) 2.33 (4H, br. s.)

IC$_{50}$ (p70S6K) "++"

17. 3-(1H-Pyrrolo[2,3-b]pyridin-4-ylamino)-thiophene-2-carboxylic acid (2-pyridin-4-yl-ethyl)-amide

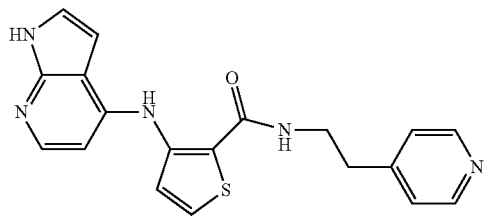 [SMILES: O=C(NCCc1ccncc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-(2-aminoethyl)pyridine instead of 1-BOC-3-aminopyrrolidine. LCMS (ESI) 364 (M+H) 1H NMR (400 MHz, DMSO-d6) δ ppm 11.53 (1H, br. s.) 10.25 (1H, s) 8.40-8.46 (2H, m) 8.21 (1H, t, J=5.54 Hz) 8.02 (1H, d, J=5.32 Hz) 7.77 (1H, d, J=5.47 Hz) 7.47 (1H, d, J=5.42 Hz) 7.32 (1H, dd, J=3.49, 2.56 Hz) 7.21-7.27 (2H, m) 6.81 (1H, d, J=5.47 Hz) 6.43 (1H, dd, J=3.49, 1.88 Hz) 3.47-3.55 (2H, m) 2.85 (2H, t, J=7.15 Hz)

IC$_{50}$ (p70S6K) "++"

18. 3-(1H-Pyrrolo[2,3-b]pyridin-4-ylamino)-thiophene-2-carboxylic acid [2-(3-trifluoromethyl-phenyl)-ethyl]-amide

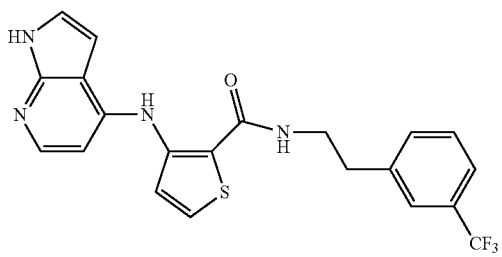 [SMILES: O=C(NCCc1cccc(C(F)(F)F)c1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(3-trifluoromethylphenyl)ethylamine instead of 1-BOC-3-aminopyrrolidine. LCMS (ESI) 431 (M+H) 1H NMR (400 MHz, DMSO-d6) δ ppm 11.53 (1H, br. s.) 10.28 (1H, s) 8.20 (1H, t, J=5.56 Hz) 8.02 (1H, d, J=5.27 Hz) 7.77 (1H, d, J=5.47 Hz) 7.60 (1H, s) 7.44-7.56 (4H, m) 7.31 (1H, dd, J=3.32, 2.54 Hz) 6.82 (1H, d, J=5.47 Hz) 6.42 (1H, dd, J=3.42, 1.85 Hz) 3.47-3.56 (2H, m) 2.94 (2H, t, J=7.03 Hz)

IC$_{50}$ (p70S6K) "+++"

19. 3-(1H-Pyrrolo[2,3-b]pyridin-4-ylamino)-thiophene-2-carboxylic acid (2-pyridin-2-yl-ethyl)-amide

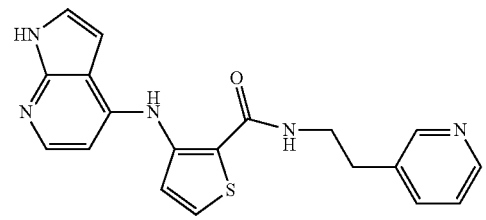 [SMILES: O=C(NCCc1cccnc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(2-aminoethyl)pyridine instead of 1-BOC-3-aminopyrrolidine. LCMS (ESI) 364 (M+H) 1H NMR (400 MHz, DMSO-d6) δ ppm 11.53 (1H, br. s.) 10.24 (1H, s) 8.41-8.47 (1H, m) 8.24 (1H, t, J=5.56 Hz) 8.02 (1H, d, J=5.37 Hz) 7.77 (1H, d, J=5.47 Hz) 7.61-7.70 (1H, m) 7.46 (1H, d, J=5.37 Hz) 7.31 (1H, dd, J=3.32, 2.44 Hz) 7.25 (1H, d, J=7.81 Hz) 7.13-7.20 (1H, m) 6.79 (1H, d, J=5.37 Hz) 6.44 (1H, dd, J=3.42, 1.85 Hz) 3.53-3.68 (2H, m) 2.98 (2H, t, J=7.37 Hz)

IC$_{50}$ (p70S6K) "++"

20. 3-(1H-Pyrrolo[2,3-b]pyridin-4-ylamino)-thiophene-2-carboxylic acid [2-(3-chloro-phenyl)-ethyl]-amide

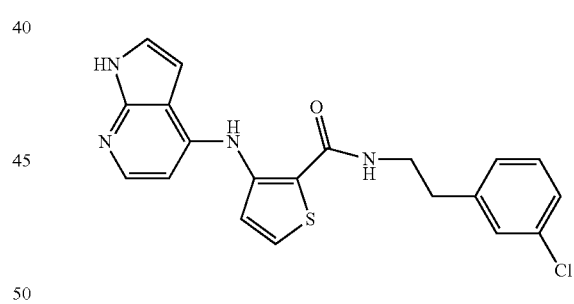

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(3-chlorophenyl)ethylamine instead of 1-BOC-3-aminopyrrolidine. LCMS (ESI) 396 (M+H) 1H NMR (400 MHz, DMSO-d6) δ ppm 11.59 (1H, br. s.) 10.29 (1H, s) 8.19 (1H, t, J=5.71 Hz) 8.03 (1H, d, J=5.47 Hz) 7.78 (1H, d, J=5.42 Hz) 7.47 (1H, d, J=5.37 Hz) 7.32 (2H, td, J=3.77, 1.93 Hz) 7.27 (1H, d, J=7.27 Hz) 7.22 (1H, t, J=1.83 Hz) 7.17 (1H, t, J=1.56 Hz) 6.81 (1H, d, J=5.52 Hz) 6.45 (1H, dd, J=3.49, 1.68 Hz) 3.43-3.51 (2H, m) 2.84 (2H, t, J=7.32 Hz)

IC$_{50}$ (p70S6K) "+++"

21. 3-(1H-Pyrrolo[2,3-b]pyridin-4-ylamino)-thiophene-2-carboxylic acid (2-thiophen-2-yl-ethyl)-amide

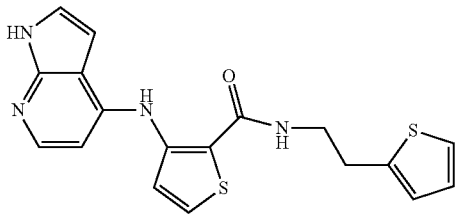 [SMILES: O=C(NCCc1cccs1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using thiophene-2-ethylamine instead of 1-BOC-3-aminopyrrolidine. LCMS (ESI) 369 (M+H) 1H NMR (400 MHz, DMSO-d6) δ ppm 12.00 (1H, br. s.) 10.44 (1H, s) 8.30 (1H, t, J=5.56 Hz) 8.06 (1H, d, J=6.25 Hz) 7.85 (1H, d, J=5.47 Hz) 7.37-7.43 (2H, m) 7.29 (1H, dd, J=5.08, 1.17 Hz) 6.89 (1H, dd, J=5.08, 3.32 Hz) 6.86 (1H, dd, J=3.32, 0.98 Hz) 6.78 (1H, d, J=6.44 Hz) 6.59 (1H, d, J=3.51 Hz) 3.42-3.49 (2H, m) 3.00 (2H, t, J=7.13 Hz)

IC$_{50}$ (p70S6K) "+++"

22. 3-(1H-Pyrrolo[2,3-b]pyridin-4-ylamino)-thiophene-2-carboxylic acid [2-(3-fluoro-phenyl)-ethyl]-amide

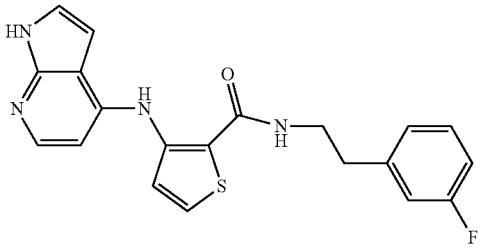 [SMILES: O=C(NCCc1cccc(F)c1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(3-fluorophenyl)ethylamine instead of 1-BOC-3-aminopyrrolidine. LCMS (ESI) 381 (M+H) 1H NMR (400 MHz, DMSO-d6) δ ppm 11.87 (1H, br. s.) 10.38 (1H, s) 8.22 (1H, t, J=5.66 Hz) 8.05 (1H, d, J=6.05 Hz) 7.82 (1H, d, J=5.47 Hz) 7.42 (1H, d, J=5.27 Hz) 7.37 (1H, d, J=3.51 Hz) 7.26 (1H, td, J=8.00, 6.44 Hz) 7.04 (2H, dd, J=8.00, 2.54 Hz) 6.98 (1H, td, J=8.88, 2.93 Hz) 6.77 (1H, d, J=6.05 Hz) 6.54 (1H, d, J=3.51 Hz) 3.42-3.51 (2H, m) 2.82 (2H, t, J=7.13 Hz)

IC$_{50}$ (p70S6K) "+++"

23. 3-(1H-Pyrrolo[2,3-b]pyridin-4-ylamino)-thiophene-2-carboxylic acid [2-(4-fluoro-phenyl)-ethyl]-amide

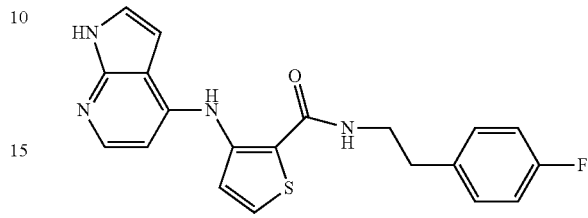

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(4-fluorophenyl)ethylamine instead of 1-BOC-3-aminopyrrolidine. LCMS (ESI) 381 (M+H) 1H NMR (400 MHz, DMSO-d6) δ ppm 12.19 (1H, br. s.) 10.45 (1H, s) 8.21 (1H, t, J=5.76 Hz) 8.07 (1H, d, J=6.64 Hz) 7.86 (1H, d, J=5.27 Hz) 7.42 (1H, dd, J=3.12, 1.76 Hz) 7.36 (1H, d, J=5.27 Hz) 7.18 (2H, dd, J=8.79, 5.66 Hz) 7.00 (2H, t, J=8.98 Hz) 6.73 (1H, d, J=6.44 Hz) 6.63 (1H, d, J=3.32 Hz) 3.39-3.47 (2H, m) 2.75 (2H, t, J=7.22 Hz)

IC$_{50}$ (p70S6K) "+++"

24. 3-(1H-Pyrrolo[2,3-b]pyridin-4-ylamino)-thiophene-2-carboxylic acid [2-(furan-2-ylmethylsulfanyl)-ethyl]-amide

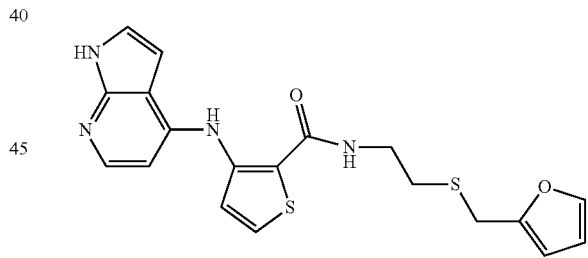

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(furfurylthio)ethylamine of 1-BOC-3-aminopyrrolidine. LCMS (ESI) 399 (M+H) 1H NMR (400 MHz, DMSO-d6) δ ppm 11.92 (1H, br. s.) 10.46 (1H, s) 8.29 (1H, t, J=5.71 Hz) 8.06 (1H, d, J=6.05 Hz) 7.84 (1H, d, J=5.37 Hz) 7.56 (1H, td, J=1.10, 0.54 Hz) 7.44 (1H, d, J=5.37 Hz) 7.38 (1H, dd, J=3.51, 1.76 Hz) 6.80 (1H, d, J=6.15 Hz) 6.57 (1H, d, J=3.32 Hz) 6.36 (1H, dd, J=3.17, 1.90 Hz) 6.28 (1H, dd, J=3.22, 0.59 Hz) 3.78 (2H, s) 3.36-3.44 (2H, m) 2.59 (2H, dd, J=7.96, 6.20 Hz)

IC$_{50}$ (p70S6K) "+++"

25. 3-(1H-Pyrrolo[2,3-b]pyridin-4-ylamino)-thiophene-2-carboxylic acid (2-o-tolyl-ethyl)-amide

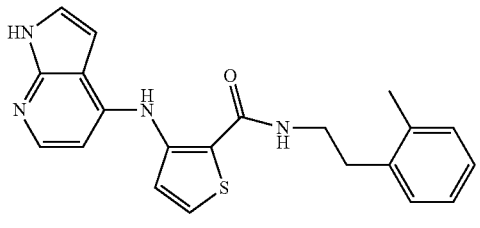 [SMILES: Cc1ccccc1CCNC(=O)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(2-methylphenyl)ethylamine instead of 1-BOC-3-aminopyrrolidine. LCMS (ESI) 377 (M+H) 1H NMR (400 MHz, DMSO-d6) δ ppm 11.97 (1H, br. s.) 10.45 (1H, s) 8.28 (1H, t, J=5.66 Hz) 8.06 (1H, d, J=6.25 Hz) 7.84 (1H, d, J=5.47 Hz) 7.36-7.43 (2H, m) 7.01-7.15 (4H, m) 6.78 (1H, d, J=6.25 Hz) 6.59 (1H, d, J=3.51 Hz) 3.39 (2H, td, J=7.52, 6.05 Hz) 2.77 (2H, d, J=7.81 Hz) 2.29 (3H, s)

IC$_{50}$ (p70S6K) "+++"

26. 3-(1H-Pyrrolo[2,3-b]pyridin-4-ylamino)-thiophene-2-carboxylic acid [2-(3-methoxy-phenyl)-ethyl]-amide

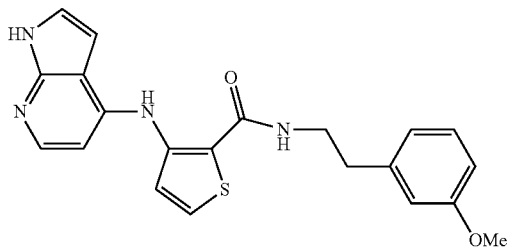 [SMILES: COc1cccc(CCNC(=O)c2sccc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(3-methoxyphenyl)ethylamine instead of 1-BOC-3-aminopyrrolidine. LCMS (ESI) 393 (M+H) 1H NMR (400 MHz, DMSO-d6) δ ppm 11.68 (1H, br. s.) 10.34 (1H, s) 8.19 (1H, t, J=5.61 Hz) 8.03 (1H, d, J=5.66 Hz) 7.79 (1H, d, J=5.37 Hz) 7.45 (1H, d, J=5.37 Hz) 7.34 (1H, d, J=3.32 Hz) 7.16 (1H, t, J=8.10 Hz) 6.72-6.82 (4H, m) 6.48 (1H, d, J=3.32 Hz) 3.71 (3H, s) 3.46 (2H, dt, J=8.00, 6.25 Hz) 2.79 (2H, t, J=7.27 Hz)

IC$_{50}$ (p70S6K) "+++"

27. 3-(1H-Pyrrolo[2,3-b]pyridin-4-ylamino)-thiophene-2-carboxylic acid [2-(4-bromo-phenyl)-ethyl]-amide

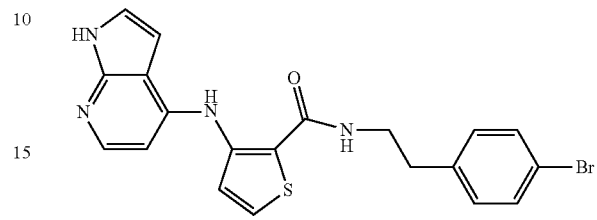

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(4-bromophenyl)ethylamine instead of 1-BOC-3-aminopyrrolidine. LCMS (ESI) 442 (M+H) 1H NMR (400 MHz, DMSO-d6) δ ppm 11.53 (1H, br. s.) 10.25 (1H, s) 8.17 (1H, t, J=5.47 Hz) 8.02 (1H, d, J=5.47 Hz) 7.77 (1H, d, J=5.47 Hz) 7.46 (1H, d, J=5.47 Hz) 7.44 (2H, d, J=8.20 Hz) 7.32 (1H, d, J=3.32 Hz) 7.18 (2H, d, J=8.20 Hz) 6.80 (1H, d, J=5.47 Hz) 6.43 (1H, dd, J=3.42, 1.85 Hz) 3.40-3.52 (2H, m) 2.80 (2H, t, J=7.22 Hz)

IC$_{50}$ (p70S6K) "+++"

28. 3-(1H-Pyrrolo[2,3-b]pyridin-4-ylamino)-thiophene-2-carboxylic acid [2-(4-methoxy-phenyl)-ethyl]-amide

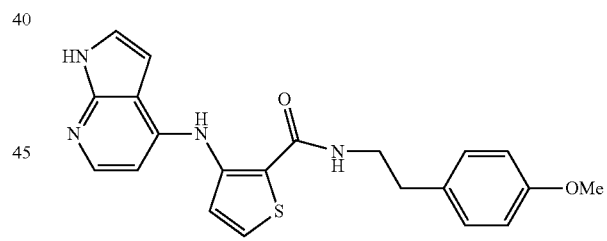

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-(4-methoxyphenyl)ethylamine instead of 1-BOC-3-aminopyrrolidine. LCMS (ESI) 393 (M+H) 1H NMR (400 MHz, DMSO-d6) δ ppm 11.52 (1H, br. s.) 10.24 (1H, s) 8.14 (0H, t) 8.02 (1H, d, J=5.42 Hz) 7.77 (1H, d, J=5.42 Hz) 7.46 (1H, d, J=5.37 Hz) 7.31 (1H, dd, J=3.34, 2.56 Hz) 7.13 (2H, d, J=8.69 Hz) 6.76-6.84 (3H, m) 6.44 (1H, dd, J=3.49, 1.93 Hz) 3.69 (3H, s) 3.37-3.48 (2H, m) 2.75 (2H, t, J=7.37 Hz)

IC$_{50}$ (p70S6K) "+++"

29. 3-(1H-Pyrrolo[2,3-b]pyridin-4-ylamino)-thiophene-2-carboxylic acid (2-benzylamino-ethyl)-amide

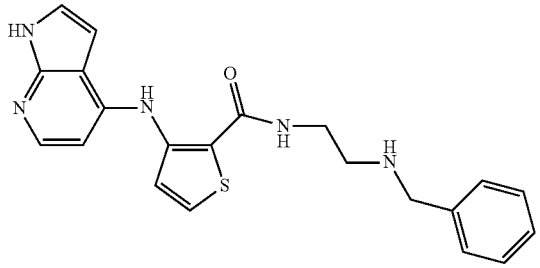 [SMILES: O=C(NCCNCc1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-benzylethylenediamine instead of 1-BOC-3-aminopyrrolidine. LCMS (ESI) 392 (M+H) 1H NMR (400 MHz, DMSO-d6) δ ppm 11.52 (1H, br. s.) 10.27 (1H, s) 8.05 (1H, t, J=5.47 Hz) 8.01 (1H, d, J=5.37 Hz) 7.77 (1H, d, J=5.37 Hz) 7.46 (1H, d, J=5.47 Hz) 7.14-7.33 (7H, m) 6.80 (1H, d, J=5.56 Hz) 6.43 (1H, dd, J=3.42, 1.85 Hz) 3.69 (2H, s) 3.35 (2H, d, J=6.05 Hz) 2.65 (2H, t, J=6.59 Hz)

IC$_{50}$ (p70S6K) "+++"

30. 3-(1H-Pyrrolo[2,3-b]pyridin-4-ylamino)-thiophene-2-carboxylic acid 3-chloro-benzylamide

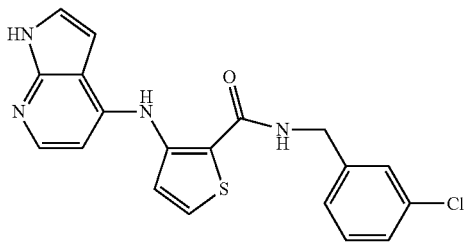 [SMILES: O=C(NCc1cccc(Cl)c1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-chlorobenzylamine instead of 1-BOC-3-aminopyrrolidine. LCMS (ESI) 383 (M+H) 1H NMR (400 MHz, DMSO-d6) δ ppm 11.53 (1H, br. s.) 10.27 (1H, s) 8.72 (1H, t, J=5.95 Hz) 8.03 (1H, d, J=5.47 Hz) 7.82 (1H, d, J=5.47 Hz) 7.50 (1H, d, J=5.47 Hz) 7.21-7.41 (5H, m) 6.84 (1H, d, J=5.47 Hz) 6.41 (1H, dd, J=3.51, 1.95 Hz) 4.46 (2H, d, J=5.86 Hz)

IC$_{50}$ (p70S6K) "+++"

31. 3-(1H-Pyrrolo[2,3-b]pyridin-4-ylamino)-thiophene-2-carboxylic acid (4-hydroxy-butyl)-amide

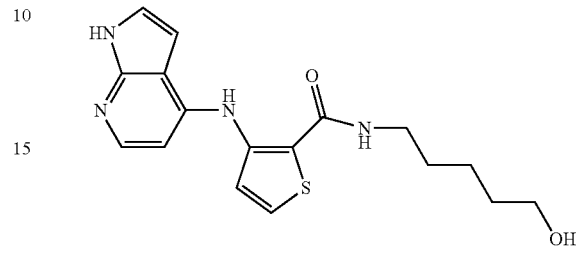

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-amino-1-butanol instead of 1-BOC-3-aminopyrrolidine. LCMS (ESI) 330 (M+H) 1H NMR (400 MHz, DMSO-d6) δ ppm 11.53 (1H, br. s.) 10.36 (1H, s) 8.10 (1H, t, J=5.66 Hz) 8.02 (1H, d, J=5.47 Hz) 7.77 (1H, d, J=5.27 Hz) 7.48 (1H, d, J=5.47 Hz) 7.31 (1H, dd, J=3.32, 2.54 Hz) 6.82 (1H, d, J=5.47 Hz) 6.43 (1H, dd, J=3.51, 1.76 Hz) 4.39 (1H, t, J=5.17 Hz) 3.36-3.43 (2H, m) 3.18-3.28 (2H, m) 1.53 (2H, dd, J=8.20, 6.83 Hz) 1.36-1.47 (2H, m)

IC$_{50}$ (p70S6K) "++"

32. 3-(1H-Pyrrolo[2,3-b]pyridin-4-ylamino)-thiophene-2-carboxylic acid (4-acetylamino-butyl)-amide

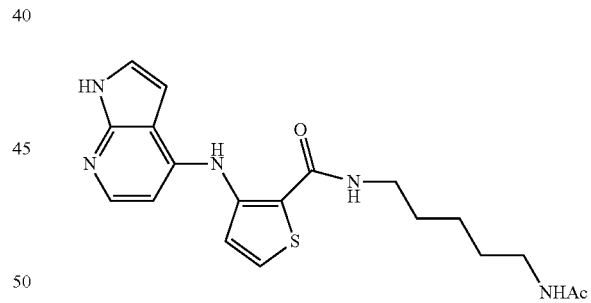

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-(4-aminobutyl)acetamide instead of 1-BOC-3-aminopyrrolidine. LCMS (ESI) 372 (M+H) 1H NMR (400 MHz, DMSO-d6) δ ppm 11.52 (1H, br. s.) 10.36 (1H, s) 8.11 (1H, t, J=5.56 Hz) 8.02 (1H, d, J=5.47 Hz) 7.77 (2H, d, J=5.47 Hz) 7.48 (1H, d, J=5.47 Hz) 7.31 (1H, dd, J=3.51, 2.54 Hz) 6.82 (1H, d, J=5.47 Hz) 6.43 (1H, dd, J=3.51, 1.95 Hz) 3.19-3.27 (2H, m) 2.96-3.07 (2H, m) 1.77 (3H, s) 1.44-1.59 (2H, m) 1.39 (2H, dd, J=8.40, 6.83 Hz)

IC$_{50}$ (p70S6K) "++"

33. 3-{[3-(1H-Pyrrolo[2,3-b]pyridin-4-ylamino)-thiophene-2-carbonyl]-amino}-propionic acid ethyl ester

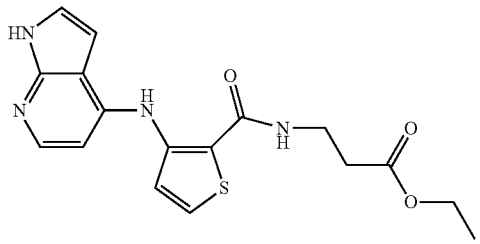 [SMILES: CCOC(=O)CCNC(=O)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-amino-propionic acid ethyl ester instead of 1-BOC-3-aminopyrrolidine. LCMS (ESI) 359 (M+H) 1H NMR (400 MHz, DMSO-d6) δ ppm 11.54 (1H, br. s.) 10.27 (1H, s) 8.17 (1H, t, J=5.37 Hz) 8.02 (1H, d, J=5.47 Hz) 7.78 (1H, d, J=5.47 Hz) 7.47 (1H, d, J=5.47 Hz) 7.32 (1H, d, J=3.32 Hz) 6.81 (1H, d, J=5.47 Hz) 6.44 (1H, dd, J=3.42, 1.66 Hz) 4.03 (2H, q, J=7.03 Hz) 3.43-3.53 (2H, m) 2.55 (2H, t, J=7.03 Hz) 1.15 (3H, t, J=7.03 Hz)

IC$_{50}$ (p70S6K) "++"

34. 3-(1H-Pyrrolo[2,3-b]pyridin-4-ylamino)-thiophene-2-carboxylic acid (2-phenylamino-ethyl)-amide

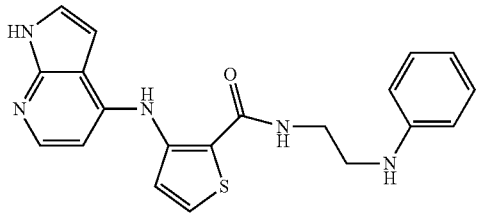 [SMILES: O=C(NCCNc1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-phenylethylenediamine instead of 1-BOC-3-aminopyrrolidine. LCMS (ESI) 378 (M+H) 1H NMR (400 MHz, METHANOL-d4) δ ppm 8.00 (1H, d, J=5.66 Hz) 7.62 (1H, d, J=5.42 Hz) 7.45 (1H, d, J=5.37 Hz) 7.25 (1H, d, J=3.56 Hz) 7.07 (2H, dd, J=8.66, 7.30 Hz) 6.86 (1H, d, J=5.66 Hz) 6.51-6.67 (4H, m) 3.55 (2H, t, J=6.47 Hz) 3.25-3.30 (2H, m)

IC$_{50}$ (p70S6K) "+++"

35. 3-(1H-Pyrrolo[2,3-b]pyridin-4-ylamino)-thiophene-2-carboxylic acid (4-chloro-phenyl)-amide

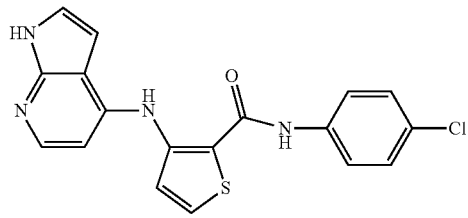 [SMILES: O=C(Nc1ccc(Cl)cc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-chloroaniline instead of 1-BOC-3-aminopyrrolidine. LCMS (ESI) 369 (M+H) 1H NMR (400 MHz, DMSO-d6) δ ppm 11.56 (1H, br. s.) 10.12 (1H, s) 9.99 (1H, s) 8.04 (1H, d, J=5.47 Hz) 7.91 (1H, d, J=0.10 Hz) 7.71 (2H, d, J=8.93 Hz) 7.52 (1H, d, J=5.37 Hz) 7.37-7.43 (2H, m) 7.33 (1H, dd, J=3.25, 2.61 Hz) 6.85 (1H, d, J=5.42 Hz) 6.46 (1H, dd, J=3.49, 1.88 Hz)

IC$_{50}$ (p70S6K) "+++"

36. 3-(1H-Pyrrolo[2,3-b]pyridin-4-ylamino)-thiophene-2-carboxylic acid (4-methoxy-phenyl)-amide

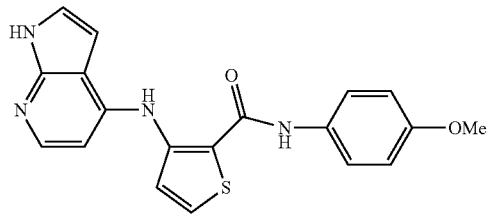 [SMILES: COc1ccc(NC(=O)c2sccc2Nc2ccnc3[nH]ccc23)cc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-methoxyaniline instead of 1-BOC-3-aminopyrrolidine. LCMS (ESI) 365 (M+H) 1H NMR (400 MHz, DMSO-d6) δ ppm 11.51 (1H, br. s.) 10.14 (1H, s) 9.73 (1H, s) 8.00 (1H, d, J=5.42 Hz) 7.85 (1H, d, J=5.42 Hz) 7.44-7.55 (3H, m) 7.29 (1H, dd, J=3.20, 2.71 Hz) 6.89 (2H, d, J=8.98 Hz) 6.80 (1H, d, J=5.47 Hz) 6.42 (1H, dd, J=3.47, 1.90 Hz) 3.72 (3H, s)

IC$_{50}$ (p70S6K) "+++"

37. 3-(1H-Pyrrolo[2,3-b]pyridin-4-ylamino)-thiophene-2-carboxylic acid (4-fluoro-phenyl)-amide

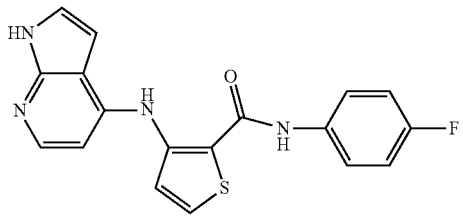 [SMILES: O=C(Nc1ccc(F)cc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-fluoroaniline of 1-BOC-3-aminopyrrolidine. LCMS (ESI) 353 (M+H) 1H NMR (400 MHz, DMSO-d6) δ ppm 11.53 (1H, br. s.) 10.11 (1H, s) 9.90 (1H, s) 8.01 (1H, d, J=5.42 Hz) 7.88 (1H, d, J=5.42 Hz) 7.64 (2H, dd, J=9.13, 5.08 Hz) 7.49 (1H, d, J=5.42 Hz) 7.30 (1H, dd, J=3.25, 2.66 Hz) 7.16 (2H, t, J=8.93 Hz) 6.82 (1H, d, J=5.47 Hz) 6.43 (1H, dd, J=3.49, 1.93 Hz)

IC$_{50}$ (p70S6K) "+++"

39. 3-(1H-Pyrrolo[2,3-b]pyridin-4-ylamino)-thiophene-2-carboxylic acid (3-methoxy-phenyl)-amide

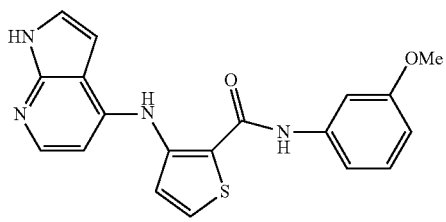 [SMILES: COc1cccc(NC(=O)c2sccc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-methoxaniline instead of 1-BOC-3-aminopyrrolidine. LCMS (ESI) 365 (M+H) 1H NMR (400 MHz, DMSO-d6) δ ppm 11.55 (1H, br. s.) 10.06 (1H, s) 9.83 (1H, s) 8.03 (1H, d, J=5.42 Hz) 7.90 (1H, d, J=5.42 Hz) 7.49 (1H, d, J=5.42 Hz) 7.32 (1H, dd, J=3.51, 2.44 Hz) 7.20-7.30 (3H, m) 6.81 (1H, d, J=5.42 Hz) 6.68 (1H, dt, J=7.42, 2.12 Hz) 6.47 (1H, dd, J=3.56, 1.90 Hz) 3.74 (3H, s)

IC$_{50}$ (p70S6K) "++"

40. 3-(1H-Pyrrolo[2,3-b]pyridin-4-ylamino)-thiophene-2-carboxylic acid [2-(4-methoxy-benzylamino)-ethyl]-amide

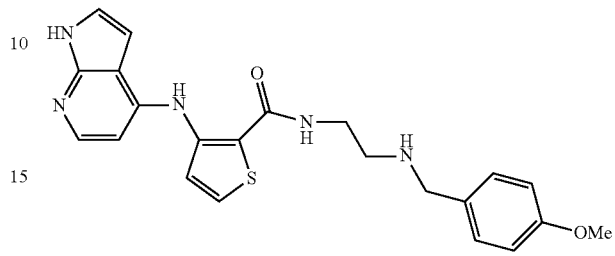

To a solution of 3-(1H-Pyrrolo[2,3-b]pyridin-4-ylamino)-thiophene-2-carboxylic acid (2-amino-ethyl)-amide (45 mg, 0.13 mmol), 4-methoxy benzaldehyde (16 uL, 0.13 mmol), and glacial acetic acid (8 uL, 0.13 mmol) in methanol (1 mL) was added sodium triacetoxy borohydride (84 mg, 0.4 mmol) portionwise. The solution was stirred at 50° C. for 18 h. The solution was absorbed onto Celite and purified by ISCO Companion (silica 0-10% methanol, methylene chloride, 1% ammonium hydroxide) to afford 3-(1H-Pyrrolo[2,3-b]pyridin-4-ylamino)-thiophene-2-carboxylic acid [2-(4-methoxy-benzylamino)-ethyl]-amide (56 mg, 75%) LCMS (ESI) 422 (M+H) $^1$H NMR (400 MHz, DMSO-d6) δ ppm 10.26 (1H, br. s.) 7.98-8.07 (2H, m) 7.77 (1H, d, J=5.47 Hz) 7.46 (1H, d, J=5.47 Hz) 7.30 (1H, d, J=3.32 Hz) 7.19 (2H, d, J=8.59 Hz) 6.76-6.84 (2H, m) 6.43 (1H, d, J=3.51 Hz) 3.69 (3H, s) 3.60 (2H, s) 3.33 (2H, q, J=6.25 Hz) 2.61 (2H, t, J=6.64 Hz)

IC$_{50}$ (p70S6K) "+++"

41. 3-(1H-Pyrrolo[2,3-b]pyridin-4-ylamino)-thiophene-2-carboxylic acid {2-[(pyridin-2-ylmethyl)-amino]-ethyl}-amide

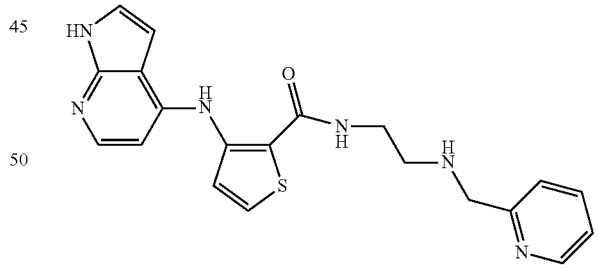

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 2-pyridinecarboxaldehyde instead of 4-methoxy benzaldehyde. LCMS (ESI) 393 (M+H) 1H NMR (400 MHz, DMSO-d6) δ ppm 11.51 (1H, br. s.) 10.27 (1H, s) 8.46 (1H, ddd, J=4.81, 1.66, 0.76 Hz) 8.07 (1H, t, J=5.61 Hz) 8.01 (1H, d, J=5.37 Hz) 7.77 (1H, d, J=5.47 Hz) 7.68 (1H, td, J=7.68, 1.73 Hz) 7.47 (1H, d, J=5.42 Hz) 7.39 (1H, d, J=7.71 Hz) 7.29 (1H, d, J=2.64 Hz) 7.20 (1H, ddd, J=7.47, 4.91, 0.90 Hz) 6.80 (1H, d, J=5.47 Hz) 6.42 (1H, dd, J=3.49, 1.98 Hz) 3.78 (2H, s) 3.36 (2H, q, J=6.12 Hz) 2.68 (2H, t, J=6.83 Hz)

IC$_{50}$ (p70S6K) "+++"

42. 3-(1H-Pyrrolo[2,3-b]pyridin-4-ylamino)-thiophene-2-carboxylic acid (2-amino-ethyl)-amide

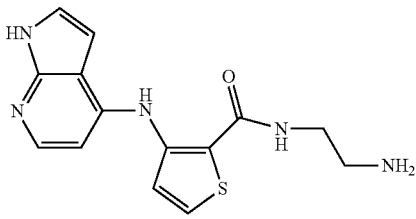 [SMILES: NCCNC(=O)c1sccc1Nc1ccnc2[nH]ccc12]

A solution of 3-(1H-pyrrolo[2,3-b]pyridin-4-ylamino) thiophene-2-carbonyl chloride (2.4 g, 7.7 mmol), tert-butyl-2-amino ethyl carbamate (1.9 g, 11.6 mmol), and diisopropylethylamine (4.0 mL, 23.1 mmol) were combined in acetonitrile (40 mL) and stirred at room temperature for 18 h. The solvent was removed under reduced pressure and the crude material was partitioned between water and 10% methanol in methylene chloride. The aqueous layer was basified with 1N NaOH and extracted with methylene chloride. The organic layers were combined, dried with magnesium sulfate, filtered and concentrate in vacuo. The residue was purified by ISCO Companion (silica, 0-10% methanol, methylene chloride, 1% ammonium hydroxide) to afford (2-{3-(1H-pyrrolo[2,3-b]pyridine-4-ylamino)-thiophene-2-carbonyl]-amino}-ethyl)-carbamic acid tert-butyl ester (1.0 g, 33%) LCMS (ESI) 402 (M+H).

Hydrogen chloride (4.0 M in 1,4-dioxane) (5.1 mL, 20 mmol) was added to a suspension of (2-{3-(1H-pyrrolo[2,3-b]pyridine-4-ylamino)-thiophene-2-carbonyl]-amino}-ethyl)-carbamic acid tert-butyl ester (820 mg, 2.0 mmol) in tetrahydrofuran (11 mL) and stirred at room temperature for 18 h. The resultant precipitate was filtered and dried under vacuum to afford 3-(1H-Pyrrolo[2,3-b]pyridin-4-ylamino)-thiophene-2-carboxylic acid (2-amino-ethyl)-amide (740 mg, 95%) LCMS (ESI) 302 (M+H) $^1$H NMR (400 MHz, DMSO-d6) δ ppm 12.57 (1H, br. s.) 10.87 (1H, s) 8.63 (1H, t, J=5.56 Hz) 8.05-8.19 (3H, m) 7.87-7.94 (1H, m) 7.40 (1H, dd, J=3.32, 2.54 Hz) 7.29-7.35 (1H, m) 6.97 (1H, br. s.) 6.67-6.78 (1H, m) 3.41-3.51 (2H, m) 2.93 (2H, q, J=5.99 Hz)

IC$_{50}$ (p70S6K) "+++"

43. R-[3-(1H-Pyrrolo[2,3-b]pyridin-4-ylamino)-thiophene-2-carboxylic acid (2-hydroxy-1-phenyl-ethyl)-amide]

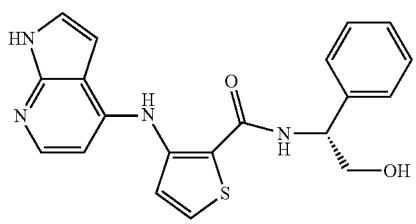 [SMILES: O=C(N[C@@H](CO)c1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (R)-2-phenylglycinol instead of 1-BOC-3-aminopyrrolidine. LCMS (ESI) 379 (M+H) 1H NMR (400 MHz, DMSO-d6) δ ppm 11.51 (1H, br. s.) 10.15 (1H, s) 8.33 (1H, d, J=8.00 Hz) 8.00 (1H, d, J=5.37 Hz) 7.82 (1H, d, J=5.37 Hz) 7.45 (1H, d, J=5.42 Hz) 7.32-7.37 (2H, m) 7.25-7.31 (3H, m) 7.18-7.24 (1H, m) 6.76 (1H, d, J=5.52 Hz) 6.39 (1H, dd, J=3.56, 1.90 Hz) 5.08 (1H, td, J=7.69, 5.66 Hz) 4.92 (1H, t, J=5.71 Hz) 3.58-3.74 (2H, m)

IC$_{50}$ (p70S6K) "+"

44. S-[3-(1H-Pyrrolo[2,3-b]pyridin-4-ylamino)-thiophene-2-carboxylic acid (2-hydroxy-1-phenyl-ethyl)-amide]

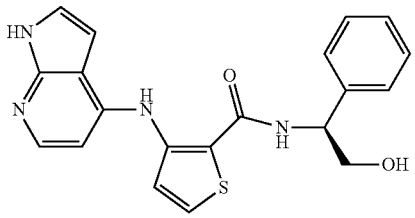 [SMILES: O=C(N[C@H](CO)c1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-2-phenylglycinol instead of 1-BOC-3-aminopyrrolidine. LCMS (ESI) 379 (M+H) 1H NMR (400 MHz, DMSO-d6) δ ppm 11.51 (1H, br. s.) 10.15 (1H, s) 8.33 (1H, d, J=8.00 Hz) 8.00 (1H, d, J=5.42 Hz) 7.81 (1H, d, J=0.10 Hz) 7.45 (1H, d, J=5.42 Hz) 7.32-7.37 (2H, m) 7.25-7.31 (3H, m) 7.16-7.24 (1H, m) 6.76 (1H, d, J=5.47 Hz) 6.39 (1H, dd, J=3.49, 1.83 Hz) 5.08 (1H, td, J=7.70, 5.59 Hz) 4.92 (1H, t, J=5.73 Hz) 3.57-3.76 (2H, m)

IC$_{50}$ (p70S6K) "+++"

45. 3-(1H-Pyrrolo[2,3-b]pyridin-4-ylamino)-thiophene-2-carboxylic acid [2-(acetyl-benzyl-amino)-ethyl]-amide

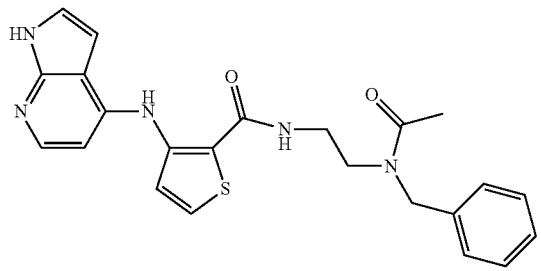 [SMILES: CC(=O)N(CCNC(=O)c1sccc1Nc1ccnc2[nH]ccc12)Cc1ccccc1]

A solution of 3-(1H-Pyrrolo[2,3-b]pyridin-4-ylamino)-thiophene-2-carboxylic acid (2-benzylamino-ethyl)-amide (95 mg, 0.24 mmol), diisopropylethylamine (84 uL, 0.49 mmol) and acetyl chloride (25 uL, 0.37 mmol) in tetrahydrofuran (2.0 mL) was stirred at room temperature for 18 h. The solution was concentrated in vacuo then purified by ISCO Companion (silica, 10% methanol, methylene chloride, 1% ammonium hydroxide) to afford 3-(1H-Pyrrolo[2,3-b]pyridin-4-ylamino)-thiophene-2-carboxylic acid [2-(acetyl-benzyl-amino)-ethyl]-amide (25 mg, 24%). LCMS (ESI) 434 (M+H) 1H NMR (400 MHz, DMSO-d6) δ ppm 11.56 (1H, br. s.) 10.16-10.43 (1H, m) 8.15 (0H, t, J=5.00 Hz) 8.02 (1H, t, J=2.71 Hz) 7.72-7.86 (1H, m) 7.44-7.54 (1H, m) 7.13-7.39 (6H, m) 6.83 (1H, dd, J=12.23, 5.49 Hz) 6.36-6.50 (1H, m) 4.49-4.61 (2H, m) 3.34-3.50 (4H, m) 1.91-2.19 (3H, m)

IC$_{50}$ (p70S6K) "++"

46. 3-(1H-Pyrrolo[2,3-b]pyridin-4-ylamino)-thiophene-2-carboxylic acid {2-[(thiophen-3-ylmethyl)-amino]-ethyl}-amide

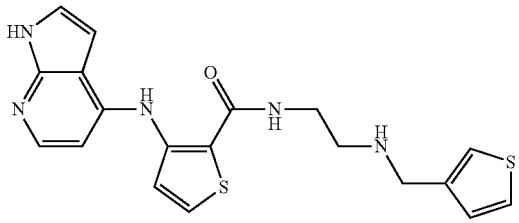 [SMILES: O=C(NCCNCc1ccsc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-thiophenecarboxaldehyde instead of 4-methoxy benzaldehyde. LCMS (ESI) 398 (M+H) 1H NMR (400 MHz, DMSO-d6) δ ppm 11.52 (1H, br. s.) 10.26 (1H, s) 7.98-8.08 (2H, m) 7.77 (1H, d, J=5.42 Hz) 7.46 (1H, d, J=5.42 Hz) 7.42 (1H, dd, J=4.93, 2.98 Hz) 7.30 (1H, dd, J=3.29, 2.66 Hz) 7.24 (1H, dd, J=2.78, 1.03 Hz) 7.05 (1H, dd, J=4.91, 1.20 Hz) 6.80 (1H, d, J=5.42 Hz) 6.43 (1H, dd, J=3.44, 1.93 Hz) 3.67 (2H, s) 3.34 (2H, d, J=5.76 Hz) 2.64 (2H, t, J=6.54 Hz)

IC$_{50}$ (p70S6K) "+++"

47. 3-(1H-Pyrrolo[2,3-b]pyridin-4-ylamino)-thiophene-2-carboxylic acid [2-(bis-furan-3-ylmethyl-amino)-ethyl]-amide

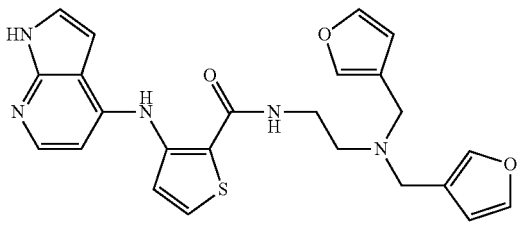 [SMILES: O=C(NCCN(Cc1ccoc1)Cc1ccoc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-furaldehyde instead of 4-methoxy benzaldehyde. LCMS (ESI) 462 (M+H) 1H NMR (400 MHz, DMSO-d6) δ ppm 11.52 (1H, br. s.) 10.25 (1H, s) 8.02 (1H, d, J=5.42 Hz) 7.94 (1H, t, J=5.78 Hz) 7.78 (1H, d, J=5.42 Hz) 7.56 (2H, s) 7.54 (2H, t, J=1.64 Hz) 7.46 (1H, d, J=5.47 Hz) 7.31 (1H, d, J=2.83 Hz) 6.80 (1H, d, J=5.42 Hz) 6.43 (3H, dd, J=3.54, 1.98 Hz) 3.33-3.46 (6H, m)

IC$_{50}$ (p70S6K) "+++"

48. 3-(1H-Pyrrolo[2,3-b]pyridin-4-ylamino)-thiophene-2-carboxylic acid [2-(2-trifluoromethoxy-benzylamino)-ethyl]amide

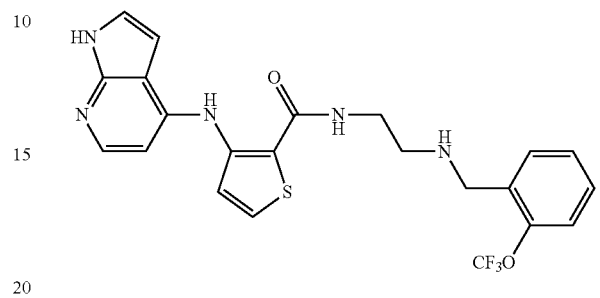

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 2-(trifluoromethoxy)benzaldehyde instead of 4-methoxy benzaldehyde. LCMS (ESI) 476 (M+H) 1H NMR (400 MHz, DMSO-d6) δ ppm 11.52 (1H, br. s.) 10.28 (1H, s) 8.05 (1H, t, J=5.64 Hz) 8.01 (1H, d, J=5.42 Hz) 7.77 (1H, d, J=5.42 Hz) 7.58 (1H, dd, J=6.86, 2.17 Hz) 7.47 (1H, d, J=5.42 Hz) 7.25-7.39 (4H, m) 6.80 (1H, d, J=5.47 Hz) 6.42 (1H, dd, J=3.49, 1.93 Hz) 3.76 (2H, s) 3.33-3.42 (2H, m) 2.65 (2H, t, J=6.49 Hz)

IC$_{50}$ (p70S6K) "+++"

49. 3-(1H-Pyrrolo[2,3-b]pyridin-4-ylamino)-thiophene-2-carboxylic acid [2-(3-methoxy-benzylamino)-ethyl]-amide

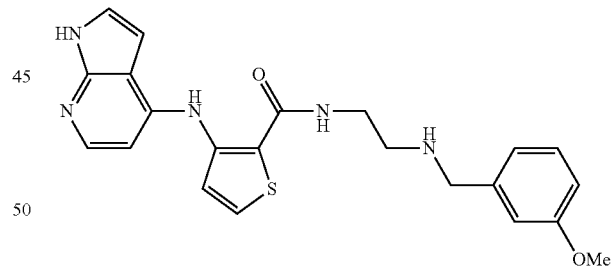

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-methoxybenzaldehyde instead of 4-methoxy benzaldehyde. LCMS (ESI) 422 (M+H) IC$_{50}$ (p70S6K) "+++"

50. 3-(1H-Pyrrolo[2,3-b]pyridin-4-ylamino)-thiophene-2-carboxylic acid [2-(3-trifluoromethoxy-benzylamino)-ethyl]-amide

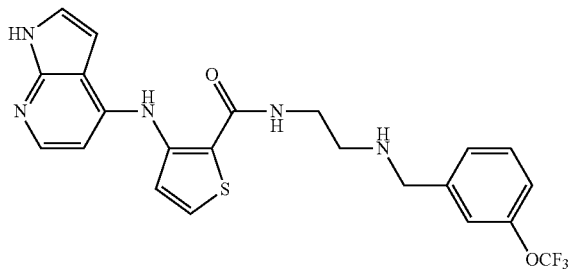 [SMILES: O=C(NCCNCc1cccc(OC(F)(F)F)c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-(trifluoromethoxy)benzaldehyde instead of 4-methoxy benzaldehyde. LCMS (ESI) 476 (M+H) 1H NMR (400 MHz, DMSO-d6) δ ppm 11.52 (1H, br. s.) 10.29 (1H, s) 8.04 (1H, t, J=5.56 Hz) 8.01 (1H, d, J=5.42 Hz) 7.77 (1H, dd, J=5.42, 0.15 Hz) 7.47 (1H, d, J=5.37 Hz) 7.39 (1H, d, J=7.76 Hz) 7.26-7.35 (3H, m) 7.18 (1H, d, J=7.96 Hz) 6.80 (1H, d, J=5.42 Hz) 6.42 (1H, dd, J=3.47, 1.90 Hz) 3.74 (2H, s) 3.35 (2H, q, J=6.35 Hz) 2.63 (2H, t, J=6.49 Hz)

IC$_{50}$ (p70S6K) "+++"

51. 3-(1H-Pyrrolo[2,3-b]pyridin-4-ylamino)-thiophene-2-carboxylic acid [2-(4-trifluoromethoxy-benzylamino)-ethyl]-amide

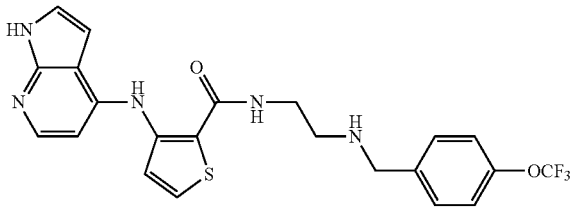 [SMILES: O=C(NCCNCc1ccc(OC(F)(F)F)cc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 4-(trifluoromethoxy)benzaldehyde instead of 4-methoxy benzaldehyde. LCMS (ESI) 476 (M+H) 1H NMR (400 MHz, DMSO-d6) δ ppm 11.52 (1H, br. s.) 10.25 (1H, s) 8.04 (1H, t, J=5.52 Hz) 8.01 (1H, d, J=5.42 Hz) 7.77 (1H, d, J=5.47 Hz) 7.46 (1H, d, J=5.42 Hz) 7.42 (2H, d, J=8.69 Hz) 7.29 (1H, d, J=2.54 Hz) 7.23 (2H, d, J=8.44 Hz) 6.79 (1H, d, J=5.42 Hz) 6.43 (1H, dd, J=3.47, 1.90 Hz) 3.70 (2H, s) 3.35 (2H, q, J=6.49 Hz) 2.63 (2H, t, J=6.52 Hz)

IC$_{50}$ (p70S6K) "+++"

52. 3-(1H-Pyrrolo[2,3-b]pyridin-4-ylamino)-thiophene-2-carboxylic acid [2-(4-trifluoromethyl-benzylamino)-ethyl]-amide

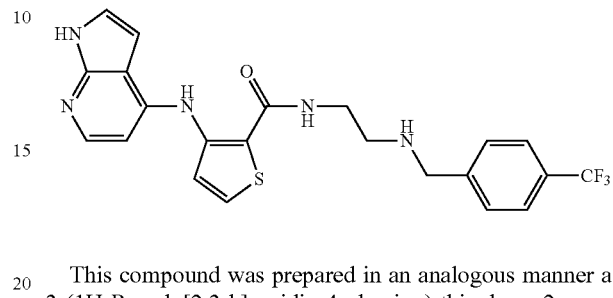

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 4-(trifluoromethyl)benzaldehyde lidine instead of 4-methoxy benzaldehyde. LCMS (ESI) 460 (M+H) 1H NMR (400 MHz, DMSO-d6) δ ppm 11.52 (1H, br. s.) 10.25 (1H, s) 8.05 (1H, t, J=5.66 Hz) 8.01 (1H, d, J=5.47 Hz) 7.77 (1H, d, J=5.27 Hz) 7.58-7.64 (2H, m) 7.50-7.55 (2H, m) 7.46 (1H, d, J=5.42 Hz) 7.30 (1H, d, J=3.17 Hz) 6.79 (1H, d, J=5.52 Hz) 6.43 (1H, dd, J=3.44, 1.93 Hz) 3.77 (2H, s) 3.35 (2H, q, J=6.23 Hz) 2.63 (2H, t, J=6.52 Hz)

IC$_{50}$ (p70S6K) "+++"

53. 3-(1H-Pyrrolo[2,3-b]pyridin-4-ylamino)-thiophene-2-carboxylic acid {2-[(furan-3-ylmethyl)-amino]-ethyl}-amide

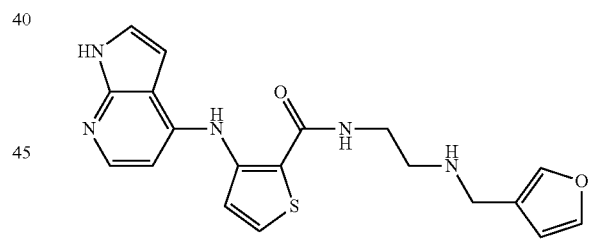

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-furaldehyde instead of 4-methoxy benzaldehyde. LCMS (ESI) 382 (M+H) 1H NMR (400 MHz, DMSO-d6) δ ppm 11.49 (1H, br. s.) 10.25 (1H, s) 7.93-8.05 (2H, m) 7.75 (1H, d, J=5.37 Hz) 7.52 (1H, t, J=1.61 Hz) 7.46 (1H, d, J=0.68 Hz) 7.44 (1H, d, J=5.42 Hz) 7.28 (1H, dd, J=3.20, 2.66 Hz) 6.77 (1H, d, J=5.42 Hz) 6.38-6.43 (2H, m) 3.49 (2H, s) 3.30-3.35 (2H, m) 2.60 (2H, t, J=6.49 Hz)

IC$_{50}$ (p70S6K) "+++"

54. 3-(1H-Pyrrolo[2,3-b]pyridin-4-ylamino)-thiophene-2-carboxylic acid {2-[(1H-pyrrol-2-ylmethyl)-amino]-ethyl}-amide

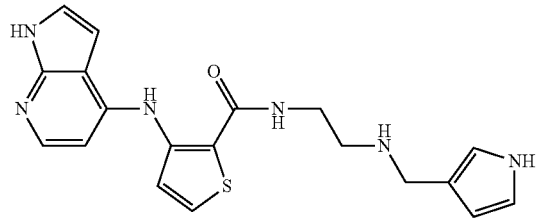 [SMILES: O=C(NCCNCc1cc[nH]c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using pyrrol-2-carboxaldehyde instead of 4-methoxy benzaldehyde. LCMS (ESI) 379 (M+H) 1H NMR (400 MHz, DMSO-d6) δ ppm 11.52 (1H, br. s.) 10.54 (1H, br. s.) 10.31 (1H, s) 8.00-8.07 (2H, m) 7.77 (1H, d, J=5.42 Hz) 7.47 (1H, d, J=5.47 Hz) 7.31 (1H, dd, J=3.22, 2.59 Hz) 6.81 (1H, d, J=5.42 Hz) 6.57-6.62 (1H, m) 6.43 (1H, dd, J=3.44, 1.88 Hz) 5.88 (1H, q, J=2.64 Hz) 5.82-5.86 (1H, m) 3.61 (2H, s) 2.63 (2H, t, J=6.47 Hz)

IC$_{50}$ (p70S6K) "+++"

55. 3-(1H-Pyrrolo[2,3-b]pyridin-4-ylamino)-thiophene-2-carboxylic acid {2-[bis-(3-methyl-benzyl)-amino]-ethyl}-amide

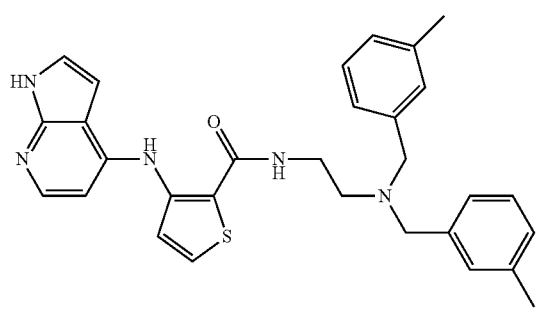 [SMILES: Cc1cccc(CN(CCNC(=O)c2sccc2Nc2ccnc3[nH]ccc23)Cc2cccc(C)c2)c1]

This compound was prepared in an analogous manner as 3-(1H-Pyrrolo[2,3-b]pyridin-4-ylamino)-thiophene-2-carboxylic acid [2-(4-methoxy-benzylamino)-ethyl]-amide using 3-methylbenzaldehyde instead of 4-methoxy benzaldehyde. LCMS (ESI) 510 (M+H) $^1$H NMR (400 MHz, DMSO-d$_6$) δ ppm 11.45-11.54 (1H, m) 10.33 (1H, s) 8.00 (1H, d, J=5.27 Hz) 7.87 (1H, t, J=5.66 Hz) 7.77 (1H, d, J=5.47 Hz) 7.48 (1H, d, J=5.47 Hz) 7.23-7.32 (1H, m) 7.05-7.16 (2H, m) 6.95 (1H, d, J=6.25 Hz) 6.82 (1H, d, J=5.47 Hz) 6.37 (1H, dd, J=3.51, 1.95 Hz) 3.50 (4H, s) 3.34-3.43 (1H, m) 2.51 (1H, t, J=6.54 Hz) 2.18 (2H, s)

IC$_{50}$ (p70S6K) "++"

56. 3-(1H-Pyrrolo[2,3-b]pyridin-4-ylamino)-thiophene-2-carboxylic acid [2-(3-methyl-benzylamino)-ethyl]-amide

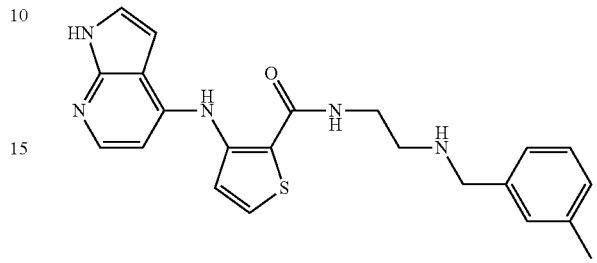

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-methylbenzaldehyde instead of 4-methoxy benzaldehyde. LCMS (ESI) 406 (M+H) $^1$H NMR (400 MHz, DMSO-d$_6$) δ ppm 11.49 (1H, br. s.) 10.26 (1H, s) 7.96-8.06 (1H, m) 7.75 (1H, d, J=5.47 Hz) 7.44 (1H, d, J=5.27 Hz) 7.25-7.32 (1H, m) 6.93-7.17 (2H, m) 6.78 (1H, d, J=5.47 Hz) 6.41 (1H, dd, J=3.51, 1.76 Hz) 3.61 (2H, s) 3.31-3.36 (2H, m) 2.60 (2H, t, J=6.54 Hz) 2.22 (3H, s)

IC$_{50}$ (p70S6K) "+++"

57. 3-(1H-Pyrrolo[2,3-b]pyridin-4-ylamino)-thiophene-2-carboxylic acid [2-(3-chloro-benzylamino)-ethyl]-amide

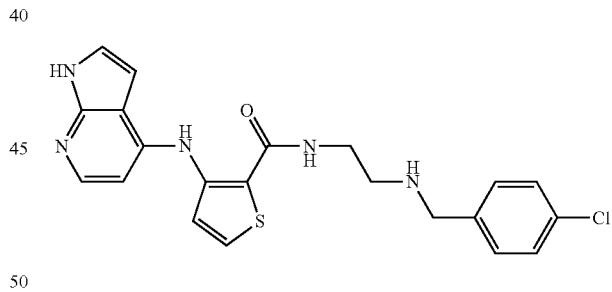

This compound was prepared in an analogous manner as 3-(1H-Pyrrolo[2,3-b]pyridin-4-ylamino)-thiophene-2-carboxylic acid [2-(4-methoxy-benzylamino)-ethyl]-amide using 3-chlorobenzaldehyde instead of 4-methoxy benzaldehyde. LCMS (ESI) 426 (M+H) $^1$H NMR (400 MHz, DMSO-d$_6$) δ ppm 11.50 (1H, br. s.) 10.43 (1H, s) 10.26 (1H, s) 7.94-8.11 (1H, m) 7.72-7.80 (1H, m) 7.37-7.52 (1H, m) 7.18-7.33 (1H, m) 7.05-7.14 (1H, m) 6.75-6.85 (1H, m) 6.36-6.44 (1H, m) 3.70 (2H, s) 3.31-3.38 (2H, m) 2.62 (2H, t, J=6.44 Hz)

IC$_{50}$ (p70S6K) "+++"

58. 3-(1H-Pyrrolo[2,3-b]pyridin-4-ylamino)-thiophene-2-carboxylic acid [2-(2-fluoro-benzylamino)-ethyl]-amide

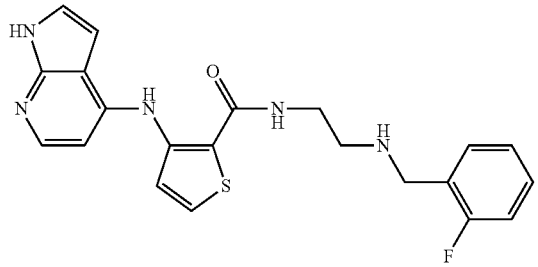 [SMILES: O=C(NCCNCc1ccccc1F)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 2-fluorobenzaldehyde instead of 4-methoxy benzaldehyde. LCMS (ESI) 410 (M+H) $^1$H NMR (400 MHz, DMSO-d$_6$) δ ppm 11.46-11.56 (1H, m) 10.26 (1H, s) 8.03 (1H, t, J=5.56 Hz) 7.99 (1H, d, J=5.47 Hz) 7.75 (1H, d, J=5.47 Hz) 7.44 (1H, d, J=5.47 Hz) 7.37-7.42 (1H, m) 7.26-7.30 (1H, m) 7.19-7.26 (1H, m) 7.05-7.12 (1H, m) 6.78 (1H, d, J=5.47 Hz) 6.40 (1H, dd, J=3.61, 1.66 Hz) 3.70 (2H, s) 3.32-3.37 (2H, m) 2.62 (2H, t, J=6.54 Hz)

IC$_{50}$ (p70S6K) "+++"

59. 3-(1H-Pyrrolo[2,3-b]pyridin-4-ylamino)-thiophene-2-carboxylic acid {2-[(1H-indol-5-ylmethyl)-amino]-ethyl}-amide

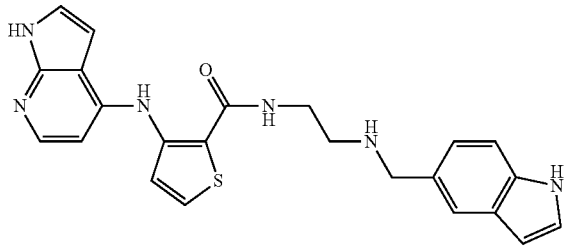 [SMILES: O=C(NCCNCc1ccc2[nH]ccc2c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using indole-5-carboxaldehyde instead of 4-methoxy benzaldehyde. LCMS (ESI) 431 (M+H) $^1$H NMR (400 MHz, DMSO-d$_6$) δ ppm 11.49 (1H, br. s.) 10.93 (1H, br. s.) 10.27 (1H, s) 7.96-8.06 (1H, m) 7.75 (1H, d, J=5.47 Hz) 7.41-7.51 (1H, m) 7.22-7.31 (1H, m) 7.02 (1H, dd, J=8.30, 1.46 Hz) 6.78 (1H, d, J=5.47 Hz) 6.41 (1H, dd, J=3.51, 1.76 Hz) 6.30 (1H, dd, J=2.54, 1.56 Hz) 3.73 (2H, s) 3.33 (2H, d, J=5.86 Hz) 2.64 (2H, t, J=6.25 Hz)

IC$_{50}$ (p70S6K) "+++"

60. 3-(1H-Pyrrolo[2,3-b]pyridin-4-ylamino)-thiophene-2-carboxylic acid [2-(2-methoxy-benzylamino)-ethyl]-amide

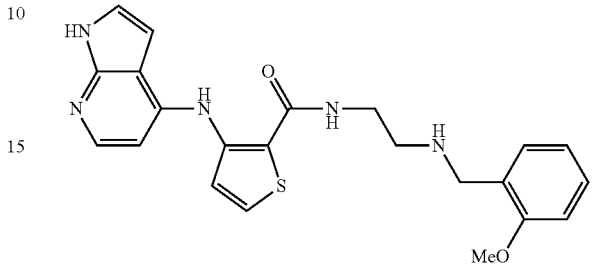

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 2-methoxybenzaldehyde instead of 4-methoxy benzaldehyde. LCMS (ESI) 422 (M+H) $^1$H NMR (400 MHz, DMSO-d$_6$) δ ppm 11.50 (1H, br. s.) 10.27 (1H, s) 8.04 (1H, t, J=5.56 Hz) 7.99 (1H, d, J=5.47 Hz) 7.75 (1H, d, J=5.47 Hz) 7.45 (1H, d, J=5.27 Hz) 7.23-7.32 (2H, m) 7.13-7.21 (1H, m) 6.91 (1H, d, J=8.00 Hz) 6.81-6.87 (1H, m) 6.79 (1H, d, J=5.47 Hz) 6.40 (1H, dd, J=3.51, 1.76 Hz) 3.72 (3H, s) 3.67 (2H, s) 3.34 (2H, q, J=6.31 Hz) 2.65 (2H, t, J=6.35 Hz)

IC$_{50}$ (p70S6K) "+++"

61. 3-(1H-Pyrrolo[2,3-b]pyridin-4-ylamino)-thiophene-2-carboxylic acid {2-[(pyridin-3-ylmethyl)-amino]-ethyl}-amide

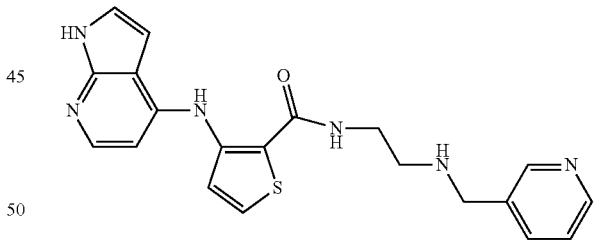

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-pyridinecarboxaldehyde instead of 4-methoxy benzaldehyde. LCMS (ESI) 393 (M+H) 1H NMR (400 MHz, METHANOL-d4) δ ppm 8.51 (1H, d, J=2.20 Hz) 8.39 (1H, dd, J=4.91, 1.54 Hz) 8.00 (1H, d, J=5.66 Hz) 7.80 (1H, dt, J=7.83, 1.87 Hz) 7.64 (1H, d, J=5.42 Hz) 7.47 (1H, d, J=5.47 Hz) 7.33 (1H, dd, J=7.83, 4.91 Hz) 7.24 (1H, d, J=3.56 Hz) 6.87 (1H, d, J=5.66 Hz) 6.55 (1H, d, J=3.56 Hz) 3.80 (2H, s) 3.51 (2H, t, J=6.30 Hz) 2.79 (2H, t, J=6.22 Hz)

IC₅₀ (p70S6K) "++"

62. 3-(1H-Pyrrolo[2,3-b]pyridin-4-ylamino)-thiophene-2-carboxylic acid [2-(4-fluoro-benzylamino)-ethyl]-amide

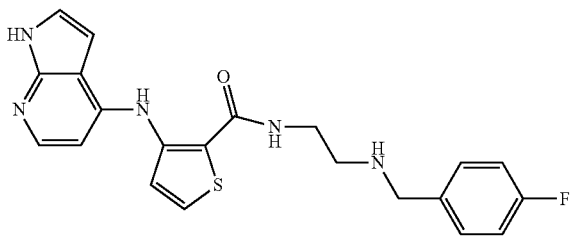

This compound was prepared in an analogous manner as 3-(1H-Pyrrolo[2,3-b]pyridin-4-ylamino)-thiophene-2-carboxylic acid [2-(4-methoxy-benzylamino)-ethyl]-amide using 4-fluorobenzaldehyde instead of 4-methoxy benzaldehyde. LCMS (ESI) 410 (M+H) 1H NMR (400 MHz, DMSO-d6) δ ppm 11.52 (1H, br. s.) 10.25 (1H, s) 7.99-8.07 (2H, m) 7.77 (1H, d, J=5.42 Hz) 7.46 (1H, d, J=5.42 Hz) 7.31 (3H, dt, J=5.72, 2.82 Hz) 7.06 (2H, t, J=8.91 Hz) 6.79 (1H, d, J=5.42 Hz) 6.43 (1H, dd, J=3.47, 1.95 Hz) 3.65 (2H, s) 3.34 (2H, d, J=5.86 Hz) 2.62 (2H, t, J=6.49 Hz)

IC₅₀ (p70S6K) "+++"

63. 3-(1H-Pyrrolo[2,3-b]pyridin-4-ylamino)-thiophene-2-carboxylic acid [2-(3-chloro-4-fluoro-benzylamino)-ethyl]-amide

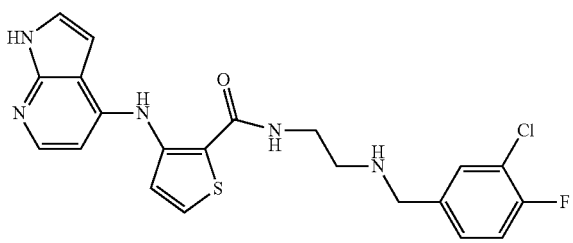 [SMILES: O=C(NCCNCc1ccc(F)c(Cl)c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-chloro-4-fluorobenzaldehyde instead of 4-methoxy benzaldehyde. LCMS (ESI) 444 (M+H) 1H NMR (400 MHz, DMSO-d6) δ ppm 11.52 (1H, br. s.) 10.27 (1H, s) 7.99-8.07 (2H, m) 7.77 (1H, d, J=5.47 Hz) 7.52 (1H, d, J=7.91 Hz) 7.46 (1H, d, J=5.42 Hz) 7.29 (3H, dd, J=1.24, 0.17 Hz) 6.80 (1H, d, J=5.47 Hz) 6.42 (1H, dd, J=3.47, 1.85 Hz) 3.66 (2H, s) 2.61 (2H, t, J=6.59 Hz)

IC₅₀ (p70S6K) "+++"

64. (4-Amino-piperidin-1-yl)-[3-(1H-pyrrolo[2,3-b]pyridin-4-ylamino)-thiophen-2-yl]-methanone

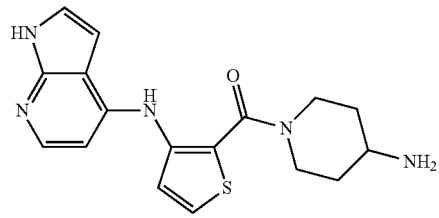 [SMILES: NC1CCN(C(=O)c2sccc2Nc2ccnc3[nH]ccc23)CC1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 4-Boc-aminopiperidine instead of 1-BOC-3-aminopyrrolidine. LCMS (ESI) 342 (M+H) 1H NMR (400 MHz, DMSO-d6) δ ppm 12.52 (1H, s) 10.36 (1H, s) 8.18 (1H, d, J=4.10 Hz) 8.04 (1H, d, J=7.03 Hz) 7.87 (1H, d, J=5.08 Hz) 7.33-7.37 (1H, m) 7.15 (1H, d, J=5.27 Hz) 6.53 (1H, d, J=7.03 Hz) 3.54 (4H, s) 2.81-2.94 (1H, m) 1.82 (2H, d, J=9.96 Hz) 1.70-1.76 (1H, m) 1.25-1.39 (2H, m)

IC₅₀ (p70S6K) "+"

65. (4-Benzylamino-piperidin-1-yl)-[3-(1H-pyrrolo[2,3-b]pyridin-4-ylamino)-thiophen-2-yl]-methanone

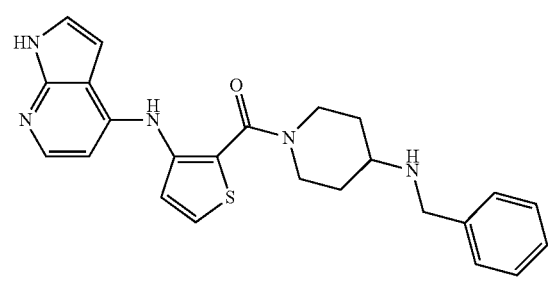 [SMILES: O=C(c1sccc1Nc1ccnc2[nH]ccc12)N1CCC(NCc2ccccc2)CC1]

This compound was prepared in an analogous manner as 3-(1H-Pyrrolo[2,3-b]pyridin-4-ylamino)-thiophene-2-carboxylic acid [2-(4-methoxy-benzylamino)-ethyl]-amide using (4-Amino-piperidin-1-yl)-[3-(1H-pyrrolo[2,3-b]pyridin-4-ylamino)-thiophen-2-yl]-methanone instead of 3-(1H-Pyrrolo[2,3-b]pyridin-4-ylamino)-thiophene-2-carboxylic acid (2-amino-ethyl)-amide and benzaldehyde instead of 4-methoxy benzaldehyde. LCMS (ESI) 432 1H NMR (400 MHz, DMSO-d6) δ ppm 11.33 (1H, s) 8.93 (1H, s) 7.86 (1H, d, J=5.27 Hz) 7.70 (1H, d, J=5.27 Hz) 7.20-7.27 (3H, m) 7.11-7.19 (2H, m) 6.53 (1H, dd, J=3.51, 1.95 Hz) 6.43 (1H, d, J=5.47 Hz) 3.90 (2H, d, J=13.08 Hz) 3.57 (2H, s) 2.91 (2H, t, J=10.84 Hz) 1.63 (2H, d, J=10.35 Hz) 1.04-1.15 (2H, m)

IC$_{50}$ (p70S6K) "+"

66. 3-(1H-Pyrrolo[2,3-b]pyridin-4-ylamino)-thiophene-2-carboxylic acid (2-benzylsulfanyl-ethyl)-amide

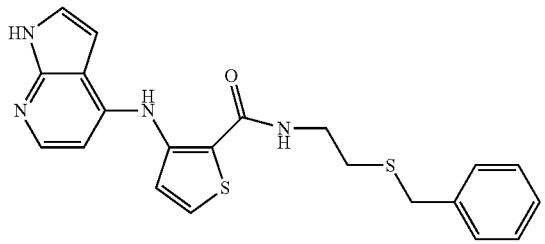

This compound was prepared in an analogous manner as 3-(1H-Pyrrolo[2,3-b]pyridin-4-ylamino)-thiophene-2-carboxylic acid (2-amino-ethyl)-amide using 2-(benzylsulfanyl) ethanamine instead of tert-butyl-2-amino ethyl carbamate. LCMS (ESI) 409 (M+H) $^1$H NMR (400 MHz, DMSO-d$_6$) δ ppm 11.52 (1H, br. s.) 10.33-10.38 (1H, m) 8.22 (1H, t, J=5.66 Hz) 8.00 (1H, d, J=5.47 Hz) 7.76 (1H, d, J=5.47 Hz) 7.45-7.51 (1H, m) 7.15-7.36 (5H, m) 6.82 (1H, d, J=5.47 Hz) 6.43 (1H, dd, J=3.42, 1.85 Hz) 3.75 (2H, s) 3.35-3.47 (2H, m) 2.51-2.58 (2H, m)

IC$_{50}$ (p70S6K) "++"

67. 3-(1H-Pyrrolo[2,3-b]pyridin-4-ylamino)-thiophene-2-carboxylic acid (3-amino-propyl)-amide

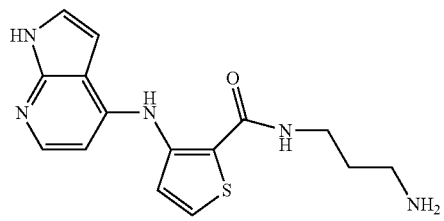 [SMILES: NCCCNC(=O)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using 3-(Boc-amino)-propylamine instead of tert-butyl-2-amino ethyl carbamate. LCMS (ESI) 316 (M+H) $^1$H NMR (400 MHz, DMSO-d$_6$) δ ppm 12.47 (1H, br. s.) 10.84 (1H, s) 8.66 (1H, t, J=5.56 Hz) 8.04 (1H, d, J=6.83 Hz) 7.87 (3H, d, J=5.27 Hz) 7.36-7.42 (1H, m) 7.30 (1H, d, J=5.27 Hz) 6.81 (1H, br. s.) 6.67 (1H, d, J=7.03 Hz) 3.23 (2H, q, J=6.44 Hz) 2.66-2.82 (2H, m) 1.67-1.81 (2H, m)

IC$_{50}$ (p70S6K) "++"

68. 3-(1H-Pyrrolo[2,3-b]pyridin-4-ylamino)-thiophene-2-carboxylic acid (2-benzyloxy-ethyl)-amide

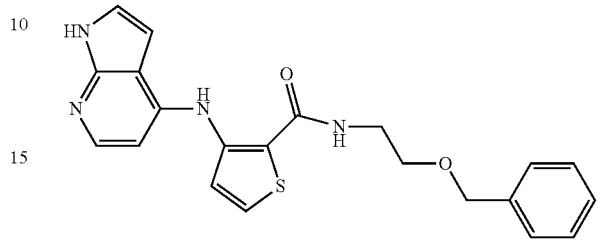

This compound was prepared in an analogous manner as 3-(1H-Pyrrolo[2,3-b]pyridin-4-ylamino)-thiophene-2-carboxylic acid (2-amino-ethyl)-amide using 2-(benzyloxy) ethanamine instead of tert-butyl-2-amino ethyl carbamate. LCMS (ESI) 393 (M+H) $^1$H NMR (400 MHz, DMSO-d$_6$) δ ppm 11.51 (1H, br. s.) 10.24 (1H, s) 8.15 (1H, s) 7.99 (1H, d, J=5.47 Hz) 7.76 (1H, d, J=5.27 Hz) 7.44 (1H, d, J=5.47 Hz) 7.16-7.32 (5H, m) 6.78 (1H, d, J=5.27 Hz) 6.41 (1H, d, J=3.32 Hz) 4.44 (2H, s) 3.48-3.56 (2H, m) 3.39-3.47 (2H, m)

IC$_{50}$ (p70S6K) "+++"

69. 3-(1H-Pyrrolo[2,3-b]pyridin-4-ylamino)-thiophene-2-carboxylic acid (2-phenylmethanesulfonyl-ethyl)-amide

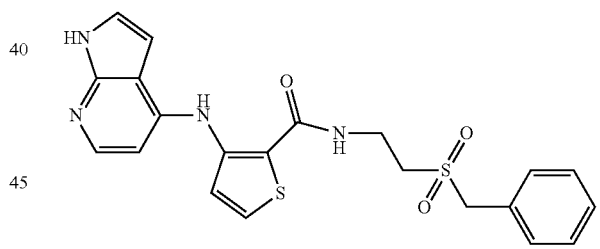

To a solution of 3-(1H-Pyrrolo[2,3-b]pyridin-4-ylamino)-thiophene-2-carboxylic acid (2-benzylsulfanyl-ethyl)-amide (50 mg, 0.12 mmol) in chloroform (1.0 mL) was added m-chloroperbenzoic acid (82 mg, 0.37 mmol) and stirred at room temperature for 1H. Aqueous sodium bicarbonate (saturated) was added to the solution. The layers were separated and the aqueous layer was extracted (2×) with methylene chloride. After concentration the residue was purified by ISCO Companion (silica, 0-10% methanol, methylene chloride, 1% ammonium hydroxide) to provide 3-(1H-Pyrrolo[2,3-b]pyridin-4-ylamino)-thiophene-2-carboxylic acid (2-phenylmethanesulfonyl-ethyl)-amide (54 mg, 31%). LCMS (ESI) 441 (M+H) $^1$H NMR (400 MHz, DMSO-d$_6$) δ ppm 11.53 (1H, br. s.) 10.26 (1H, s) 8.31 (1H, t, J=5.86 Hz) 8.01 (1H, d, J=5.27 Hz) 7.78 (1H, d, J=5.27 Hz) 7.47 (1H, d, J=5.47 Hz) 7.27-7.43 (4H, m) 6.83 (1H, d, J=5.47 Hz) 6.42 (1H, dd, J=3.51, 1.95 Hz) 4.52 (2H, s) 3.59-3.68 (2H, m) 3.23-3.29 (2H, m)

IC$_{50}$ (p70S6K) "++"

70. 3-(1H-Pyrrolo[2,3-b]pyridin-4-ylamino)-thiophene-2-carboxylic acid (2-benzoylamino-ethyl)-amide

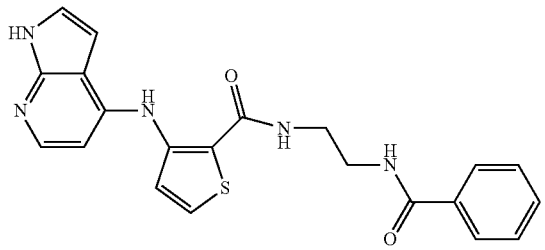 [SMILES: O=C(NCCNC(=O)c1sccc1Nc1ccnc2[nH]ccc12)c1ccccc1]

To a solution of 3-(1H-Pyrrolo[2,3-b]pyridin-4-ylamino)-thiophene-2-carboxylic acid (2-amino-ethyl)-amide (40 mg, 0.12 mmol) and diisopropylethylamine (0.1 mL, 0.59 mmol) in methylene chloride (1.0 mL) was added benzoyl chloride (15 uL, 0.13 mmol) and stirred at room temperature for 30 min. The crude reaction was purified by ISCO Companion (silica, (silica, 0-5% methanol, methylene chloride, 1% ammonium hydroxide) to afford 3-(1H-Pyrrolo[2,3-b]pyridin-4-ylamino)-thiophene-2-carboxylic acid (2-benzoylamino-ethyl)-amide (48 mg, 48%). LCMS (ESI) 406 (M+H) $^1$H NMR (400 MHz, DMSO-d$_6$) δ ppm 11.51 (1H, br. s.) 10.36 (1H, s) 8.55 (1H, s) 8.24 (1H, br. s.) 8.00 (1H, d, J=5.27 Hz) 7.73-7.85 (3H, m) 7.43-7.52 (2H, m) 7.35-7.42 (2H, m) 7.28 (1H, d, J=3.32 Hz) 6.82 (1H, d, J=5.47 Hz) 6.40 (1H, d, J=3.51 Hz) 3.39-3.45 (4H, m)

IC$_{50}$ (p70S6K) "+++"

71. 3-(1H-Pyrrolo[2,3-b]pyridin-4-ylamino)-thiophene-2-carboxylic acid (2-benzenesulfonylamino-ethyl)-amide

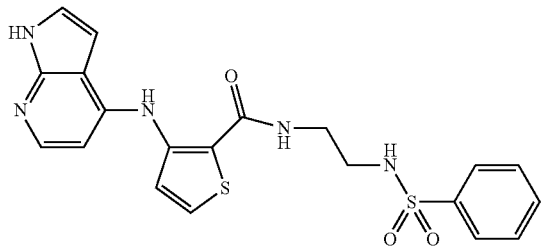 [SMILES: O=C(NCCNS(=O)(=O)c1ccccc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using benzenesulfonyl chloride instead of benzoyl chloride. LCMS (ESI) 442 (M+H) $^1$H NMR (400 MHz, DMSO-d$_6$) δ ppm 11.51 (1H, br. s.) 10.25 (1H, s) 8.05 (1H, t, J=5.76 Hz) 8.00 (1H, d, J=5.47 Hz) 7.70-7.81 (4H, m) 7.49-7.62 (3H, m) 7.45 (1H, d, J=5.47 Hz) 7.25-7.32 (1H, m) 6.81 (1H, d, J=5.47 Hz) 6.39 (1H, dd, J=3.42, 1.85 Hz) 3.21-3.28 (2H, m) 2.82-2.93 (2H, m)

IC$_{50}$ (p70S6K) "++"

72. 2-(1H-Pyrrolo[2,3-b]pyridin-4-ylamino)-thiophene-3-carboxylic acid (2-benzylamino-ethyl)-amide

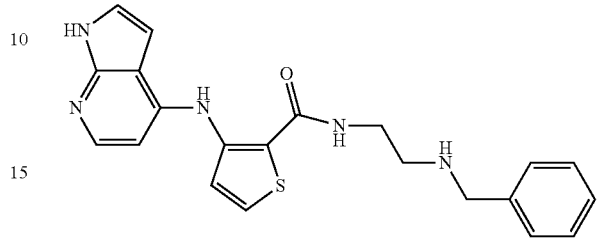

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-benzylethylenediamine instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 392 (M+H) 1H NMR (400 MHz, DMSO-d6) δ ppm 11.95 (1H, br. s.) 11.66 (1H, br. s.) 8.27 (1H, t, J=5.73 Hz) 8.15 (1H, d, J=5.52 Hz) 7.48 (1H, d, J=5.86 Hz) 7.25-7.39 (6H, m) 7.15-7.24 (1H, m) 6.98 (1H, d, J=5.47 Hz) 6.92 (1H, d, J=0.10 Hz) 6.46 (1H, dd, J=3.42, 1.76 Hz) 3.73 (2H, s) 3.41 (2H, q, J=6.44 Hz) 2.68 (2H, t, J=6.56 Hz)

IC$_{50}$ (p70S6K) "+++"

73. 3-(1H-Pyrrolo[2,3-b]pyridin-4-ylamino)-thiophene-2-carboxylic acid (benzylcarbamoyl-methyl)-amide

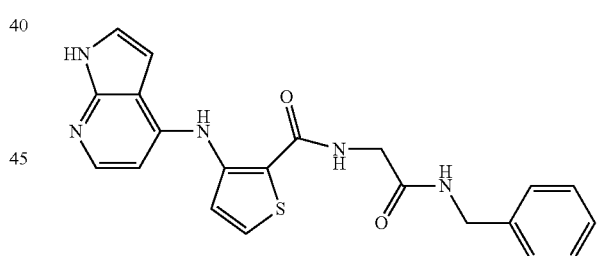

To a solution of methyl ({[3-(1H-pyrrolo[2,3-b]pyridin-4-ylamino)thiophen-2-yl]carbonyl}amino)acetate (50 mg, 0.15 mmol) in tetrahydrofuran (2 mL) was added a pre-mixed solution of benzylamine (25 uL, 0.23 mmol) and trimethylaluminum (2.0 M toluene, 91 uL, 0.18 mmol). The solution was stirred at room temperature for 10 minutes then water was added resulting in precipitation. The precipitate was collected by filtration and dried under vacuum to afford 3-(1H-Pyrrolo[2,3-b]pyridin-4-ylamino)-thiophene-2-carboxylic acid (benzylcarbamoyl-methyl)-amide (55 mg, 90%) (ESI) 406 (M+H) 1H NMR (400 MHz, DMSO-d6) δ ppm 11.54 (1H, br. s.) 10.31 (1H, s) 8.46 (1H, t, J=6.08 Hz) 8.39 (1H, t, J=5.69 Hz) 8.03 (1H, d, J=5.37 Hz) 7.81 (1H, d, J=5.42 Hz) 7.51 (1H, d, J=5.42 Hz) 7.33 (1H, dd, J=3.20, 2.71 Hz) 7.28 (4H, d, J=0.05 Hz) 7.16-7.25 (1H, m) 6.85 (1H, d, J=5.47 Hz) 6.44 (1H, dd, J=3.47, 1.90 Hz) 4.30 (2H, d, J=5.95 Hz) 3.89 (2H, d, J=5.71 Hz)

IC$_{50}$ (p70S6K) "++"

74. 3-(1H-Pyrrolo[2,3-b]pyridin-4-ylamino)-thiophene-2-carboxylic acid {2-[(pyridin-4-ylmethyl)-amino]-ethyl}-amide

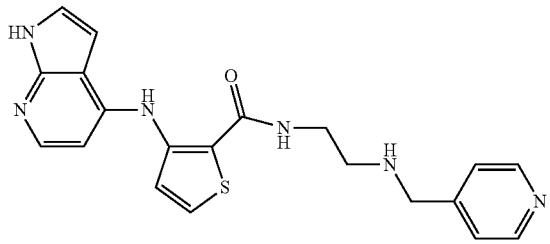 [SMILES: O=C(NCCNCc1ccncc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 4-pyridinecaboxaldehyde instead of 4-methoxy benzaldehyde. LCMS (ESI) 393 (M+H) 1H NMR (400 MHz, METHANOL-d4) δ ppm 8.35-8.42 (2H, m) 8.00 (1H, d, J=5.61 Hz) 7.65 (1H, d, J=5.42 Hz) 7.46 (1H, d, J=5.47 Hz) 7.36-7.41 (2H, m) 7.24 (1H, d, J=3.56 Hz) 6.86 (1H, d, J=5.66 Hz) 6.55 (1H, d, J=3.56 Hz) 3.82 (2H, s) 3.51 (2H, t, J=6.25 Hz) 2.79 (2H, t, J=6.17 Hz)

IC$_{50}$ (p70S6K) "++"

75. 2-(1H-Pyrrolo[2,3-b]pyridin-4-ylamino)-thiophene-3-carboxylic acid ((S)-2-hydroxy-1-phenyl-ethyl)-amide

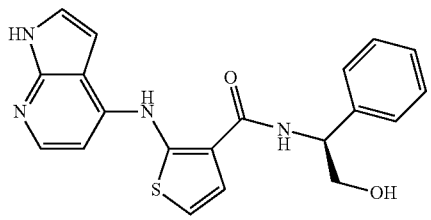 [SMILES: O=C(N[C@H](CO)c1ccccc1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-2-phenylglycinol instead of 1-BOC-3-aminopyrrolidine. LCMS (ESI) 379 (M+H) 1H NMR (400 MHz, DMSO-d6) δ ppm 11.82 (1H, s) 11.65 (1H, br. s.) 8.48 (1H, d, J=8.25 Hz) 8.14 (1H, d, J=5.47 Hz) 7.70 (1H, d, J=5.86 Hz) 7.38-7.44 (2H, m) 7.29-7.37 (3H, m) 7.19-7.27 (1H, m) 6.97 (2H, dd, J=5.64, 1.68 Hz) 6.41 (1H, dd, J=3.44, 1.93 Hz) 5.17 (1H, td, J=8.04, 5.78 Hz) 4.97 (1H, t, J=5.81 Hz) 3.62-3.79 (2H, m, J=11.74, 5.78, 5.78, 5.78, 5.78 Hz)

IC$_{50}$ (p70S6K) "+++"

76. 3-(1H-Pyrrolo[2,3-b]pyridin-4-ylamino)-thiophene-2-carboxylic acid (2-azido-1-phenyl-ethyl)-amide

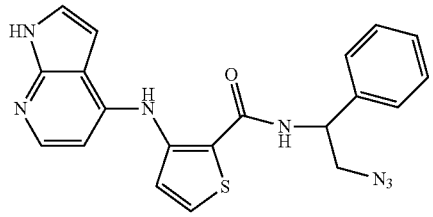 [SMILES: [N-]=[N+]=NCC(NC(=O)c1sccc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-azido-1-phenylethanamine ethyl ester instead of 1-BOC-3-aminopyrrolidine. LCMS (ESI) 404 (M+H) 1H NMR (400 MHz, DMSO-d6) δ ppm 11.53 (1H, br. s.) 10.22 (1H, s) 8.69 (1H, d, J=8.49 Hz) 8.02 (1H, d, J=5.42 Hz) 7.85 (1H, d, J=5.47 Hz) 7.49 (1H, d, J=5.42 Hz) 7.40-7.45 (2H, m) 7.22-7.38 (4H, m) 6.81 (1H, d, J=5.47 Hz) 6.41 (1H, dd, J=3.49, 1.93 Hz) 5.30 (1H, td, J=9.01, 4.88 Hz) 3.79 (1H, dd, J=12.45, 9.76 Hz) 3.60 (1H, dd, J=12.47, 5.05 Hz)

IC$_{50}$ (p70S6K) "+++"

77. 3-(1H-Pyrrolo[2,3-b]pyridin-4-ylamino)-thiophene-2-carboxylic acid (2-amino-1-phenyl-ethyl)-amide

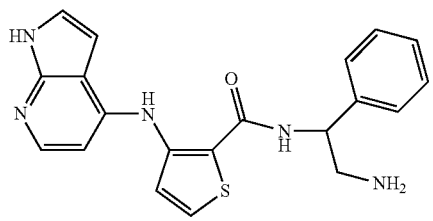 [SMILES: NCC(NC(=O)c1sccc1Nc1ccnc2[nH]ccc12)c1ccccc1]

A solution of 3-(1H-Pyrrolo[2,3-b]pyridin-4-ylamino)-thiophene-2-carboxylic acid (2-azido-1-phenyl-ethyl)-amide (120 mg, 0.27 mmol), 5% Pd/C (cat) in methanol (5 mL) was subjected to an atmosphere of hydrogen (balloon). After completion the solution was filtered and concentrated in vacuo. The residue was purified by ISCO Companion (silica, 10% methanol, methylene chloride, 1% ammonium hydroxide) to afford 3-(1H-Pyrrolo[2,3-b]pyridin-4-ylamino)-thiophene-2-carboxylic acid (2-amino-1-phenyl-ethyl)-amide (80 mg, 75%) (ESI) 378 (M+H) 1H NMR (400 MHz, DMSO-d6) δ ppm 11.51 (1H, br. s.) 8.00 (1H, d, J=5.47 Hz) 7.82 (1H, d, J=5.42 Hz) 7.45 (1H, d, J=5.42 Hz) 7.25-7.35 (5H, m) 7.16-7.24 (1H, m) 6.75 (1H, d, J=5.47 Hz) 6.39 (1H, d, J=3.12 Hz) 4.97 (1H, dd, J=8.03, 5.34 Hz) 2.85-2.94 (1H, m) 2.77-2.85 (1H, m)

IC$_{50}$ (p70S6K) "+++"

78. 3-(1H-Pyrrolo[2,3-b]pyridin-4-ylamino)-thiophene-2-carboxylic acid (2-amino-2-phenyl-ethyl)-amide

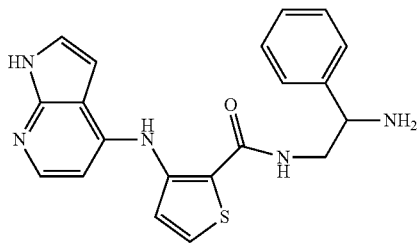 [SMILES: NC(CNC(=O)c1sccc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl (2-amino-1-phenylethyl)carbamate instead of 1-BOC-3-aminopyrrolidine. LCMS (ESI) 378 (M+H) 1H NMR (400 MHz, DMSO-d6) δ ppm 12.44 (1H, br. s.) 10.72 (1H, s) 8.67 (2H, d, J=4.10 Hz) 8.59 (1H, t, J=5.64 Hz) 8.05 (1H, d, J=6.78 Hz) 7.89 (1H, d, J=5.27 Hz) 7.40-7.50 (3H, m) 7.30 (1H, d, J=5.27 Hz) 7.26 (2H, d, J=2.68 Hz) 6.90 (1H, br. s.) 6.65 (1H, d, J=6.83 Hz) 4.40-4.55 (1H, m) 3.70-3.80 (1H, m) 3.58-3.68 (1H, m)

IC$_{50}$ (p70S6K) "+++"

79. 5-Methyl-3-(1H-pyrrolo[2,3-b]pyridin-4-ylamino)-thiophene-2-carboxylic acid (2-benzylamino-ethyl)-amide

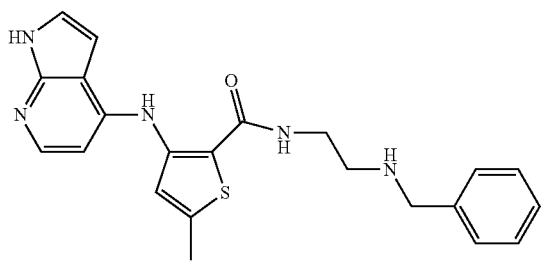 [SMILES: Cc1cc(Nc2ccnc3[nH]ccc23)c(C(=O)NCCNCc2ccccc2)s1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-benzylethylenediamine instead of 1-BOC-3-aminopyrrolidine and 5-Methyl-3-(1H-pyrrolo[2,3-b]pyridin-4-ylamino)-thiophene-2-carboxylic acid instead of 3-(1H-Pyrrolo[2,3-b]pyridin-4-ylamino)-thiophene-2-carboxylic acid. LCMS (ESI) 406 (M+H) 1H NMR (400 MHz, DMSO-d6) δ ppm 11.53 (1H, br. s.) 10.39 (1H, s) 8.02 (1H, d, J=5.42 Hz) 7.87 (1H, t, J=5.54 Hz) 7.26-7.36 (7H, m) 7.18-7.26 (1H, m) 6.83 (1H, d, J=5.47 Hz) 6.42 (1H, dd, J=3.47, 1.85 Hz) 3.76 (2H, s) 3.36 (2H, q, J=6.30 Hz) 2.69 (2H, t, J=6.39 Hz)

IC$_{50}$ (p70S6K) "+"

80. 5-Methyl-3-(1H-pyrrolo[2,3-b]pyridin-4-ylamino)-thiophene-2-carboxylicacid ((S)-2-hydroxy-1-phenyl-ethyl)-amide

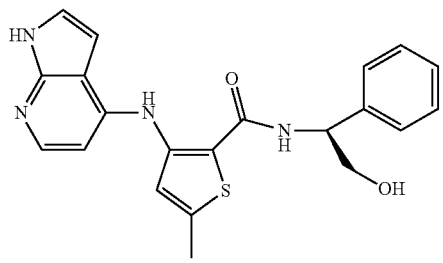 [SMILES: Cc1cc(Nc2ccnc3[nH]ccc23)c(C(=O)N[C@H](CO)c2ccccc2)s1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-2-phenylglycinol instead of 1-BOC-3-aminopyrrolidine and 5-Methyl-3-(1H-pyrrolo[2,3-b]pyridin-4-ylamino)-thiophene-2-carboxylic acid of 3-(1H-Pyrrolo[2,3-b]pyridin-4-ylamino)-thiophene-2-carboxylic acid. LCMS (ESI) 393 (M+H) 1H NMR (400 MHz, DMSO-d6) δ ppm 11.51 (1H, br. s.) 10.26 (1H, s) 8.12 (1H, d, J=8.05 Hz) 8.01 (1H, d, J=5.42 Hz) 7.31-7.38 (2H, m) 7.25-7.31 (4H, m) 7.17-7.24 (1H, m) 6.79 (1H, d, J=5.47 Hz) 6.39 (1H, dd, J=3.54, 1.98 Hz) 5.07 (1H, td, J=7.71, 5.76 Hz) 4.90 (1H, t, J=5.76 Hz) 3.56-3.74 (2H, m, J=11.13, 11.13, 10.97, 5.76 Hz) 2.52 (3H, d, J=1.07 Hz)

IC$_{50}$ (p70S6K) "++"

81. 3-(1H-Pyrrolo[2,3-b]pyridin-4-ylamino)-thiophene-2-carboxylic acid ((R)-1-benzyl-2-hydroxy-ethyl)-amide

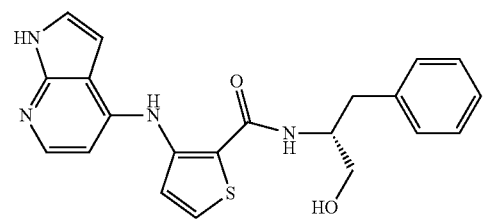 [SMILES: O=C(N[C@@H](CO)Cc1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (R)-phenylalaninol instead of 1-BOC-3-aminopyrrolidine. LCMS (ESI) 392 (M+H) 1H NMR (400 MHz, DMSO-d6) δ ppm 11.54 (1H, br. s.) 10.14 (1H, s) 7.98 (1H, d, J=5.47 Hz) 7.72-7.82 (2H, m) 7.40 (1H, d, J=5.37 Hz) 7.28 (1H, dd, J=3.54, 2.22 Hz) 7.14-7.22 (4H, m) 7.10 (1H, ddd, J=6.20, 2.98, 2.73 Hz) 6.73 (1H, d, J=5.52 Hz) 6.39 (1H, dd, J=3.51, 1.66 Hz) 4.82 (1H, t, J=5.56 Hz) 4.13 (1H, ddd, J=14.04, 5.58, 2.98 Hz) 3.42-3.49 (1H, m) 3.38 (1H, t, J=5.78 Hz) 2.84-2.93 (1H, m) 2.73 (1H, dd, J=13.67, 8.93 Hz)

IC$_{50}$ (p70S6K) "+"

82. 3-(1H-Pyrrolo[2,3-b]pyridin-4-ylamino)-benzo[b]thiophene-2-carboxylic acid (2-benzylamino-ethyl)-amide

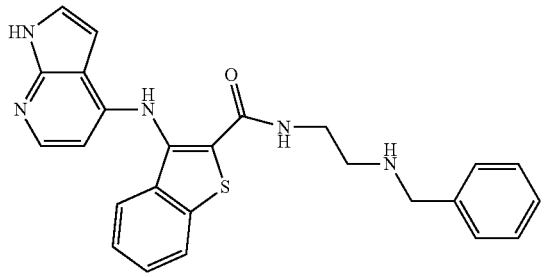 [SMILES: O=C(NCCNCc1ccccc1)c1sc2ccccc2c1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using N-benzylethylenediamine instead of 1-BOC-3-aminopyrrolidine and 3-(1H-Pyrrolo[2,3-b]pyridin-4-ylamino)-benzo[b]thiophene-2-carboxylic acid instead of 3-(1H-Pyrrolo[2,3-b]pyridin-4-ylamino)-thiophene-2-carboxylic acid. LCMS (ESI) 393 (M+H) 1H NMR (400 MHz, DMSO-d6) δ ppm 11.42 (1H, br. s.) 8.89 (1H, s) 8.23 (1H, t, J=5.37 Hz) 8.04 (1H, dt, J=8.07, 0.92 Hz) 7.82 (1H, d, J=5.37 Hz) 7.50 (2H, dddd, J=6.92, 5.94, 0.78, 0.61 Hz) 7.26-7.41 (3H, m) 7.08-7.25 (7H, m) 6.48 (1H, d, J=2.34 Hz) 6.03 (1H, d, J=5.42 Hz) 3.46 (2H, s) 2.46 (2H, t, J=6.20 Hz)

IC$_{50}$ (p70S6K) >10 μM

83. 3-(1H-Pyrrolo[2,3-b]pyridin-4-ylamino)-benzo[b]thiophene-2-carboxylic acid ((S)-2-hydroxy-1-phenyl-ethyl)-amide

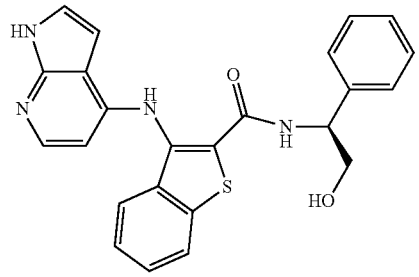 [SMILES: O=C(N[C@H](CO)c1ccccc1)c1sc2ccccc2c1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-2-phenylglycinol instead of 1-BOC-3-aminopyrrolidine and 3-(1H-Pyrrolo[2,3-b]pyridin-4-ylamino)-benzo[b]thiophene-2-carboxylic acid instead of 3-(1H-Pyrrolo[2,3-b]pyridin-4-ylamino)-thiophene-2-carboxylic acid. LCMS (ESI) 429 (M+H) 1H NMR (400 MHz, DMSO-d6) δ ppm 11.63 (1H, br. s.) 9.24 (1H, br. s.) 8.57 (1H, d, J=7.96 Hz) 8.09 (1H, d, J=8.10 Hz) 7.84 (1H, d, J=5.66 Hz) 7.59 (1H, d, J=7.96 Hz) 7.52 (1H, td, J=7.60, 1.15 Hz) 7.40 (1H, dd, J=15.13, 0.88 Hz) 7.28 (1H, dd, J=2.95, 1.44 Hz) 7.10-7.18 (1H, m) 7.06 (2H, t, J=7.32 Hz) 6.99-7.03 (2H, m) 6.50 (1H, br. s.) 6.04 (1H, d, J=5.66 Hz) 4.92-5.00 (1H, m) 4.90 (1H, t, J=5.30 Hz) 3.48 (2H, td, J=11.20, 5.71 Hz)

IC$_{50}$ (p70S6K) >10 μM

84. 3-(1H-Pyrrolo[2,3-b]pyridin-4-ylamino)-thiophene-2-carboxylic acid ((1S,2S)-2-hydroxy-1-hydroxymethyl-2-phenyl-ethyl)-amide

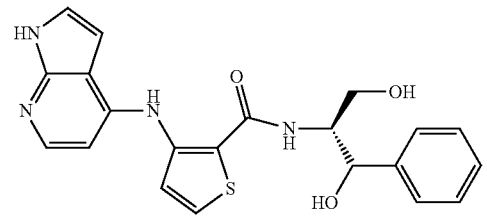

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (1S,2S)-2-amino-1-phenyl-1,3-propanediol instead of 1-BOC-3-aminopyrrolidine. LCMS (ESI) 409 (M+H) 1H NMR (400 MHz, DMSO-d6) δ ppm 11.48 (1H, br. s.) 9.67 (1H, s) 7.99 (1H, d, J=5.37 Hz) 7.76 (1H, d, J=5.32 Hz) 7.45 (1H, d, J=8.64 Hz) 7.33 (1H, d, J=5.37 Hz) 7.27 (1H, dd, J=3.54, 2.22 Hz) 7.21-7.25 (2H, m) 7.10-7.21 (3H, m) 6.62 (1H, d, J=5.42 Hz) 6.36 (1H, dd, J=3.54, 1.73 Hz) 5.55 (1H, d, J=4.73 Hz) 4.90 (1H, dd, J=4.83, 3.17 Hz) 4.84 (1H, t, J=5.64 Hz) 4.07 (1H, dt, J=7.80, 5.30 Hz) 3.50 (1H, dt, J=10.58, 6.96 Hz) 3.40 (1H, dt, J=10.55, 5.34 Hz)

IC$_{50}$ (p70S6K) "+"

85. 3-Hydroxy-2-{[3-(1H-pyrrolo[2,3-b]pyridin-4-ylamino)-thiophene-2-carbonyl]-amino}-propionic acid methyl ester

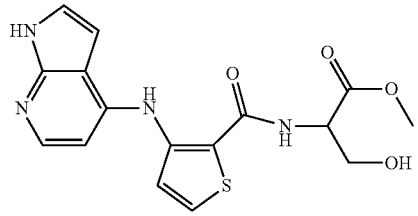 [SMILES: COC(=O)C(CO)NC(=O)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-amino-3-hydroxy-propionic acid methyl ester instead of 1-BOC-3-aminopyrrolidine. LCMS (ESI) 361 (M+H) 1H NMR (400 MHz, DMSO-d6) δ ppm 11.60 (1H, br. s.) 10.09 (1H, s) 8.13 (1H, d, J=7.57 Hz) 8.03 (1H, d, J=5.56 Hz) 7.85 (1H, d, J=5.42 Hz) 7.46 (1H, d, J=5.42 Hz) 7.32 (1H, dd, J=3.22, 2.64 Hz) 6.80 (1H, d, J=5.56 Hz) 6.43 (1H, dd, J=3.39, 1.78 Hz) 5.06 (1H, t, J=6.05 Hz) 4.56 (1H, dt, J=7.53, 5.02 Hz) 3.72-3.83 (2H, m) 3.63 (3H, s)

IC$_{50}$ (p70S6K) "++"

86. 3-(1H-Pyrrolo[2,3-b]pyridin-4-ylamino)-thiophene-2-carboxylic acid ((S)-1-benzyl-2-hydroxy-ethyl)-amide

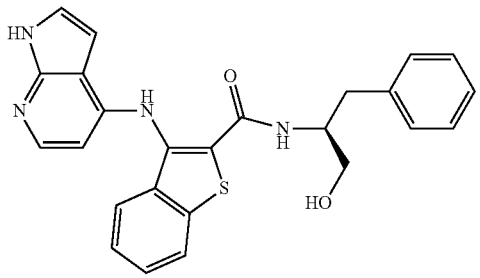 [SMILES: O=C(N[C@H](CO)Cc1ccccc1)c1sc2ccccc2c1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-phenylalaninol instead of 1-BOC-3-aminopyrrolidine. LCMS (ESI) 393 (M+H) 1H NMR (400 MHz, DMSO-d6) δ ppm 11.51 (1H, br. s.) 10.13 (1H, s) 7.98 (1H, d, J=5.47 Hz) 7.72-7.82 (2H, m) 7.40 (1H, d, J=5.42 Hz) 7.28 (1H, dd, J=3.44, 2.32 Hz) 7.19 (4H, d, J=0.10 Hz) 7.10 (1H, td, J=5.93, 2.59 Hz) 6.73 (1H, d, J=5.52 Hz) 6.38 (1H, dd, J=3.42, 1.76 Hz) 4.82 (1H, t, J=5.66 Hz) 4.13 (1H, ddd, J=14.19, 5.60, 3.15 Hz) 3.42-3.51 (1H, m) 3.38 (1H, t, J=5.93 Hz) 2.84-2.93 (1H, m) 2.73 (1H, dd, J=13.64, 8.96 Hz)

IC$_{50}$ (p70S6K) "+++"

87. 3-(1H-Pyrrolo[2,3-b]pyridin-4-ylamino)-thiophene-2-carboxylic acid 3-amino-benzylamide

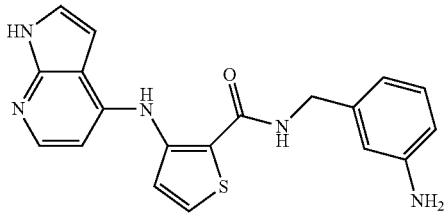 [SMILES: Nc1cccc(CNC(=O)c2sccc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-aminobenzylamine instead of 1-BOC-3-aminopyrrolidine. LCMS (ESI) 364 (M+H) 1H NMR (400 MHz, DMSO-d6) δ ppm 11.54 (1H, br. s.) 10.41 (1H, s) 8.58 (1H, t, J=5.93 Hz) 8.03 (1H, d, J=5.47 Hz) 7.80 (1H, d, J=5.42 Hz) 7.50 (1H, d, J=5.42 Hz) 7.31 (1H, dd, J=3.44, 2.32 Hz) 6.93 (1H, t, J=7.69 Hz) 6.85 (1H, d, J=5.47 Hz) 6.50 (1H, s) 6.35-6.46 (3H, m) 5.08 (2H, br. s.) 4.32 (2H, d, J=5.91 Hz)

IC$_{50}$ (p70S6K) "+++"

88. 3-(1H-Pyrrolo[2,3-b]pyridin-4-ylamino)-thiophene-2-carboxylic acid (1-benzylcarbamoyl-2-hydroxy-ethyl)-amide

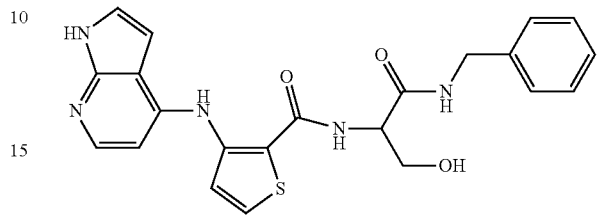

This compound was prepared in an analogous manner as 3-(1H-Pyrrolo[2,3-b]pyridin-4-ylamino)-thiophene-2-carboxylic acid (benzylcarbamoyl-methyl)-amide. LCMS (ESI) 436 (M+H) 1H NMR (400 MHz, DMSO-d6) δ ppm 11.52 (1H, br. s.) 10.11 (1H, s) 8.49 (1H, t, J=5.98 Hz) 8.01 (1H, d, J=5.47 Hz) 7.85 (1H, d, J=7.52 Hz) 7.81 (1H, d, J=5.42 Hz) 7.46 (1H, d, J=5.42 Hz) 7.21-7.34 (6H, m) 7.11-7.21 (1H, m) 6.79 (1H, d, J=5.42 Hz) 6.42 (1H, d, J=3.12 Hz) 5.00 (1H, t, J=5.42 Hz) 4.44-4.56 (1H, m) 4.29 (2H, d, J=6.10 Hz) 3.65-3.78 (2H, m)

IC$_{50}$ (p70S6K) "++"

89. 3-(1H-Pyrrolo[2,3-b]pyridin-4-ylamino)-thiophene-2-carboxylic acid [1-(4-chloro-3-trifluoromethyl-benzylcarbamoyl)-2-hydroxy-ethyl]-amide

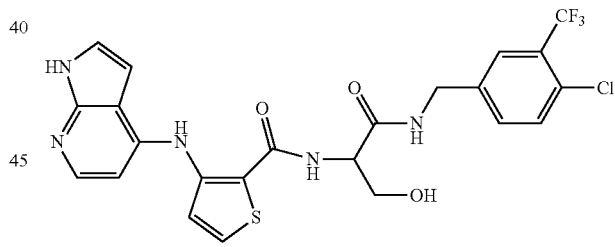

This compound was prepared in an analogous manner as 3-(1H-Pyrrolo[2,3-b]pyridin-4-ylamino)-thiophene-2-carboxylic acid (benzylcarbamoyl-methyl)-amide using name using 4-chloro-3-(trifluoromethyl)benzylamine instead of benzylamine. LCMS (ESI) 538 (M+H) 1H NMR (400 MHz, DMSO-d6) δ ppm 11.54 (1H, br. s.) 10.09 (1H, s) 8.63 (1H, t, J=6.00 Hz) 8.02 (1H, d, J=5.52 Hz) 7.91 (1H, d, J=7.81 Hz) 7.83 (1H, d, J=5.42 Hz) 7.75 (1H, s) 7.57 (2H, d, J=1.12 Hz) 7.47 (1H, d, J=5.42 Hz) 7.30 (1H, dd, J=3.07, 1.51 Hz) 6.81 (1H, d, J=5.42 Hz) 6.41 (1H, d, J=4.10 Hz) 5.04 (1H, t, J=5.76 Hz) 4.44-4.54 (1H, m) 4.37 (2H, d, J=5.66 Hz) 3.67-3.81 (2H, m)

IC$_{50}$ (p70S6K) "++"

90. 3-(1H-Pyrrolo[2,3-b]pyridin-4-ylamino)-thiophene-2-carboxylic acid [2-(4-chloro-3-trifluoromethyl-benzylamino)-ethyl]-amide

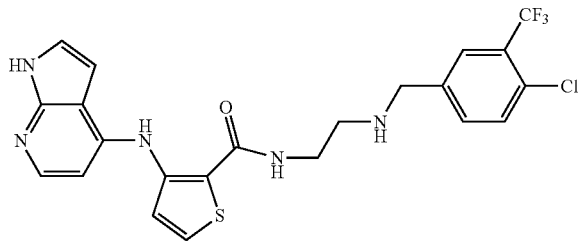 [SMILES: O=C(NCCNCc1ccc(Cl)c(C(F)(F)F)c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid [2-(4-methoxy-benzylamino)-ethyl]-amide using 4-chloro-3-(trifluoromethyl)benzaldehyde instead of 4-methoxy benzaldehyde. LCMS (ESI) 494 (M+H) 1H NMR (400 MHz, DMSO-d6) δ ppm 11.52 (1H, br. s.) 10.28 (1H, s) 7.95-8.09 (2H, m) 7.81 (1H, s) 7.77 (1H, d, J=5.42 Hz) 7.56-7.64 (2H, m) 7.47 (1H, d, J=5.42 Hz) 7.29 (1H, dd, J=3.27, 2.64 Hz) 6.80 (1H, d, J=5.47 Hz) 6.42 (1H, dd, J=3.51, 1.90 Hz) 3.75 (2H, s) 3.34 (2H, d, J=5.95 Hz) 2.62 (2H, t, J=6.56 Hz)

IC$_{50}$ (p70S6K) "+++"

91. 3-{[3-(1H-Pyrrolo[2,3-b]pyridin-4-ylamino)-thiophene-2-carbonyl]-amino}-piperidine-1-carboxylic acid tert-butyl ester

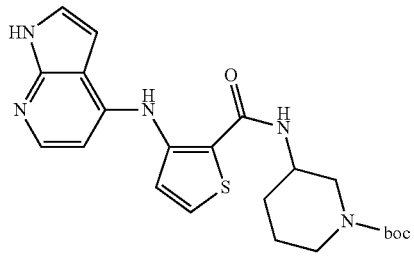

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-BOC-3-aminopiperidine instead of 1-BOC-3-aminopyrrolidine. LCMS (ESI) 442 (M+H) 1H NMR (400 MHz, DMSO-d6) δ ppm 11.52 (1H, br. s.) 10.27 (1H, br. s.) 8.02 (1H, d, J=5.47 Hz) 7.87 (1H, d, J=8.20 Hz) 7.80 (1H, d, J=5.37 Hz) 7.47 (1H, d, J=5.47 Hz) 7.31 (1H, dd, J=3.32, 2.54 Hz) 6.80 (1H, d, J=5.47 Hz) 6.44 (1H, dd, J=3.42, 1.76 Hz) 3.79 (3H, dd, J=6.78, 3.17 Hz) 2.76 (1H, t, J=12.45 Hz) 1.83 (1H, dd, J=12.93, 3.27 Hz) 1.65 (1H, dd, J=8.69, 3.22 Hz) 1.52 (1H, dd, J=11.76, 3.95 Hz) 1.37 (9H, s)

IC$_{50}$ (p70S6K) "++"

92. (R)-2-({[3-(1H-Pyrrolo[2,3-b]pyridin-4-ylamino)-thiophene-2-carbonyl]-amino}methyl)pyrrolidine-1-carboxylic acid tert-butyl ester

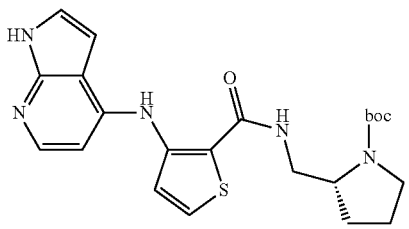

This compound was prepared in an analogous manner as 3-(1H-Pyrrolo[2,3-b]pyridin-4-ylamino)-thiophene-2-carboxylic acid (2-amino-ethyl)-amide using (R)-2-(aminomethyl)-1-N-BOC-pyrrolidine instead of tert-butyl-2-amino ethyl carbamate. LCMS (ESI) 442 (M+H) 1H NMR (400 MHz, DMSO-d6) δ ppm 11.52 (1H, br. s.) 10.48 (1H, br. s.) 10.24 (1H, br. s.) 8.17 (1H, br. s.) 8.02 (1H, d, J=5.47 Hz) 7.79 (1H, d, J=5.27 Hz) 7.44-7.54 (1H, m) 7.31 (1H, d, J=2.73 Hz) 6.82 (1H, br. s.) 6.41 (1H, br. s.) 3.93 (1H, br. s.) 3.39 (1H, br. s.) 3.23 (2H, br.s.) 1.67-1.88 (4H, m) 1.39 (9H, s)

IC$_{50}$ (p70S6K) "++"

93. 3-(1H-Pyrrolo[2,3-b]pyridin-4-ylamino)-thiophene-2-carboxylic acid ((R)-1-pyrrolidin-2-ylmethyl)-amide

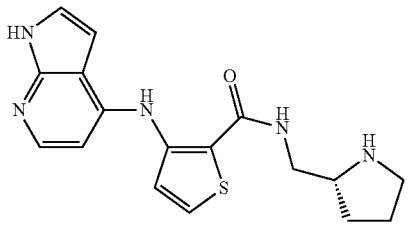 [SMILES: O=C(NC[C@H]1CCCN1)c1sccc1Nc1ccnc2[nH]ccc12]

To a solution of (R)-2-({[3-(1H-Pyrrolo[2,3-b]pyridin-4-ylamino)-thiophene-2-carbonyl]-amino}methyl)pyrrolidine-1-carboxylic acid tert-butyl ester (61 mg, 0.14 mmol) in THF (1.0 mL) was added HCl in dioxane (1.0 M, 10 equiv) and stirred at room temperature for 24 H. The cloudy solution was concentrated in vacuo, then the solid was triturated with ethyl ether, and filtered to provide 437 (41 mg, 87%). LCMS (ESI) 340 (M+H) 1H NMR (400 MHz, DMSO-d6) δ ppm 12.53 (1H, br. s.) 10.79 (1H, s) 9.56 (1H, br. s.) 8.88 (1H, br. s.) 8.78 (1H, t, J=5.66 Hz) 8.08 (1H, d, J=6.83 Hz) 7.92 (1H, d, J=5.27 Hz) 7.40 (1H, d, J=2.73 Hz) 7.33 (1H, d, J=5.27 Hz) 6.95 (1H, br. s.) 6.71 (1H, d, J=7.03 Hz) 3.27-3.69 (5H, m) 3.04-3.25 (2H, m) 1.71-2.03 (2H, m) 1.46-1.67 (1H, m)

IC$_{50}$ (p70S6K) "++"

94. 3-(1H-Pyrrolo[2,3-b]pyridin-4-ylamino)-thiophene-2-carboxylic acid 3-methoxybenzylamide

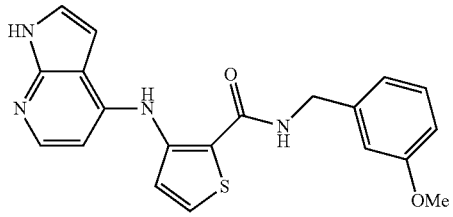 [SMILES: COc1cccc(CNC(=O)c2sccc2Nc2ccnc3[nH]ccc23)c1]

This compound was prepared in an analogous manner as 3-(1H-Pyrrolo[2,3-b]pyridin-4-ylamino)-thiophene-2-carboxylic acid (2-amino-ethyl)-amide using 3-methoxybenzylamine instead of tert-butyl-2-amino ethyl carbamate. LCMS (ESI) 379 (M+H) 1H NMR (400 MHz, DMSO-d6) δ ppm 11.52 (1H, br. s.) 10.48 (1H, br. s.) 10.24 (1H, br. s.) 8.17 (1H, br. s.) 8.02 (1H, d, J=5.47 Hz) 7.79 (1H, d, J=5.27 Hz) 7.44-7.54 (1H, m) 7.31 (1H, d, J=2.73 Hz) 6.82 (1H, br. s.) 6.41 (1H, br. s.) 3.93 (1H, br. s.) 3.39 (1H, br. s.) 3.23 (2H, br.s.) 1.67-1.88 (4H, m) 1.39 (9H, s)

IC$_{50}$ (p70S6K) "+++"

95. 3-(1H-Pyrrolo[2,3-b]pyridin-4-ylamino)-thiophene-2-carboxylic acid 3,5-dimethoxy-benzylamide

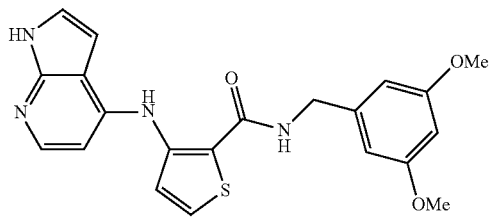 [SMILES: COc1cc(CNC(=O)c2sccc2Nc2ccnc3[nH]ccc23)cc(OC)c1]

This compound was prepared in an analogous manner as 3-(1H-Pyrrolo[2,3-b]pyridin-4-ylamino)-thiophene-2-carboxylic acid (2-amino-ethyl)-amide using 3,5-dimethoxybenzylamine instead of tert-butyl-2-amino ethyl carbamate. LCMS (ESI) 409 (M+H) 1H NMR (400 MHz, DMSO-d6) δ ppm 11.53 (1H, br. s.) 10.30 (1H, s) 8.65 (1H, t, J=5.95 Hz) 8.03 (1H, d, J=5.42 Hz) 7.80 (1H, d, J=5.42 Hz) 7.50 (1H, d, J=5.42 Hz) 7.30 (1H, dd, J=3.32, 2.20 Hz) 6.84 (1H, d, J=5.47 Hz) 6.48 (2H, d, J=2.25 Hz) 6.42 (1H, dd, J=3.44, 1.44 Hz) 6.37 (1H, t, J=2.27 Hz) 4.39 (2H, d, J=6.00 Hz) 3.70 (6H, s)

IC$_{50}$ (p70S6K) "++"

96. 3-(1H-Pyrrolo[2,3-b]pyridin-4-ylamino)-thiophene-2-carboxylic acid ((S)-1-hydroxymethyl-2-methyl-propyl)-amide

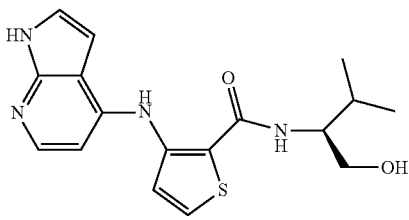 [SMILES: CC(C)[C@@H](CO)NC(=O)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using (2S)-2-amino-3-methylbutan-1-ol instead of tert-butyl-2-amino ethyl carbamate. LCMS (ESI) 345 (M+H) 1H NMR (400 MHz, DMSO-d6) δ ppm 11.49 (1H, br. s.) 10.02 (1H, s) 7.99 (1H, d, J=5.47 Hz) 7.79 (1H, d, J=5.27 Hz) 7.57 (1H, d, J=8.98 Hz) 7.41 (1H, d, J=5.47 Hz) 7.29 (1H, dd, J=3.32, 2.34 Hz) 6.69 (1H, d, J=5.47 Hz) 6.42 (1H, dd, J=3.51, 1.56 Hz) 4.58 (1H, t, J=5.56 Hz) 3.80 (1H, dd, J=8.88, 6.74 Hz) 3.46 (2H, t, J=5.95 Hz) 1.85 (1H, dq, J=13.64, 6.78 Hz) 0.85 (3H, d, J=6.64 Hz) 0.78 (3H, d, J=6.83 Hz)

IC$_{50}$ (p70S6K) "++"

97. 3-(1H-Pyrrolo[2,3-b]pyridin-4-ylamino)-thiophene-2-carboxylic acid ((S)-1-hydroxymethyl-3-methyl-butyl)-amide

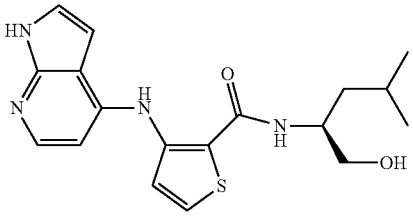 [SMILES: CC(C)C[C@@H](CO)NC(=O)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using (2S)-2-amino-4-methylpentan-1-ol instead of tert-butyl-2-amino ethyl carbamate. LCMS (ESI) 359 (M+H) 1H NMR (400 MHz, DMSO-d6) δ ppm 11.51 (1H, br. s.) 10.23 (1H, s) 8.00 (1H, d, J=5.37 Hz) 7.78 (1H, d, J=5.37 Hz) 7.62 (1H, d, J=8.59 Hz) 7.45 (1H, d, J=5.37 Hz) 7.30 (1H, dd, J=3.12, 1.85 Hz) 6.75 (1H, d, J=5.47 Hz) 6.42 (1H, d, J=2.73 Hz) 4.68 (1H, t, J=5.66 Hz) 4.05 (1H, td, J=9.42, 4.39 Hz) 3.36-3.47 (1H, m) 1.46-1.63 (1H, m, J=13.76, 6.82, 6.82, 6.65, 6.65 Hz) 1.23-1.45 (2H, m, J=13.36, 9.07, 9.07, 8.92, 4.59 Hz) 0.83 (6H, dd, J=6.54, 4.30 Hz)

IC$_{50}$ (p70S6K) "++"

98. 3-(1H-Pyrrolo[2,3-b]pyridin-4-ylamino)-thiophene-2-carboxylic acid 4-chloro-3-trifluoromethyl-benzylamide

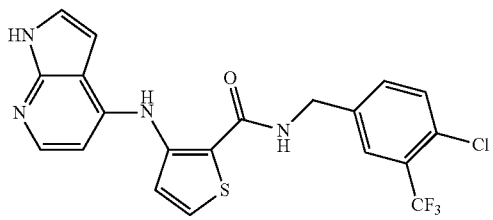 [SMILES: O=C(NCc1ccc(Cl)c(C(F)(F)F)c1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using 3-chloro-4-(trifluoromethyl)benzylamine instead of tert-butyl-2-amino ethyl carbamate. LCMS (ESI) 451 (M+H) 1H NMR (400 MHz, DMSO-d6) δ ppm 11.54 (1H, br. s.) 10.24 (1H, s) 8.76 (1H, t, J=5.98 Hz) 8.02 (1H, d, J=5.47 Hz) 7.82 (2H, d, J=4.05 Hz) 7.65-7.71 (1H, m) 7.58-7.64 (1H, m) 7.50 (1H, d, J=5.42 Hz) 7.30 (1H, dd, J=3.29, 2.56 Hz) 6.84 (1H, d, J=5.42 Hz) 6.40 (1H, dd, J=3.49, 1.93 Hz) 4.52 (2H, d, J=5.91 Hz)

IC$_{50}$ (p70S6K) "+++"

99. 3-(1H-Pyrrolo[2,3-b]pyridin-4-ylamino)-thiophene-2-carboxylic acid (2-hydroxy-2-phenyl-ethyl)-amide

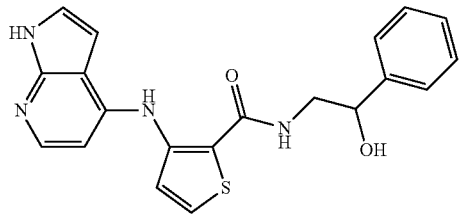 [SMILES: O=C(NCC(O)c1ccccc1)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using 2-amino-1-phenyl ethanol instead of tert-butyl-2-amino ethyl carbamate. LCMS (ESI) 379 (M+H) 1H NMR (400 MHz, DMSO-d6) δ ppm 11.53 (1H, br. s.) 10.17 (1H, s) 8.07 (1H, t, J=5.37 Hz) 8.02 (1H, d, J=5.47 Hz) 7.77 (1H, d, J=5.47 Hz) 7.45 (1H, d, J=5.27 Hz) 7.27-7.38 (6H, m) 7.18-7.26 (1H, m) 6.79 (1H, d, J=5.47 Hz) 6.44 (1H, d, J=3.51 Hz) 5.51 (1H, d, J=3.90 Hz) 4.77 (1H, ddd, J=7.86, 4.30, 4.05 Hz) 3.47 (1H, dt, J=13.13, 5.15 Hz)

IC$_{50}$ (p70S6K) "+++"

100. 3-(1H-Pyrrolo[2,3-b]pyridin-4-ylamino)-thiophene-2-carboxylic acid 3-(4-fluoro-benzoylamino)-benzylamide

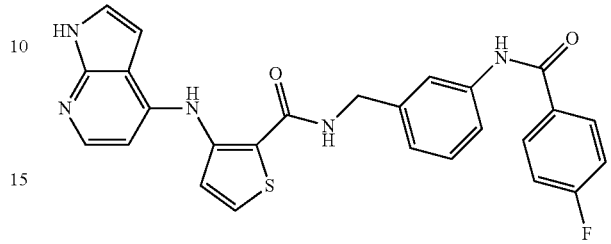

This compound was prepared in an analogous manner as 3-(1H-Pyrrolo[2,3-b]pyridin-4-ylamino)-thiophene-2-carboxylic acid (2-amino-ethyl)-amide using N[3-(aminomethyl)phenyl]-4-fluorobenzamide instead of tert-butyl-2-amino ethyl carbamate. LCMS (ESI) 486 (M+H) 1H NMR (400 MHz, DMSO-d6) δ ppm 11.53 (1H, s) 10.39 (1H, s) 10.26 (1H, s) 8.66-8.78 (1H, m) 8.02 (4H, dt, J=5.48, 2.70 Hz) 7.81 (1H, d, J=5.42 Hz) 7.68 (2H, d, J=8.20 Hz) 7.51 (1H, d, J=5.47 Hz) 7.24-7.40 (5H, m) 7.06 (1H, d, J=7.42 Hz) 6.86 (1H, d, J=5.52 Hz) 6.43 (1H, dd, J=3.54, 1.93 Hz) 4.47 (2H, d, J=5.86 Hz)

IC$_{50}$ (p70S6K) "+++"

101. 3-(1H-Pyrrolo[2,3-b]pyridin-4-ylamino)-thiophene-2-carboxylic acid (1-benzyl-1H-[1,2,3]triazol-4-ylmethyl)-amide

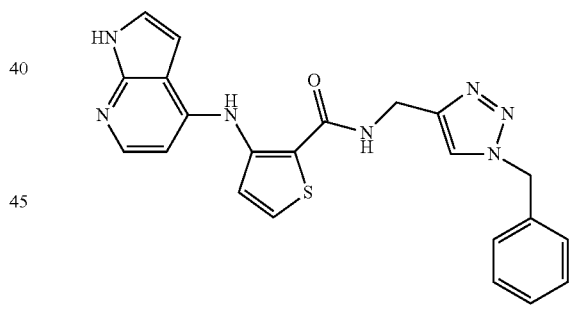

This compound was prepared in an analogous manner as 3-(1H-Pyrrolo[2,3-b]pyridin-4-ylamino)-thiophene-2-carboxylic acid (2-amino-ethyl)-amide using propargylamine instead of tert-butyl-2-amino ethyl carbamate to afford N-(prop-2-yn-1-yl)-3-(1H-pyrrolo[2,3-b]pyridin-4-ylamino)thiophene-2-carboxamide.

A solution of N-(prop-2-yn-1-yl)-3-(1H-pyrrolo[2,3-b]pyridin-4-ylamino)thiophene-2-carboxamide (100 mg, 0.34 mmol), copper iodide (6 mg, 0.03 mmol), benzyl azide (45 mg, 0.34 mmol) in THF (2 mL) was heated to 50° C. for 18 h. The reaction was cooled to room temperature then diluted with water and extracted with ethylacetate (3×). The organic layers were dried over sodium sulfate and concentrated in vacuo. The residue was purified by ISCO flash chromatography (silica) to afford 2448 (106 mg, 73%) LCMS (ESI) 430 (M+H) 1H NMR (400 MHz, DMSO-d6) δ ppm 11.54 (1H, br. s.) 10.31 (1H, s) 8.65 (1H, t, J=5.76 Hz) 8.03 (1H, d, J=5.37

Hz) 7.99 (1H, s) 7.79 (1H, d, J=5.37 Hz) 7.48 (1H, d, J=5.47 Hz) 7.32 (6H, quin, J=7.98 Hz) 6.83 (1H, d, J=5.47 Hz) 6.43 (1H, dd, J=3.51, 1.95 Hz) 5.54 (2H, s) 4.48 (2H, d, J=5.66 Hz)

IC$_{50}$ (p70S6K) "++"

102. 3-{[2-(1H-Pyrrolo[2,3-b]pyridin-4-ylamino)-thiophene-3-carbonyl]-amino}-pyrrolidine-1-carboxylic acid tert-butyl ester

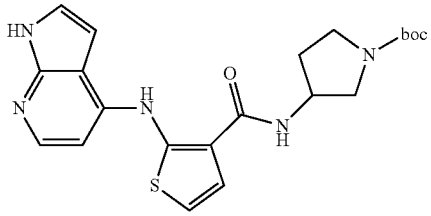

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-BOC-3-aminopiperidine instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 428 (M+H) 1H NMR (400 MHz, DMSO-d6) δ ppm 11.85 (1H, br. s.) 11.67 (1H, br. s.) 8.28 (1H, d, J=6.83 Hz) 8.15 (1H, d, J=5.42 Hz) 7.57 (1H, d, J=5.81 Hz) 7.38 (1H, dd, J=3.27, 2.68 Hz) 6.99 (1H, d, J=5.47 Hz) 6.93 (1H, d, J=6.05 Hz) 6.47 (1H, dd, J=3.49, 1.88 Hz) 4.40-4.59 (1H, m, J=12.24, 6.09, 6.09, 5.83 Hz) 3.51-3.64 (1H, m) 3.41 (1H, t, J=7.74 Hz) 3.21 (1H, td, J=9.91, 5.52 Hz) 2.06-2.19 (1H, m) 1.90 (1H, td, J=11.17, 6.61 Hz) 1.41 (9H, br. s.)

IC$_{50}$ (p70S6K) "++"

103. 2-(1H-Pyrrolo[2,3-b]pyridin-4-ylamino)-thiophene-3-carboxylic acid pyrrolidin-3-ylamide

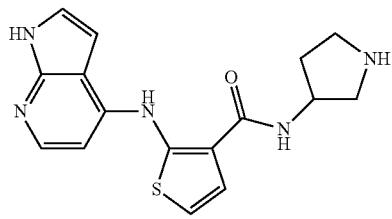 [SMILES: O=C(NC1CCNC1)c1ccsc1Nc1ccnc2[nH]ccc12]

This compound was prepared in an analogous manner as 3-(1H-Pyrrolo[2,3-b]pyridin-4-ylamino)-thiophene-2-carboxylic acid ((R)-1-pyrrolidin-2-ylmethyl)-amide using 3-{[2-(1H-Pyrrolo[2,3-b]pyridin-4-ylamino)-thiophene-3-carbonyl]-amino}-pyrrolidine-1-carboxylic acid tert-butyl ester instead of (R)-2-({[3-(1H-Pyrrolo[2,3-b]pyridin-4-ylamino)-thiophene-2-carbonyl]-amino}methyl)pyrrolidine-1-carboxylic acid tert-butyl ester LCMS (ESI) 328 (M+H) 1H NMR (400 MHz, DMSO-d6) δ ppm 12.58 (1H, br. s.) 11.49 (1H, s) 8.89 (1H, d, J=6.93 Hz) 8.18 (1H, d, J=6.74 Hz) 7.67 (1H, d, J=5.86 Hz) 7.46 (1H, dd, J=3.32, 2.34 Hz) 7.42 (1H, d, J=5.86 Hz) 6.80 (1H, d, J=6.83 Hz) 6.76 (1H, dd, J=3.42, 1.56 Hz) 4.49 (1H, dt, J=6.66, 4.53 Hz) 3.33 (2H, dt, J=12.40, 6.30 Hz) 3.18 (2H, td, J=10.93, 6.44 Hz) 2.12 (1H, dd, J=13.42, 7.47 Hz) 1.84-2.00 (0H, m) 1.16-1.42 (1H, m)

IC$_{50}$ (p70S6K) "+++"

104. 3-{[2-(1H-Pyrrolo[2,3-b]pyridin-4-ylamino)-thiophene-3-carbonyl]-amino}-piperidine-1-carboxylic acid tert-butyl ester

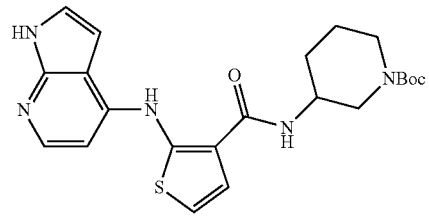 [SMILES: CC(C)(C)OC(=O)N1CCCC(NC(=O)c2ccsc2Nc2ccnc3[nH]ccc23)C1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-BOC-3-aminopiperidine instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 442 (M+H) 1H NMR (400 MHz, DMSO-d6) δ ppm 11.90 (1H, br. s.) 11.64 (1H, s) 8.13 (1H, d, J=5.42 Hz) 7.99 (1H, d, J=6.30 Hz) 7.53 (1H, d, J=5.91 Hz) 7.35 (1H, dd, J=3.44, 2.46 Hz) 6.96 (1H, d, J=5.42 Hz) 6.90 (1H, d, J=5.81 Hz) 6.44 (1H, dd, J=3.47, 2.00 Hz) 3.82 (1H, td, J=8.59, 4.93 Hz) 2.78 (1H, br. s.) 1.82-1.94 (1H, m) 1.66-1.77 (1H, m) 1.53 (1H, d, J=11.42 Hz) 1.31-1.45 (10H, m)

IC$_{50}$ (p70S6K) "++"

105. 2-(1H-Pyrrolo[2,3-b]pyridin-4-ylamino)-thiophene-3-carboxylic acid piperidin-3-ylamide

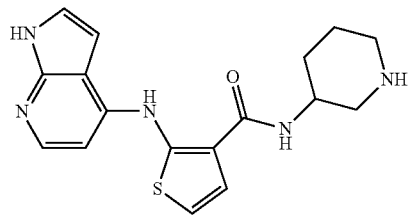 [SMILES: O=C(NC1CCCNC1)c1ccsc1Nc1ccnc2[nH]ccc12]

This compound was prepared in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 342 (M+H) 1H NMR (400 MHz, DMSO-d6) δ ppm 12.61 (1H, br. s.) 11.52 (1H, s) 9.39 (1H, br. s.) 9.14 (1H, br. s.) 8.76 (1H, d, J=5.27 Hz) 8.16 (1H, br.s.) 7.66 (1H, br. s.) 7.43 (2H, d, J=11.91 Hz) 6.76 (2H, d, J=8.10 Hz) 4.14 (1H, br.

s.) 3.47 (2H, br. s.) 3.00-3.27 (2H, m) 2.85 (2H, br. s.) 1.71-2.00 (2H, m) 1.49-1.72 (2H, m) 1.25 (1H, d, J=18.16 Hz) IC$_{50}$ (p70S6K) "+++"

106. 3-(1H-Pyrrolo[2,3-b]pyridin-4-ylamino)-thiophene-2-carboxylic acid [2-amino-1-(3-fluorophenyl)-ethyl]-amide

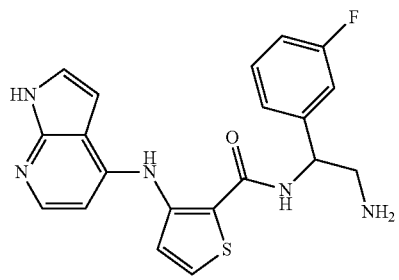 [SMILES: NCC(NC(=O)c1sccc1Nc1ccnc2[nH]ccc12)c1cccc(F)c1]

This compound was prepared in an analogous manner as 3-(1H-Pyrrolo[2,3-b]pyridin-4-ylamino)-thiophene-2-carboxylic acid (2-amino-ethyl)-amide using tert-butyl [2-amino-2-(3-fluorophenyl)ethyl]carbamate instead of tert-butyl-2-amino ethyl carbamate. LCMS (ESI) 496 (M+H) followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 396 (M+H) 1H NMR (400 MHz, DMSO-d6) δ ppm 12.42 (1H, br. s.) 10.87 (1H, s) 9.24 (1H, d, J=8.59 Hz) 8.20 (1H, br. s.) 8.01 (1H, d, J=6.78 Hz) 7.95 (1H, d, J=5.22 Hz) 7.41 (1H, dd, J=3.51, 2.59 Hz) 7.32 (1H, d, J=5.22 Hz) 7.18-7.27 (1H, m) 7.13-7.17 (1H, m) 7.10 (1H, dd, J=12.89, 1.61 Hz) 7.04 (1H, td, J=8.90, 3.29 Hz) 6.94 (1H, br. s.) 6.58 (1H, d, J=6.93 Hz) 5.32 (1H, dd, J=18.28, 4.32 Hz) 3.18 (1H, dd, J=11.86, 5.12 Hz)

IC$_{50}$ (p70S6K) "+++"

107. 3-(1H-Pyrrolo[2,3-b]pyridin-4-ylamino)-thiophene-2-carboxylic acid [2-amino-1-(2-methoxyphenyl)-ethyl]-amide

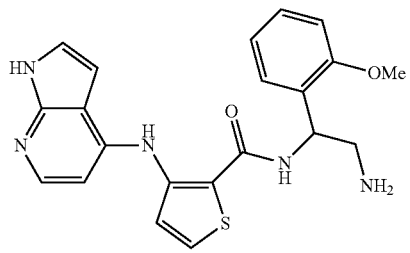 [SMILES: COc1ccccc1C(CN)NC(=O)c1sccc1Nc1ccnc2[nH]ccc12]

This compound was prepared in an analogous manner as 3-(1H-Pyrrolo[2,3-b]pyridin-4-ylamino)-thiophene-2-carboxylic acid (2-amino-ethyl)-amide using tert-butyl [2-amino-2-(2-methoxyphenyl)ethyl]carbamate instead of tert-butyl-2-amino ethyl carbamate. LCMS (ESI) 508 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 408 (M+H) 1H NMR (400 MHz, DMSO-d6) δ ppm 12.39 (1H, s) 10.85 (0H, s) 8.90 (0H, d, J=8.88 Hz) 8.14 (0H, br. s.) 8.03 (0H, d, J=6.74 Hz) 7.94 (0H, d, J=5.27 Hz) 7.43 (0H, dd, J=3.27, 2.49 Hz) 7.32 (0H, d, J=5.17 Hz) 7.20 (2H, ddd, J=7.64, 1.98, 1.71 Hz) 6.86-6.99 (2H, m) 6.62 (2H, t, J=7.22 Hz) 5.57 (0H, ddd, J=13.96, 5.03, 4.73 Hz) 3.67 (3H, s) 3.23 (1H, br. s.) 3.04 (0H, s)

IC$_{50}$ (p70S6K) "+++"

108. 2-(1H-Pyrrolo[2,3-b]pyridin-4-ylamino)-thiophene-3-carboxylic acid [2-amino-1-(3-fluorophenyl)-ethyl]-amide

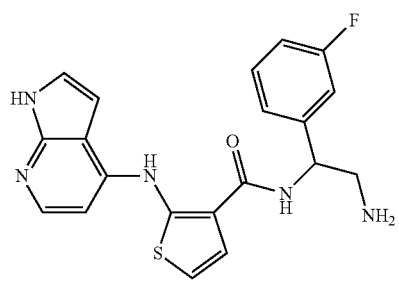

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-fluorophenyl)ethyl]carbamate instead of 1-BOC-3-aminopyrrolidine. LCMS (ESI) 496 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 396 (M+H) 1H NMR (400 MHz, DMSO-d6) δ ppm 12.57 (1H, br. s.) 11.38 (1H, s) 9.36 (1H, d, J=8.15 Hz) 8.28 (3H, br. s.) 8.09 (1H, d, J=6.78 Hz) 7.76 (1H, d, J=5.86 Hz) 7.47 (1H, d, J=5.81 Hz) 7.43 (1H, dd, J=3.37, 2.34 Hz) 7.24 (1H, dd, J=7.98, 5.88 Hz) 7.17 (2H, dd, J=5.54, 2.86 Hz) 7.04 (1H, td, J=8.22, 2.00 Hz) 6.77 (1H, d, J=3.22 Hz) 6.70 (1H, d, J=6.83 Hz) 5.30 (1H, dd, J=8.30, 5.56 Hz) 3.39 (1H, dd, J=8.74, 5.52 Hz) 3.17 (1H, dd, J=11.62, 6.20 Hz)

IC$_{50}$ (p70S6K) "+++"

109. 2-(1H-Pyrrolo[2,3-b]pyridin-4-ylamino)-thiophene-3-carboxylic acid [2-amino-1-(2-methoxyphenyl)-ethyl]-amide

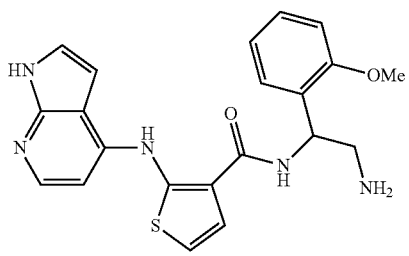 [SMILES: COc1ccccc1C(CN)NC(=O)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(2-methoxyphenyl)ethyl] carbamate instead of 1-BOC-3-aminopyrrolidine. LCMS (ESI) 508 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 408 (M+H) 1H NMR (400 MHz, DMSO-d6) δ ppm 12.63 (1H, br. s.) 11.42 (1H, s) 9.22 (1H, d, J=8.49 Hz) 8.29 (3H, br. s.) 8.10 (1H, d, J=6.83 Hz) 7.77 (1H, d, J=5.86 Hz) 7.48 (1H, d, J=5.86 Hz) 7.44 (1H, dd, J=3.27, 2.39 Hz) 7.25 (1H, dd, J=7.71, 1.46 Hz) 7.19 (1H, td, J=7.83, 1.61 Hz) 6.95 (1H, d, J=8.00 Hz) 6.82 (1H, br. s.) 6.69 (1H, d, J=6.93 Hz) 6.62 (1H, t, J=7.47 Hz) 5.56 (1H, dd, J=10.54, 4.69 Hz) 3.78 (3H, s) 3.23 (1H, dd, J=11.47, 5.71 Hz) 3.02 (1H, td, J=8.44, 4.78 Hz)

IC$_{50}$ (p70S6K) "+++"

110. 2-(1H-Pyrrolo[2,3-b]pyridin-4-ylamino)-thiophene-3-carboxylic acid [2-amino-1-(3,4-dimethoxy-phenyl)-ethyl]-amide

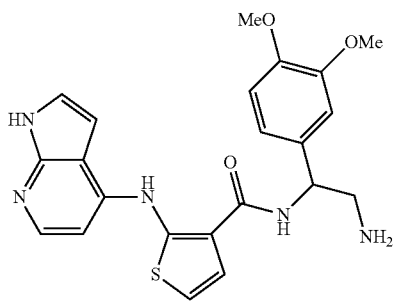 [SMILES: COc1ccc(C(CN)NC(=O)c2ccsc2Nc2ccnc3[nH]ccc23)cc1OC]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3,4-dimethoxyphenyl)ethyl]carbamate instead of 1-BOC-3-aminopyrrolidine. LCMS (ESI) 538 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 438 (M+H) 1H NMR (400 MHz, DMSO-d6) δ ppm 12.61 (1H, br. s.) 11.47 (1H, s) 9.24 (1H, d, J=8.54 Hz) 8.22 (3H, br. s.) 8.09 (1H, d, J=6.88 Hz) 7.75 (1H, d, J=5.86 Hz) 7.42-7.47 (2H, m) 7.06 (1H, d, J=1.95 Hz) 6.82 (1H, dd, J=8.25, 1.90 Hz) 6.79 (1H, br. s.) 6.71 (1H, s) 6.69 (1H, d, J=2.54 Hz) 5.22 (1H, td, J=9.15, 4.34 Hz) 3.69 (3H, s) 3.68 (3H, s) 3.34 (0H, d, J=3.17 Hz) 3.12 (1H, dd, J=12.20, 6.25 Hz)

IC$_{50}$ (p70S6K) "+++"

111. 2-(1H-Pyrrolo[2,3-b]pyridin-4-ylamino)-thiophene-3-carboxylic acid 3-amino-benzylamide

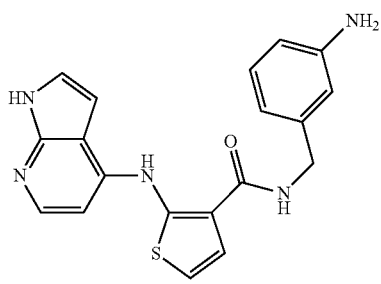 [SMILES: Nc1cccc(CNC(=O)c2ccsc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 3-aminobenzyl amine instead of 1-BOC-3-aminopyrrolidine. LCMS (ESI) 364 (M+H) 1H NMR (400 MHz, DMSO-d6) δ ppm 12.01 (1H, s) 11.66 (1H, s) 8.77 (1H, t, J=6.20 Hz) 8.16 (1H, d, J=5.42 Hz) 7.57 (1H, d, J=5.86 Hz) 7.37 (1H, dd, J=3.51, 2.54 Hz) 7.00 (1H, d, J=5.42 Hz) 6.95-6.98 (1H, m) 6.93 (1H, dd, J=5.10, 0.66 Hz) 6.53 (1H, t, J=2.03 Hz) 6.45-6.49 (2H, m) 6.42 (1H, ddd, J=8.03, 2.22, 1.03 Hz) 5.03 (2H, s) 4.39 (2H, d, J=5.95 Hz)

IC$_{50}$ (p70S6K) "+++"

112. 2-(1H-Pyrrolo[2,3-b]pyridin-4-ylamino)-thiophene-3-carboxylic acid benzylamide

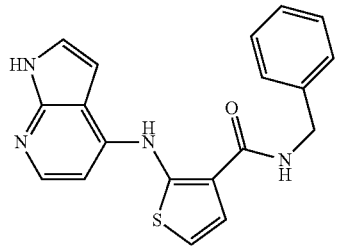 [SMILES: O=C(NCc1ccccc1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using benzyl amine instead of 1-BOC-3-aminopyrrolidine. LCMS (ESI) 349 (M+H) 1H NMR (400 MHz, DMSO-d6) δ ppm 11.93 (1H, s) 11.67 (1H, br. s.) 8.88 (1H, t, J=5.95 Hz) 8.16 (1H, d, J=5.47 Hz) 7.55 (1H, d, J=5.86 Hz) 7.30-7.42 (6H, m) 7.25 (1H, ddd, J=5.88, 2.73, 2.51 Hz) 7.00 (1H, d, J=5.47 Hz) 6.94 (1H, d, J=5.66 Hz) 6.45 (1H, dd, J=3.51, 1.85 Hz) 4.53 (2H, d, J=5.86 Hz)

IC$_{50}$ (p70S6K) "+++"

113. 3-(1H-Pyrrolo[2,3-b]pyridin-4-ylamino)-thiophene-2-carboxylic acid [2-amino-1-(3,4-dimethoxy-phenyl)-ethyl]-amide

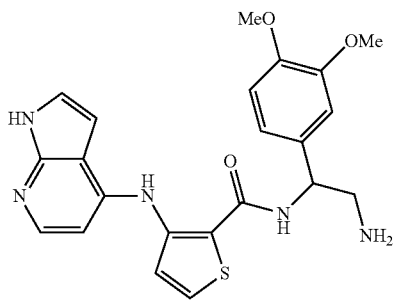 [SMILES: COc1ccc(C(CN)NC(=O)c2sccc2Nc2ccnc3[nH]ccc23)cc1OC]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3,4-dimethoxyphenyl) ethyl]carbamate instead of 1-BOC-3-aminopyrrolidine. LCMS (ESI) 538 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 438 (M+H) 1H NMR (400 MHz, DMSO-d6) δ ppm 12.53 (1H, br. s.) 11.01 (1H, s) 9.23 (1H, d, J=8.49 Hz) 8.20 (3H, br. s.) 8.00 (1H, d, J=6.93 Hz) 7.92 (1H, d, J=5.27 Hz) 7.40 (1H, dd, J=3.37, 2.29 Hz) 7.28 (1H, d, J=5.27 Hz) 7.01 (1H, br. s.) 6.97 (1H, d, J=2.05 Hz) 6.79 (1H, dd, J=8.35, 2.00 Hz) 6.65 (1H, d, J=8.30 Hz) 6.54 (1H, d, J=6.93 Hz) 5.23 (1H, td, J=8.83, 4.88 Hz) 3.67 (3H, s) 3.56 (3H, s) 3.34 (1H, dd, J=7.42, 3.03 Hz) 3.11 (1H, t, J=12.30 Hz)

IC$_{50}$ (p70S6K) "+++"

114. 2-(1H-Pyrrolo[2,3-b]pyridin-4-ylamino)-thiophene-3-carboxylic acid ((S)-2-azido-1-phenyl-ethyl)-amide

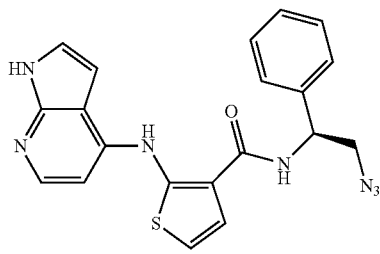 [SMILES: [N-]=[N+]=NC[C@@H](NC(=O)c1ccsc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-azido-1-phenylethanamine instead of 1-BOC-3-aminopyrrolidine. LCMS (ESI) 404 (M+H) 1H NMR (400 MHz, DMSO-d6) δ ppm 11.73 (1H, s) 11.67 (1H, br. s.) 8.76 (1H, d, J=8.64 Hz) 8.15 (1H, d, J=5.47 Hz) 7.65 (1H, d, J=5.86 Hz) 7.48 (2H, d, J=7.22 Hz) 7.34-7.42 (3H, m) 7.24-7.32 (1H, m) 6.99 (2H, dd, J=5.69, 1.34 Hz) 6.43 (1H, dd, J=3.44, 1.88 Hz) 5.38 (1H, td, J=8.98, 5.22 Hz) 3.72-3.81 (1H, m) 3.61-3.70 (1H, m)

IC$_{50}$ (p70S6K) "+++"

115. 3-(1H-Pyrrolo[2,3-b]pyridin-4-ylamino)-thiophene-2-carboxylic acid ((R)-2-cyano-1-phenyl-ethyl)-amide

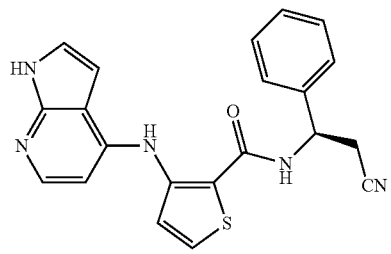 [SMILES: N#CC[C@@H](NC(=O)c1sccc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (3R)-3-amino-3-phenylpropanenitrile (*Organic Synthesis* 2008, 85, 219-230) instead of 1-BOC-3-aminopyrrolidine. LCMS (ESI) 388 (M+H) 1H NMR (400 MHz, DMSO-d6) δ ppm 11.55 (1H, br. s.) 10.24 (1H, s) 8.79 (1H, d, J=8.44 Hz) 8.02 (1H, d, J=5.42 Hz) 7.85 (1H, d, J=5.47 Hz) 7.51 (1H, d, J=5.47 Hz) 7.44 (2H, d, J=7.18 Hz) 7.22-7.39 (4H, m) 6.84 (1H, d, J=5.47 Hz) 6.41 (1H, dd, J=3.47, 1.22 Hz) 5.46 (1H, td, J=8.63, 6.47 Hz) 3.01-3.22 (2H, m)

IC$_{50}$ (p70S6K) "+++"

116. 2-(1H-Pyrrolo[2,3-b]pyridin-4-ylamino)-thiophene-3-carboxylic acid (cyano-phenyl-methyl)-amide

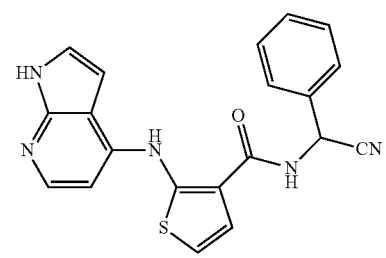 [SMILES: N#CC(NC(=O)c1ccsc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using amino(phenyl)acetonitrile instead of 1-BOC-3-aminopyrrolidine. LCMS (ESI) 374 (M+H) 1H NMR (400 MHz, DMSO-d6) δ ppm 11.72 (1H, br. s.) 11.56 (1H, s) 9.49 (1H, d, J=8.05 Hz) 8.18 (1H, d, J=5.42 Hz) 7.53-7.60 (4H, m) 7.43-7.51 (3H, m) 7.40 (2H, dd, J=3.22, 2.68 Hz) 7.03 (1H, d, J=5.47 Hz) 6.97 (1H, dd, J=5.78, 0.61 Hz) 6.54 (1H, d, J=7.81 Hz) 6.47 (1H, dd, J=3.49, 1.88 Hz)

IC$_{50}$ (p70S6K) "+++"

117. 2-(1H-Pyrrolo[2,3-b]pyridin-4-ylamino)-thiophene-3-carboxylic acid ((S)-1-hydroxymethyl-3-methyl-butyl)-amide

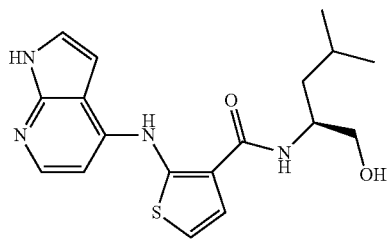 [SMILES: CC(C)C[C@@H](CO)NC(=O)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (2S)-2-amino-3-methylbutan-1-ol instead of 1-BOC-3-aminopyrrolidine. LCMS (ESI) 359 (M+H) 1H NMR (400 MHz, DMSO-d6) δ ppm 11.98 (1H, s) 11.65 (1H, br. s.) 8.14 (1H, d, J=5.52 Hz) 7.81 (1H, d, J=8.69 Hz) 7.57 (1H, d, J=5.91 Hz) 7.36 (1H, d, J=2.68 Hz) 6.96 (1H, d, J=5.47 Hz) 6.92 (1H, d, J=5.86 Hz) 6.45 (1H, dd, J=3.47, 1.90 Hz) 4.72 (1H, t, J=5.74 Hz) 4.13 (1H, td, J=9.77, 4.56 Hz) 3.42 (1H, t, J=5.49 Hz) 3.38 (1H, t, J=5.91 Hz) 1.62 (1H, dd, J=9.18, 5.12 Hz) 1.33-1.51 (2H, m) 0.89 (6H, dd, J=6.59, 1.56 Hz)

IC$_{50}$ (p70S6K) "+++"

118. 2-(1H-Pyrrolo[2,3-b]pyridin-4-ylamino)-thiophene-3-carboxylic acid ((S)-1-hydroxymethyl-2-phenyl-ethyl)-amide

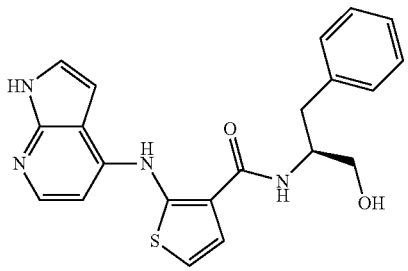 [SMILES: O=C(N[C@H](CO)Cc1ccccc1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (S)-phenylalaninol instead of 1-BOC-3-aminopyrrolidine. LCMS (ESI) 393 (M+H) 1H NMR (400 MHz, DMSO-d6) δ ppm 11.85 (1H, s) 11.65 (1H, br. s.) 8.13 (1H, d, J=5.52 Hz) 8.00 (1H, d, J=8.59 Hz) 7.55 (1H, d, J=5.81 Hz) 7.36 (1H, d, J=3.17 Hz) 7.20-7.30 (5H, m) 7.15 (1H, dt, J=6.96, 1.99 Hz) 6.95 (1H, d, J=5.47 Hz) 6.91 (1H, d, J=5.76 Hz) 6.42 (1H, dd, J=3.42, 1.81 Hz) 4.88 (1H, t, J=5.56 Hz) 4.17-4.31 (1H, m) 3.51 (1H, d, J=5.47 Hz) 3.46 (1H, t, J=5.88 Hz) 2.91-3.04 (1H, m) 2.81 (1H, dd, J=13.72, 9.42 Hz)

IC$_{50}$ (p70S6K) "+++"

119. 2-(1H-Pyrrolo[2,3-b]pyridin-4-ylamino)-thiophene-3-carboxylic acid ((R)-1-hydroxymethyl-2-phenyl-ethyl)-amide

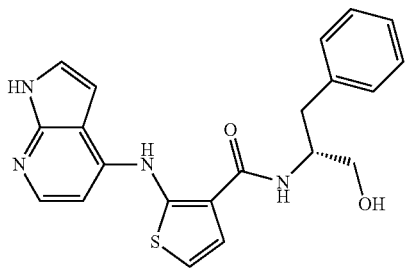 [SMILES: O=C(N[C@@H](CO)Cc1ccccc1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (R)-phenylalaninol instead of 1-BOC-3-aminopyrrolidine. LCMS (ESI) 393 (M+H) 1H NMR (400 MHz, DMSO-d6) δ ppm 11.85 (1H, s) 11.65 (1H, br. s.) 8.13 (1H, d, J=5.52 Hz) 7.99 (1H, d, J=8.59 Hz) 7.55 (1H, d, J=5.91 Hz) 7.36 (1H, dd, J=3.27, 2.64 Hz) 7.21-7.30 (5H, m) 7.15 (1H, dt, J=6.81, 2.18 Hz) 6.95 (1H, d, J=5.47 Hz) 6.91 (1H, d, J=6.25 Hz) 6.42 (1H, dd, J=3.49, 1.93 Hz) 4.88 (1H, t, J=5.66 Hz) 4.23 (1H, td, J=8.74, 5.32 Hz) 3.48-3.57 (1H, m) 3.46 (1H, t, J=5.61 Hz) 2.94-3.02 (1H, m) 2.81 (1H, dd, J=13.74, 9.20 Hz)

IC$_{50}$ (p70S6K) "++"

120. 3-(1H-Pyrrolo[2,3-b]pyridin-4-ylamino)-thiophene-2-carboxylic acid ((R)-2-carbamoyl-1-phenyl-ethyl)-amide

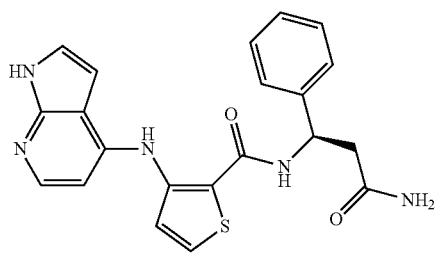 [SMILES: NC(=O)C[C@@H](NC(=O)c1sccc1Nc1ccnc2[nH]ccc12)c1ccccc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (3R)-3-amino-3-phenylpropanamide instead of 1-BOC-3-aminopyrrolidine. LCMS (ESI) 406 (M+H) 1H NMR (400 MHz, DMSO-d6) δ ppm 11.51 (1H, br. s.) 10.22 (1H, s) 8.65 (1H, d, J=8.44 Hz) 8.01 (1H, d, J=5.42 Hz) 7.80 (1H, d, J=5.47 Hz) 7.47 (1H, d, J=5.52 Hz) 7.33-7.39 (3H, m) 7.26-7.32 (4H, m) 7.17-7.23 (1H, m) 6.86 (1H, br. s.) 6.80 (1H, d, J=5.86 Hz) 6.40 (1H, d, J=3.56 Hz) 5.44 (1H, q, J=7.24 Hz) 2.66-2.75 (1H, m) 2.57-2.65 (1H, m)

IC$_{50}$ (p70S6K) "+++"

121. 2-(1H-Pyrrolo[2,3-b]pyridin-4-ylamino)-thiophene-3-carboxylic acid 3-chloro-4-trifluoromethyl-benzylamide

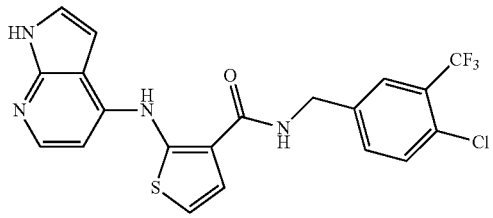 [SMILES: O=C(NCc1ccc(Cl)c(C(F)(F)F)c1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 1-[3-chloro-4-(trifluoromethyl)phenyl]methanamine instead of 1-BOC-3-aminopyrrolidine. LCMS (ESI) 451 (M+H) 1H NMR (400 MHz, DMSO-d6) δ ppm 11.79 (1H, s) 11.67 (1H, s) 8.94 (1H, t, J=6.13 Hz) 8.16 (1H, d, J=5.47 Hz) 7.86 (1H, d, J=2.00 Hz) 7.68-7.72 (1H, m) 7.61-7.68 (1H, m) 7.51 (1H, d, J=5.91 Hz) 7.37 (1H, dd, J=3.49, 2.51 Hz) 7.00 (1H, d, J=5.42 Hz) 6.96 (1H, dd, J=5.88, 0.61 Hz) 6.43 (1H, dd, J=3.49, 1.93 Hz) 4.59 (2H, d, J=5.86 Hz)

IC$_{50}$ (p70S6K) "+++"

122. 3-(1H-Pyrrolo[2,3-b]pyridin-4-ylamino)-thiophene-2-carboxylic acid (2-amino-1-p-tolyl-ethyl)-amide

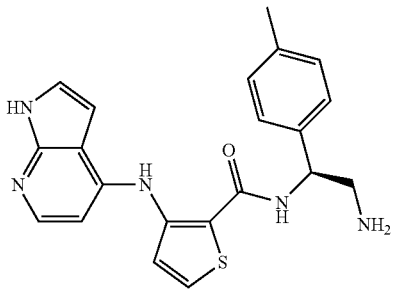 [SMILES: Cc1ccc([C@@H](CN)NC(=O)c2sccc2Nc2ccnc3[nH]ccc23)cc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-methylphenyl)ethyl]carbamate instead of 1-BOC-3-aminopyrrolidine. LCMS (ESI) 492 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 392 (M+H) 1H NMR (400 MHz, DMSO-d6) δ ppm 12.57 (1H, br. s.) 10.99 (1H, s) 9.26 (1H, d, J=8.30 Hz) 8.27 (3H, br. s.) 7.99 (1H, d, J=6.98 Hz) 7.92 (1H, d, J=5.27 Hz) 7.41 (1H, dd, J=3.08, 2.10 Hz) 7.28 (1H, d, J=5.17 Hz) 7.14 (2H, d, J=7.91 Hz) 7.03 (1H, br. s.) 6.90 (2H, d, J=7.86 Hz) 6.50 (1H, d, J=6.98 Hz) 5.25 (1H, dd, J=8.25, 6.10 Hz) 3.30-3.43 (1H, m) 3.07 (1H, t, J=11.47 Hz) 2.19 (3H, s)

IC$_{50}$ (p70S6K) "+++"

123. 3-(1H-Pyrrolo[2,3-b]pyridin-4-ylamino)-thiophene-2-carboxylic acid [2-amino-1-(3-methoxyphenyl)-ethyl]-amide

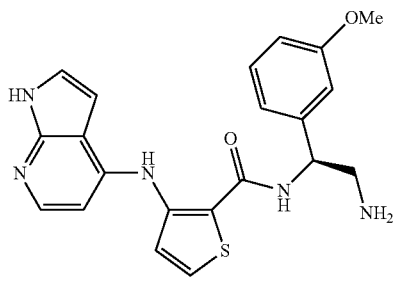 [SMILES: COc1cccc([C@@H](CN)NC(=O)c2sccc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-methoxyphenyl)ethyl] carbamate instead of 1-BOC-3-aminopyrrolidine. LCMS (ESI) 508 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 408 (M+H) 1H NMR (400 MHz, DMSO-d6) δ ppm 12.56 (1H, s) 11.01 (1H, s) 9.30 (1H, d, J=8.15 Hz) 8.27 (3H, br. s.) 8.00 (1H, d, J=6.88 Hz) 7.93 (1H, d, J=5.27 Hz) 7.39 (1H, d, J=2.59 Hz) 7.28 (1H, d, J=5.27 Hz) 7.03 (2H, t, J=7.88 Hz) 6.81-6.89 (2H, m) 6.75 (1H, dd, J=8.08, 2.51 Hz) 6.53 (1H, d, J=6.88 Hz) 5.27 (1H, dd, J=8.54, 5.71 Hz) 3.60 (3H, s) 3.37 (0H, dt, J=18.11, 5.34 Hz) 3.09-3.20 (1H, m) 3.05 (1H, qd, J=7.30, 4.66 Hz) IC$_{50}$ (p70S6K) "+++"

124. 3-(1H-Pyrrolo[2,3-b]pyridin-4-ylamino)-thiophene-2-carboxylic acid [2-amino-1-(3-chlorophenyl)-ethyl]-amide

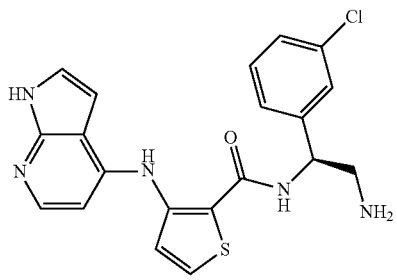 [SMILES: NC[C@@H](NC(=O)c1sccc1Nc1ccnc2[nH]ccc12)c1cccc(Cl)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-chlorophenyl)ethyl]carbamate instead of 1-BOC-3-aminopyrrolidine. LCMS (ESI) 512 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 412 (M+H) 1H NMR (400 MHz, DMSO-d6) δ ppm 12.54 (1H, br. s.) 10.99 (1H, s) 9.42 (1H, d, J=7.96 Hz) 8.32

(3H, br. s.) 8.01 (1H, d, J=6.88 Hz) 7.94 (1H, d, J=5.27 Hz) 7.39 (1H, dd, J=3.17, 2.34 Hz) 7.23-7.32 (4H, m) 7.19 (1H, d, J=8.00 Hz) 7.03 (1H, br. s.) 6.52 (1H, d, J=6.83 Hz) 5.31 (1H, dd, J=8.20, 5.61 Hz) 3.32-3.51 (2H, m) 3.10-3.24 (1H, m)

IC$_{50}$ (p70S6K) "+++"

125. 3-(1H-Pyrrolo[2,3-b]pyridin-4-ylamino)-thiophene-2-carboxylic acid [2-amino-1-(3,4-dichloro-phenyl)-ethyl]-amide

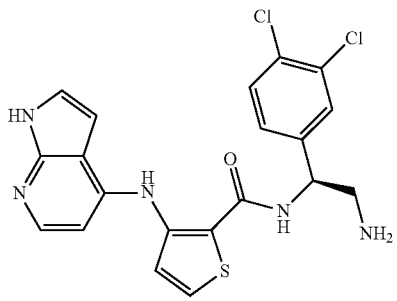 [SMILES: NC[C@@H](NC(=O)c1sccc1Nc1ccnc2[nH]ccc12)c1ccc(Cl)c(Cl)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3,4-dichlorophenyl)ethyl] carbamate instead of R)-2-(aminomethyl)-1-N-BOC-pyrrolidine. LCMS (ESI) 546 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 446 (M+H) 1H NMR (400 MHz, DMSO-d6) δ ppm 12.58 (1H, br. s.) 10.99 (1H, s) 9.49 (1H, d, J=7.86 Hz) 8.36 (3H, br. s.) 8.02 (1H, d, J=6.93 Hz) 7.94 (1H, d, J=5.22 Hz) 7.49 (1H, d, J=1.95 Hz) 7.38-7.44 (2H, m) 7.35 (1H, d, J=2.05 Hz) 7.27 (1H, d, J=5.27 Hz) 7.03 (1H, br. s.) 6.51 (1H, d, J=6.93 Hz) 5.32 (1H, td, J=8.71, 5.17 Hz) 3.32-3.47 (1H, m) 3.18 (1H, d, J=11.96 Hz)

IC$_{50}$ (p70S6K) "+++"

126. 2-(1H-Pyrrolo[2,3-b]pyridin-4-ylamino)-thiophene-3-carboxylic acid (2-amino-1-p-tolyl-ethyl)-amide

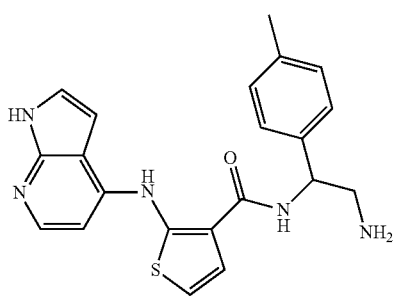 [SMILES: Cc1ccc(C(CN)NC(=O)c2ccsc2Nc2ccnc3[nH]ccc23)cc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(4-methylphenyl)ethyl]carbamate instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 492 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 392 (M+H) 1H NMR (400 MHz, DMSO-d6) δ ppm 12.61 (1H, br. s.) 11.45 (1H, s) 9.27 (1H, d, J=8.15 Hz) 8.26 (3H, br. s.) 8.08 (1H, d, J=6.83 Hz) 7.73 (1H, d, J=5.81 Hz) 7.38-7.48 (2H, m) 7.19 (2H, d, J=8.05 Hz) 6.97 (2H, d, J=7.96 Hz) 6.79 (1H, d, J=1.51 Hz) 6.67 (1H, d, J=6.78 Hz) 5.23 (1H, dt, J=14.33, 4.28 Hz) 3.27-3.45 (1H, m) 3.08 (1H, dd, J=7.17, 4.73 Hz) 2.22 (3H, s)

IC$_{50}$ (p70S6K) "+++"

127. 2-(1H-Pyrrolo[2,3-b]pyridin-4-ylamino)-thiophene-3-carboxylic acid [2-amino-1-(3-methoxy-phenyl)-ethyl]-amide

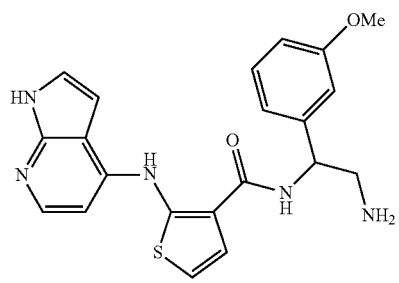 [SMILES: COc1cccc(C(CN)NC(=O)c2ccsc2Nc2ccnc3[nH]ccc23)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-methoxyphenyl)ethyl]carbamate instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 508 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 408 (M+H) 1H NMR (400 MHz, DMSO-d6) δ ppm 12.58 (1H, br. s.) 11.45 (1H, s) 9.30 (1H, d, J=8.20 Hz) 8.27 (3H, br. s.) 8.09 (1H, d, J=6.78 Hz) 7.76 (1H, d, J=5.81 Hz) 7.38-7.50 (2H, m) 7.11 (1H, t, J=7.83 Hz) 6.85-6.95 (2H, m) 6.75-6.82 (2H, m) 6.71 (1H, d, J=6.83 Hz) 5.26 (1H, dd, J=18.60, 4.00 Hz) 3.68 (3H, s) 3.37 (1H, t, J=8.64 Hz) 3.13 (1H, t, J=10.88 Hz) IC$_{50}$ (p70S6K) "+++"

128. 2-(1H-Pyrrolo[2,3-b]pyridin-4-ylamino)-thiophene-3-carboxylic acid [2-amino-1-(3,4-dichloro-phenyl)-ethyl]-amide

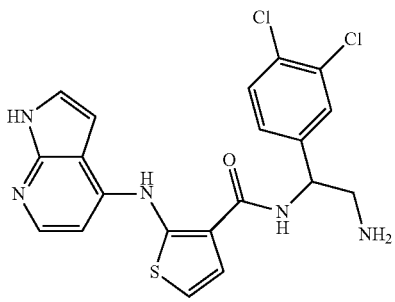 [SMILES: NCC(NC(=O)c1ccsc1Nc1ccnc2[nH]ccc12)c1ccc(Cl)c(Cl)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3,4-dichlorophenyl)ethyl]carbamate instead of 1-BOC-3-aminopyrrolidine and 2-(1H-Pyrrolo[2,3-b]pyridin-4-ylamino)-thiophene-3-carboxylic acid instead of 3-(1H-Pyrrolo[2,3-b]pyridin-4-ylamino)-thiophene-2-carboxylic acid. LCMS (ESI) 546 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 446 (M+H) 1H NMR (400 MHz, DMSO-d6) δ ppm 12.52 (1H, br. s.) 11.35 (1H, s) 9.39 (1H, d, J=7.86 Hz) 8.27 (3H, br. s.) 8.11 (1H, d, J=6.74 Hz) 7.75 (1H, d, J=5.81 Hz) 7.59 (1H, d, J=2.00 Hz) 7.42-7.50 (4H, m) 7.36 (1H, dd, J=8.22, 2.27 Hz) 6.75 (1H, d, J=3.27 Hz) 6.70 (1H, d, J=6.78 Hz) 5.29 (1H, ddd, J=12.69, 4.86, 4.56 Hz) 3.39 (1H, t, J=13.89 Hz) 3.11-3.26 (1H, m) IC$_{50}$ (p70S6K) "+++"

129. 2-Chloro-N-[3-({[3-(1H-pyrrolo[2,3-b]pyridin-4-ylamino)-thiophene-2-carbonyl]-amino}-methyl)-phenyl]-isonicotinamide

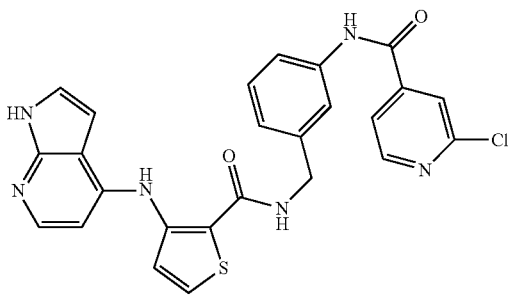 [SMILES: O=C(Nc1cccc(CNC(=O)c2sccc2Nc2ccnc3[nH]ccc23)c1)c1ccnc(Cl)c1]

Synthesis of N-[3-(aminomethyl)phenyl]-2-chloro-pyridine-4-carboxamide

A solution of 3-aminobenzylamine (10 g, 82 mmol), diisopropylethylamine (29 mL, 164 mmol) in methylene chloride (275 mL) was cooled to 0° C., followed by addition of Boc$_2$O (18 g, 82 mmol) in 4 portions. The reaction was allowed to stir at room temperature for 18 h. The reaction solution was washed with aqueous NH$_4$Cl, dried with Na$_2$SO$_4$, filtered and concentrated to dryness to afford tert-butyl (3-aminobenzyl) carbamate as a dark oil (26 g, 99%).

To a solution of 2-isonicotinic acid (1.0 g, 6.3 mmol) in DMF (20 mL) was added diisopropylethylamine (5.0 mL, 25 mmol), HATU (2.6 g, 6.9 mmol) followed by the above aniline (1.3 g, 5.8 mmol). The reaction was stirred at room temperature for 18 h then diluted with ethyl acetate. The organic layer was washed with aqueous 1% LiCl solution, dried over sodium sulfate, filtered and concentrated to dryness without any further purification to afford tert-butyl (3-{[(2-chloropyridin-4yl)carbonyl]amino}benzyl)carbamate.

To a solution of tert-butyl (3-{[(2-chloropyridin-4 yl)carbonyl]amino}benzyl)carbamate in methylene chloride (10 mL) at 0° C. was added 4 M HCl in dioxane (10 mL). The solution was allowed to warm to room temperature and stirred for 18 h. The reaction was concentrated in vacuo to dryness. Methanol was added and removed in vacuo (3x) to afford N-[3-(aminomethyl)phenyl]-2-chloropyridine-4-carboxamide.

This compound was prepared in an analogous manner as 3-(1H-Pyrrolo[2,3-b]pyridin-4-ylamino)-thiophene-2-carboxylic acid (2-amino-ethyl)-amide using N-[3-(aminomethyl)phenyl]-2-chloropyridine-4-carboxamide instead of tert-butyl-2-amino ethyl carbamate. LCMS (ESI) 503 (M+H) 1H NMR (400 MHz, DMSO-d6) δ ppm 11.53 (1H, br. s.) 10.56 (1H, s) 10.38 (1H, s) 8.73 (1H, t, J=6.05 Hz) 8.59 (1H, d, J=4.88 Hz) 8.03 (1H, d, J=5.47 Hz) 7.97 (1H, s) 7.84 (1H, dd, J=5.17, 1.27 Hz) 7.81 (1H, d, J=5.47 Hz) 7.66-7.72 (1H, m) 7.52 (1H, d, J=5.47 Hz) 7.28-7.36 (1H, m) 7.11 (1H, d, J=7.61 Hz) 6.86 (1H, d, J=5.27 Hz) 6.42 (1H, d, J=3.51 Hz) 4.48 (2H, d, J=5.86 Hz)

IC$_{50}$ (p70S6K) "+++"

130. 2-(1H-Pyrrolo[2,3-b]pyridin-4-ylamino)-thiophene-3-carboxylic acid [2-amino-1-(3-chloro-phenyl)-ethyl]-amide

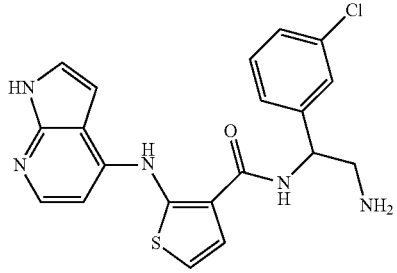 [SMILES: NCC(NC(=O)c1ccsc1Nc1ccnc2[nH]ccc12)c1cccc(Cl)c1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(3-chlorophenyl)ethyl]carbamate instead of 1-BOC-3-aminopyrrolidine. LCMS (ESI) 512 (M+H)

Followed by deprotection in an analogous manner as 3-(1H-Pyrrolo[2,3-b]pyridin-4-ylamino)-thiophene-2-carboxylic acid ((R)-1-pyrrolidin-2-ylmethyl)-amide. LCMS (ESI) 412 (M+H) 1H NMR (400 MHz, DMSO-d6) δ ppm 12.57 (1H, br. s.) 11.37 (1H, s) 9.38 (1H, d, J=8.00 Hz) 8.29 (3H, br. s.) 8.09 (1H, d, J=6.74 Hz) 7.75 (1H, d, J=5.86 Hz) 7.47 (1H, d, J=5.76 Hz) 7.43 (1H, dd, J=2.98, 2.49 Hz) 7.37

(1H, s) 7.16-7.34 (3H, m) 6.78 (1H, d, J=2.44 Hz) 6.69 (1H, d, J=6.74 Hz) 5.28 (1H, ddd, J=10.03, 8.03, 3.71 Hz) 3.17 (1H, dd, J=10.74, 7.42 Hz)

IC$_{50}$ (p70S6K) "+++"

131. 3-(1H-Pyrrolo[2,3-b]pyridin-4-ylamino)-thiophene-2-carboxylic acid [2-(1-phenyl-ethylamino)-ethyl]-amide

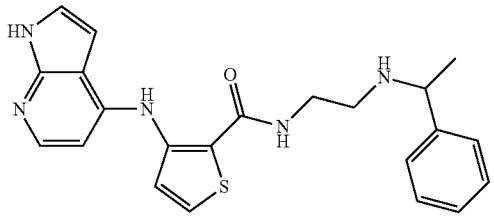 [SMILES: CC(NCCNC(=O)c1sccc1Nc1ccnc2[nH]ccc12)c1ccccc1]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using acetophenone instead of 4-methoxy benzaldehyde. LCMS (ESI) 406 (M+H) 1H NMR (400 MHz, DMSO-d6) δ ppm 11.53 (1H, br. s.) 10.22 (1H, s) 8.02 (2H, d, J=5.37 Hz) 7.76 (1H, d, J=5.37 Hz) 7.45 (1H, d, J=5.47 Hz) 7.21-7.34 (5H, m) 7.08-7.20 (1H, m) 6.79 (1H, d, J=5.37 Hz) 6.43 (1H, d, J=2.73 Hz) 3.67 (1H, q, J=6.51 Hz) 3.18-3.38 (2H, m) 2.34-2.58 (2H, m) 2.14 (1H, br. s.) 1.19 (3H, d, J=6.64 Hz)

IC$_{50}$ (p70S6K) "+++"

132. 3-(1H-Pyrrolo[2,3-b]pyridin-4-ylamino)-thiophene-2-carboxylic acid [2-amino-1-(4-trifluoromethyl-phenyl)-ethyl]-amide

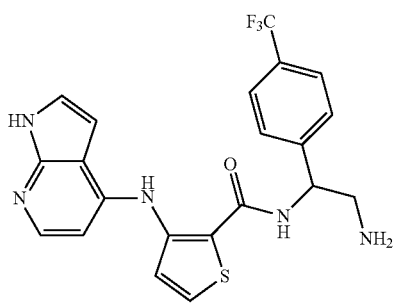 [SMILES: NCC(NC(=O)c1sccc1Nc1ccnc2[nH]ccc12)c1ccc(C(F)(F)F)cc1]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(4-trifluoromethylphenyl)ethyl]carbamate instead of 1-BOC-3-aminopyrrolidine. LCMS (ESI) 446 (M+H) 1H NMR (400 MHz, DMSO-d6) δ ppm 12.48 (1H, br. s.) 10.92 (1H, s) 9.40 (1H, d, J=8.00 Hz) 8.28 (3H, br. s.) 8.01 (1H, d, J=6.83 Hz) 7.95 (1H, d, J=5.27 Hz) 7.53-7.58 (2H, m) 7.47-7.52 (2H, m) 7.43 (1H, d, J=2.54 Hz) 7.31 (1H, d, J=5.27 Hz) 7.00 (1H, br. s.) 6.55 (1H, d, J=7.03 Hz) 5.39 (1H, td, J=8.79, 4.30 Hz) 3.19 (1H, t, J=10.93 Hz)

IC$_{50}$ (p70S6K) "+++"

133. 2-(1H-Pyrrolo[2,3-b]pyridin-4-ylamino)-thiophene-3-carboxylic acid [2-amino-1-(4-trifluoromethyl-phenyl)-ethyl]-amide

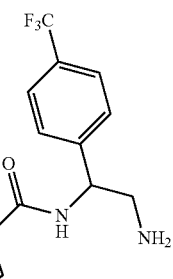

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using tert-butyl [2-amino-2-(4-trifluoromethylphenyl)ethyl]carbamate instead of 1-BOC-3-aminopyrrolidine. LCMS (ESI) 446 (M+H) 1H NMR (400 MHz, DMSO-d6) δ ppm 12.54 (1H, br. s.) 11.40 (1H, s) 9.45 (1H, d, J=8.00 Hz) 8.32 (3H, br. s.) 8.10 (1H, d, J=6.74 Hz) 7.78 (1H, d, J=5.86 Hz) 7.57 (4H, q, J=8.53 Hz) 7.45 (2H, d, J=5.66 Hz) 6.78 (1H, d, J=3.42 Hz) 6.69 (1H, d, J=6.83 Hz) 5.37 (1H, dd, J=18.40, 3.76 Hz) 3.43 (2H, dd, J=6.83, 6.25 Hz) 3.21 (1H, dd, J=5.56, 5.27 Hz)

IC$_{50}$ (p70S6K) "+++"

134. (S)-[3-(1H-Pyrrolo[2,3-b]pyridin-4-ylamino)-thiophene-2-carboxylic acid[2-(1,3-dioxo-1,3-dihydro-isoindol-2-yl)-1-phenyl-ethyl]-amide]

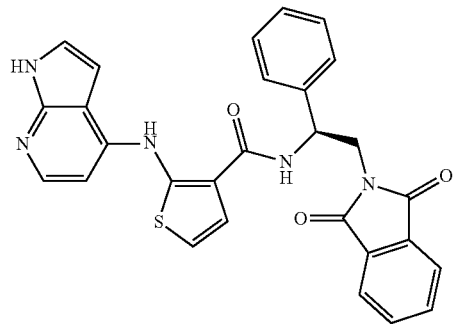 [SMILES: O=C(N[C@H](CN1C(=O)c2ccccc2C1=O)c1ccccc1)c1ccsc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-[(2S)-2-amino-2-phenylethyl]-1H-isoindole-1,3(2H)-dione instead of 1-BOC-3-aminopyrrolidine. LCMS (ESI) 508 (M+H) 1H NMR (400 MHz, DMSO-d6) δ ppm 11.63 (1H, br. s.) 11.48 (1H, s) 8.68 (1H, d, J=9.08 Hz) 8.11 (1H, d, J=5.47 Hz) 7.78-7.83 (2H, m) 7.73 (2H, dd, J=5.39, 3.10 Hz) 7.59 (1H, d, J=5.91 Hz) 7.48 (2H, d, J=7.32 Hz) 7.33 (3H, t, J=6.59 Hz) 7.23-7.29 (1H, m) 6.93 (2H, dd, J=7.35, 5.64 Hz) 6.22 (1H, dd, J=3.47, 1.85 Hz) 5.55-5.64 (1H, m) 4.02-4.11 (2H, m)

IC$_{50}$ (p70S6K) "+++"

135. (S)-2-(1H-Pyrrolo[2,3-b]pyridin-4-ylamino)-thiophene-3-carboxylic acid[2-(1,3-dioxo-1,3-dihydro-isoindol-2-yl)-1-phenyl-ethyl]-amide

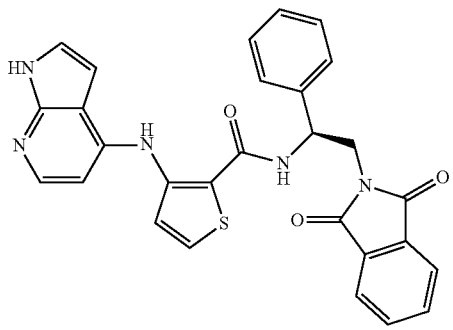 [SMILES: O=C(N[C@H](CN1C(=O)c2ccccc2C1=O)c1ccccc1)c1sccc1Nc1ccnc2[nH]ccc12]

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using 2-[(2S)-2-amino-2-phenylethyl]-1H-isoindole-1,3(2H)-dione instead of 1-BOC-3-aminopyrrolidine. LCMS (ESI) 508 (M+H) 1H NMR (400 MHz, DMSO-d6) δ ppm 11.50 (1H, br. s.) 9.96 (1H, s) 8.61 (1H, d, J=8.69 Hz) 7.98 (1H, d, J=5.47 Hz) 7.79 (3H, dd, J=5.42, 4.44 Hz) 7.68-7.74 (2H, m) 7.38-7.46 (3H, m) 7.18-7.33 (4H, m) 6.74 (1H, d, J=5.47 Hz) 6.25 (1H, dd, J=3.47, 1.81 Hz) 5.47-5.57 (1H, m) 4.05 (2H, d).

IC$_{50}$ (p70S6K) "+++"

136. 3-(1H-Pyrrolo[2,3-b]pyridin-4-ylamino)-thiophene-2-carboxylic acid [2-(4-methyl-benzylamino)-ethyl]-amide

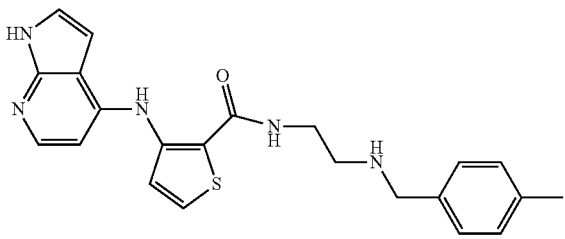 [SMILES: Cc1ccc(CNCCNC(=O)c2sccc2Nc2ccnc3[nH]ccc23)cc1]

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 4-methylbenzaldehyde instead of 4-methoxy benzaldehyde. LCMS (ESI) 406 (M+H) $^1$H NMR (400 MHz, DMSO-d$_6$) δ ppm 11.43-11.53 (1H, m) 10.24 (1H, s) 7.95-8.04 (1H, m) 7.75 (1H, d, J=5.47 Hz) 7.44 (1H, d, J=5.47 Hz) 7.25-7.31 (1H, m) 7.14 (1H, d, J=8.00 Hz) 7.03 (1H, d, J=7.81 Hz) 6.77 (1H, d, J=5.47 Hz) 6.41 (1H, dd, J=3.42, 1.85 Hz) 3.60 (2H, s) 3.31-3.36 (2H, m) 2.58 (2H, t, J=6.54 Hz) 2.22 (3H, s)

IC$_{50}$ (p70S6K) "+++"

137. 3-(1H-Pyrrolo[2,3-b]pyridin-4-ylamino)-thiophene-2-carboxylic acid [2-(3-chloro-4-methoxy-benzylamino)-ethyl]-amide

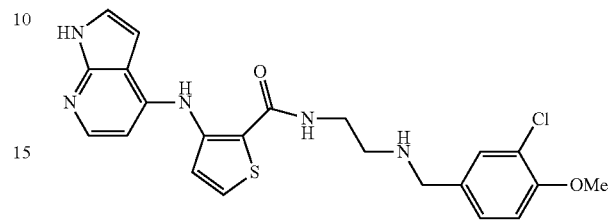

This compound was prepared in an analogous manner as 3-(1H-Pyrrolo[2,3-b]pyridin-4-ylamino)-thiophene-2-carboxylic acid [2-(4-methoxy-benzylamino)-ethyl]amide using 3-chloro-4-methoxybenzaldehyde instead of 4-methoxy benzaldehyde. LCMS (ESI) 456 (M+H) 1H NMR (400 MHz, DMSO-d6) δ ppm 11.52 (1H, br. s.) 10.28 (1H, s) 7.98-8.07 (2H, m) 7.77 (1H, d, J=5.42 Hz) 7.46 (1H, d, J=5.42 Hz) 7.36 (1H, d, J=2.15 Hz) 7.30 (1H, dd, J=3.51, 2.39 Hz) 7.20 (1H, dd, J=8.42, 2.12 Hz) 7.00 (1H, d, J=8.44 Hz) 6.80 (1H, d, J=5.52 Hz) 6.43 (1H, dd, J=3.54, 1.88 Hz) 3.80 (3H, s) 3.61 (2H, s) 2.60 (2H, t, J=6.59 Hz)

IC$_{50}$ (p70S6K) "+++"

138. {[3-(1H-Pyrrolo[2,3-b]pyridin-4-ylamino)-thiophene-2-carbonyl]-amino}-acetic acid methyl ester

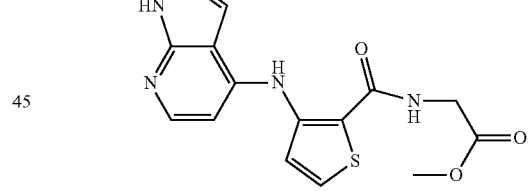

This compound was prepared in an analogous manner as 3-(1H-Pyrrolo[2,3-b]pyridin-4-ylamino)-thiophene-2-carboxylic acid (2-amino-ethyl)-amide using amino-acetic acid methyl ester instead of tert-butyl-2-amino ethyl carbamate. LCMS (ESI) 331 (M+H) 1H NMR (400 MHz, DMSO-d6) δ ppm 11.55 (1H, br. s.) 10.22 (1H, s) 8.54 (1H, t, J=5.76 Hz) 8.04 (1H, d, J=5.42 Hz) 7.83 (1H, d, J=5.42 Hz) 7.51 (1H, d, J=5.47 Hz) 7.32 (1H, dd, J=3.49, 2.37 Hz) 6.86 (1H, d, J=5.47 Hz) 6.41 (1H, dd, J=3.54, 1.83 Hz) 4.00 (2H, d, J=5.81 Hz) 3.66 (3H, d, J=0.10 Hz)

IC$_{50}$ (p70S6K) "++"

139. 2-(1H-Pyrrolo[2,3-b]pyridin-4-ylamino)-thiophene-3-carboxylic acid ((R)-2-cyano-1-phenyl-ethyl)-amide

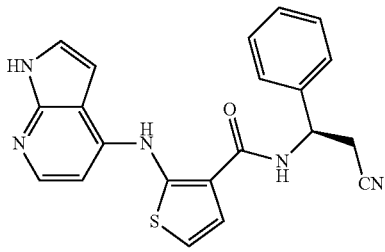

This compound was prepared in an analogous manner as 3-{[3-(1H-Pyrrolo[2,3-b]pyridin-4-ylamino)-thiophene-2-carbonyl]-amino}-pyrrolidine-1-carboxylic acid tert-butyl ester using (3R)-3-amino-3-phenylpropanenitrile (*Organic Synthesis* 2008, 85, 219-230) instead of 1-BOC-3-aminopyrrolidine. LCMS (ESI) 388 (M+H) 1H NMR (400 MHz, DMSO-d6) δ ppm 11.64-11.76 (2H, m) 8.87 (1H, d, J=8.44 Hz) 8.15 (1H, d, J=5.61 Hz) 7.62 (1H, d, J=6.15 Hz) 7.48 (2H, d, J=7.18 Hz) 7.35-7.41 (4H, m) 7.27-7.33 (1H, m) 6.99 (2H, t, J=5.00 Hz) 6.44 (1H, dd, J=3.12, 2.00 Hz) 5.47-5.60 (1H, m) 3.06-3.22 (2H, m)

IC$_{50}$ (p70S6K) "+++"

140. 2-(1H-Pyrrolo[2,3-b]pyridin-4-ylamino)-thiophene-3-carboxylic acid ((S)-2-amino-1-phenyl-ethyl)-amide

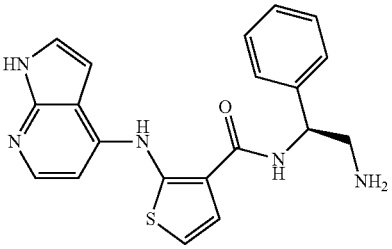 [SMILES: NC[C@@H](NC(=O)c1ccsc1Nc1ccnc2[nH]ccc12)c1ccccc1]

To a solution of 2-(1H-Pyrrolo[2,3-b]pyridin-4-ylamino)-thiophene-3-carboxylic acid ((S)-2-azido-1-phenyl-ethyl)-amide (40 mg, 0.1 mmol), 5% Pd/C (cat) in methanol (5 mL) was subjected to an atmosphere of hydrogen (balloon). After completion the solution was filtered and concentrated in vacuo. The residue was purified by ISCO Companion (silica, 10% methanol, methylene chloride, 1% ammonium hydroxide) to afford 2-(1H-Pyrrolo[2,3-b]pyridin-4-ylamino)-thiophene-3-carboxylic acid ((S)-2-amino-1-phenyl-ethyl)-amide (35 mg) (ESI) 378 (M+H) 1H NMR (400 MHz, DMSO-d6) δ ppm 12.61 (1H, br. s.) 11.45 (1H, s) 9.32 (1H, d, J=8.20 Hz) 8.28 (3H, br. s.) 8.08 (1H, d, J=6.88 Hz) 7.75 (1H, d, J=5.81 Hz) 7.47 (2H, d, J=5.86 Hz) 7.33 (2H, dd, J=7.57, 1.81 Hz) 7.12-7.24 (3H, m) 6.81 (1H, dd, J=2.49, 1.22 Hz) 6.68 (1H, d, J=6.88 Hz) 5.28 (1H, dd, J=10.54, 4.73 Hz) 3.40 (1H, td, J=11.53, 5.44 Hz) 3.12 (1H, dd, J=7.39, 4.61 Hz)

IC$_{50}$ (p70S6K) "+++"

158. 3-(1H-Pyrrolo[2,3-b]pyridin-4-ylamino)-thiophene-2-carboxylic acid [2-dimethylamino-1-(2-methoxy-phenyl)-ethyl]-amide

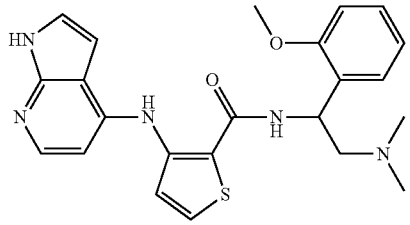 [SMILES: COc1ccccc1C(CN(C)C)NC(=O)c1sccc1Nc1ccnc2[nH]ccc12]

To a 40-mL vial with magnetic stir bar at 25° C. under a nitrogen atmosphere was added 3-(1H-Pyrrolo[2,3-b]pyridin-4-ylamino)-thiophene-2-carbonyl chloride (0.26 g, 0.94 mmol) and anhydrous DCM (8 mL). 1-(2-Methoxy-phenyl)-N*2*,N*2*-dimethyl-ethane-1,2-diamine (0.2 g, 1.0 mmol) was then added followed by the diisopropylethylamine (0.6 g, 0.8 mL, 4.7 mmol) and stirring continued×16 hours. The solvent was evaporated under a nitrogen stream and the resulting residue purified via preparative HPLC (0.1% triethylamine/1% acetonitrile mixture in water and methanol) afforded the desired product as a white solid (59.1 mg, 14% yield). LCMS m/e 436 (M+H). $^1$H NMR (400 MHz, DMSO-d$_6$) ppm 2.12 (s, 6H) 2.25 (dd, J=12.38, 4.27 Hz, 1H) 2.60 (dd, J=12.34, 9.78 Hz, 1H) 3.77 (s, 3H) 5.44-5.52 (m, 1H) 6.41 (dd, J=3.36, 1.18 Hz, 1H) 6.66 (d, J=5.44 Hz, 1H) 6.84 (td, J=7.42, 0.71 Hz, 1H) 6.92-6.97 (m, 1H) 7.16-7.22 (m, 1H) 7.24 (dd, J=7.57, 1.56 Hz, 1H) 7.26-7.28 (m, 1H) 7.39 (d, J=5.39 Hz, 1H) 7.81 (d, J=5.38 Hz, 1H) 7.98 (d, J=5.41 Hz, 1H) 8.23 (d, J=7.92 Hz, 1H) 9.89 (s, 1H) 11.49 (br s, 1H).

IC$_{50}$ (p70S6K) "++"

159. 3-(1H-Pyrrolo[2,3-b]pyridin-4-ylamino)-thiophene-2-carboxylic acid [1-(3-chloro-phenyl)-2-dimethylamino-ethyl]-amide

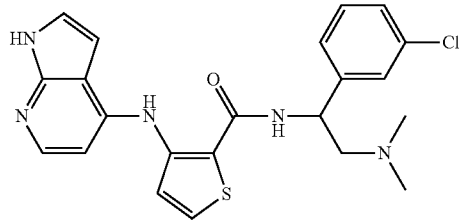 [SMILES: CN(C)CC(NC(=O)c1sccc1Nc1ccnc2[nH]ccc12)c1cccc(Cl)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 440 (M+H). $^1$H NMR (400 MHz, DMSO-d$_6$) ppm 2.13 (s, 6H) 2.39 (dd, J=12.39, 5.64 Hz, 1H) 2.65 (dd, J=12.32, 9.51 Hz, 1H) 5.07-5.16 (m, 1H) 6.40 (d, J=3.47 Hz, 1H) 6.72 (d, J=5.22 Hz, 1H) 7.25-7.30 (m, 2H) 7.30-7.34 (m, 2H) 7.43 (d, J=5.33 Hz, 1H) 7.46 (s, 1H) 7.82 (d, J=5.36 Hz, 1H) 8.00 (d, J=4.61 Hz, 1H) 8.36 (d, J=5.67 Hz, 1H) 10.03 (s, 1H) 11.50 (br s, 1H).

IC$_{50}$ (p70S6K) "+++"

160. 3-(1H-Pyrrolo[2,3-b]pyridin-4-ylamino)-
thiophene-2-carboxylic acid [2-dimethylamino-1-(3-
methoxy-phenyl)-ethyl]-amide

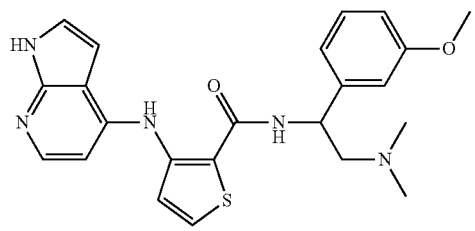 [SMILES: COc1cccc(C(CN(C)C)NC(=O)c2sccc2Nc2ccnc3[nH]ccc23)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 436 (M+H). $^1$H NMR (400 MHz, DMSO-d$_6$) ppm 2.13 (s, 6H) 2.35 (dd, J=12.36, 5.15 Hz, 1H) 2.65-2.74 (m, 1H) 3.71 (s, 3H) 5.06-5.14 (m, 1H) 6.40 (d, J=3.42 Hz, 1H) 6.72 (d, J=5.39 Hz, 1H) 6.78 (dd, J=7.95, 2.19 Hz, 1H) 6.92 (d, J=7.69 Hz, 1H) 6.96 (s, 1H) 7.20 (t, J=7.89 Hz, 1H) 7.28 (d, J=2.90 Hz, 1H) 7.43 (d, J=5.30 Hz, 1H) 7.81 (d, J=5.34 Hz, 1H) 7.99 (d, J=5.34 Hz, 1H) 8.31 (d, J=7.31 Hz, 1H) 10.07 (s, 1H) 11.50 (br s, 1H).

IC$_{50}$ (p70S6K) "+++"

161. 2-Pyrrolidin-1-yl-N-[3-({[3-(1H-pyrrolo[2,3-b]
pyridin-4-ylamino)-thiophene-2-carbonyl]-amino}-
methyl)-phenyl]-isonicotinamide

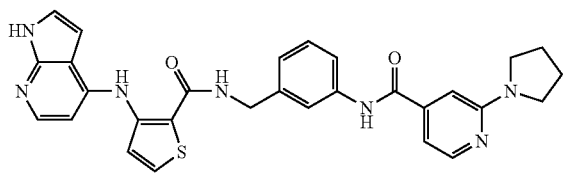 [SMILES: O=C(Nc1cccc(CNC(=O)c2sccc2Nc2ccnc3[nH]ccc23)c1)c1ccnc(N2CCCC2)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 538 (M+H). 1H NMR (400 MHz, DMSO-d6) ppm 11.53 (1H, br s) 10.39 (1H, s) 10.28 (1H, s) 8.72 (1H, s) 8.18 (1H, d, J=5.08 Hz) 8.03 (1H, d, J=5.27 Hz) 7.81 (1H, d, J=5.47 Hz) 7.70 (1H, s) 7.67 (1H, d, J=8.20 Hz) 7.51 (1H, d, J=5.86 Hz) 7.27-7.33 (2H, m) 7.08 (1H, d, J=8.40 Hz) 6.95 (1H, d, J=5.08 Hz) 6.83-6.88 (2H, m) 6.43 (1H, br s) 4.47 (2H, d, J=5.86 Hz) 3.40-3.45 (4H, m) 1.92-1.98 (4H, m).

IC$_{50}$ (p70S6K) "+++"

162. 2-Dimethylamino-N-[3-({[3-(1H-pyrrolo[2,3-b]
pyridin-4-ylamino)-thiophene-2-carbonyl]-amino}-
methyl)-phenyl]-isonicotinamide

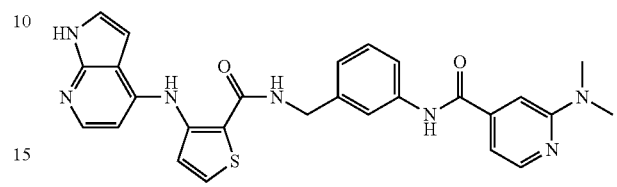

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 512 (M+H). $^1$H NMR (400 MHz, DMSO-d$_6$) ppm 3.07 (s, 6H) 4.47 (d, J=1.33 Hz, 2H) 6.42 (d, J=2.75 Hz, 1H) 6.85 (d, J=5.48 Hz, 1H) 6.98 (dd, J=5.16, 1.23 Hz, 1H) 7.02 (s, 1H) 7.08 (d, J=7.76 Hz, 1H) 7.27-7.33 (m, 2H) 7.51 (d, J=5.30 Hz, 1H) 7.67 (d, J=8.07 Hz, 1H) 7.70 (s, 1H) 7.80 (d, J=4.44 Hz, 1H) 8.02 (d, J=4.95 Hz, 1H) 8.20 (d, J=5.16 Hz, 1H) 8.72 (br s, 1H) 10.30 (br s, 1H) 10.38 (br s, 1H) 11.53 (br s, 1H).

IC$_{50}$ (p70S6K) "+++"

163. 2-(4-Methyl-piperazin-1-yl)-N-[3-({[3-(1H-
pyrrolo[2,3-b]pyridin-4-ylamino)-thiophene-2-carbo-
nyl]-amino}-methyl)-phenyl]-isonicotinamide

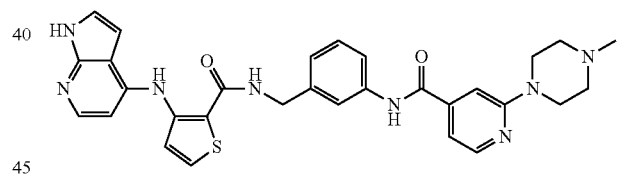

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 567 (M+H). $^1$H NMR (400 MHz, DMSO-d$_6$) ppm 2.21 (s, 3H) 2.37-2.40 (m, 4H) 3.51-3.57 (m, 4H) 4.47 (d, J=4.95 Hz, 2H) 6.42 (d, J=3.45 Hz, 1H) 6.85 (d, J=5.56 Hz, 1H) 7.04 (dd, J=5.15, 1.10 Hz, 1H) 7.08 (d, J=7.71 Hz, 1H) 7.22 (s, 1H) 7.27-7.33 (m, 2H) 7.51 (d, J=5.20 Hz, 1H) 7.67 (d, J=8.18 Hz, 1H) 7.70 (s, 1H) 7.81 (d, J=5.39 Hz, 1H) 8.02 (d, J=5.40 Hz, 1H) 8.23 (d, J=5.15 Hz, 1H) 8.73 (t, J=5.71 Hz, 1H) 10.32 (br s, 1H) 10.39 (s, 1H) 11.54 (br s, 1H).

IC$_{50}$ (p70S6K) "+++"

164. 2-Morpholin-4-yl-N-[3-({[3-(1H-pyrrolo[2,3-b]pyridin-4-ylamino)-thiophene-2-carbonyl]-amino}-methyl)-phenyl]-isonicotinamide

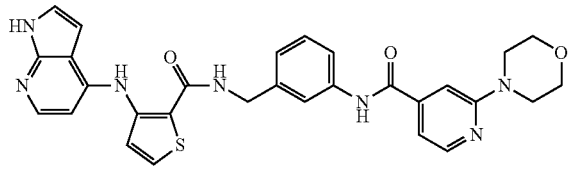 [SMILES: O=C(Nc1cccc(CNC(=O)c2sccc2Nc2ccnc3[nH]ccc23)c1)c1ccnc(N2CCOCC2)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 554 (M+H). $^1$H NMR (400 MHz, DMSO-d$_6$) ppm 3.48-3.53 (m, 4H) 3.68-3.73 (m, 4H) 4.47 (d, J=5.94 Hz, 2H) 6.42 (d, J=3.17 Hz, 1H) 6.86 (d, J=5.47 Hz, 1H) 7.06-7.11 (m, 2H) 7.22 (s, 1H) 7.28-7.33 (m, 2H) 7.51 (d, J=5.45 Hz, 1H) 7.67 (d, J=7.95 Hz, 1H) 7.70 (s, 1H) 7.81 (d, J=5.44 Hz, 1H) 8.03 (d, J=5.42 Hz, 1H) 8.26 (d, J=5.19 Hz, 1H) 8.72 (t, J=5.88 Hz, 1H) 10.33 (s, 1H) 10.39 (s, 1H) 11.53 (br s, 1H).

IC$_{50}$ (p70S6K) "+++"

165. 2-Ethylamino-N-[3-({[3-(1H-pyrrolo[2,3-b]pyridin-4-ylamino)-thiophene-2-carbonyl]-amino}-methyl)-phenyl]-isonicotinamide

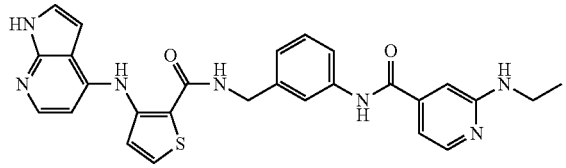 [SMILES: CCNc1cc(C(=O)Nc2cccc(CNC(=O)c3sccc3Nc3ccnc4[nH]ccc34)c2)ccn1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 512 (M+H). $^1$H NMR (400 MHz, DMSO-d$_6$) ppm 1.13 (t, J=7.19 Hz, 3H) 3.25-3.28 (m, 2H) 4.46 (d, J=5.36 Hz, 2H) 6.42 (d, J=2.81 Hz, 1H) 6.71-6.75 (m, 1H) 6.83 (s, 1H) 6.84-6.88 (m, 2H) 7.07 (d, J=6.67 Hz, 1H) 7.26-7.32 (m, 2H) 7.51 (d, J=5.46 Hz, 1H) 7.66 (d, J=8.55 Hz, 1H) 7.70 (s, 1H) 7.81 (d, J=4.84 Hz, 1H) 8.01-8.04 (m, 1H) 8.08 (d, J=5.22 Hz, 1H) 8.69-8.74 (m, 1H) 10.27 (s, 1H) 10.39 (s, 1H) 11.53 (br. s, 1H).

IC$_{50}$ (p70S6K) "+++"

166. 3-(1H-Pyrrolo[2,3-b]pyridin-4-ylamino)-thiophene-2-carboxylic acid [2-dimethylamino-1-(4-fluoro-phenyl)-ethyl]-amide

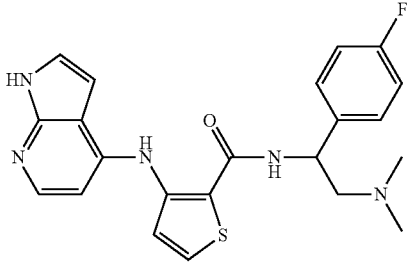 [SMILES: CN(C)CC(NC(=O)c1sccc1Nc1ccnc2[nH]ccc12)c1ccc(F)cc1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide. LCMS m/e 424 (M+H). $^{19}$F NMR (376 MHz, DMSO-d$_6$) ppm −116.53 (s, 1F). $^1$H NMR (400 MHz, DMSO-d$_6$) ppm 2.13 (s, 6H) 2.36 (dd, J=12.43, 5.69 Hz, 1H) 2.66 (dd, J=12.36, 9.56 Hz, 1H) 5.08-5.16 (m, 1H) 6.40 (d, J=3.46 Hz, 1H) 6.71 (d, J=5.21 Hz, 1H) 7.07-7.13 (m, 2H) 7.29 (d, J=3.11 Hz, 1H) 7.35-7.44 (m, 3H) 7.81 (d, J=4.92 Hz, 1H) 7.99 (d, J=5.28 Hz, 1H) 8.32 (d, J=6.87 Hz, 1H) 10.05 (s, 1H) 11.51 (br s, 1H).

IC$_{50}$ (p70S6K) "+++"

167. 3-(1H-Pyrrolo[2,3-b]pyridin-4-ylamino)-thiophene-2-carboxylic acid [1-(3-fluoro-phenyl)-2-methylamino-ethyl]-amide

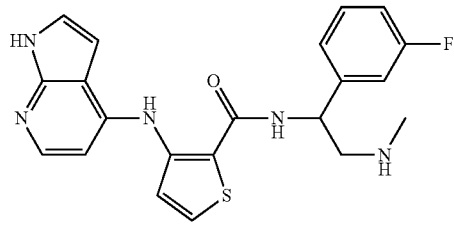 [SMILES: CNCC(NC(=O)c1sccc1Nc1ccnc2[nH]ccc12)c1cccc(F)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide followed by removal of the Boc protecting group with HCl/dioxane. LCMS m/e 410 (M+H). $^1$H NMR (400 MHz, CHLOROFORM-d) d ppm 10.14 (1H, d, J=8.20 Hz) 10.02 (1H, s) 8.07 (1H, d, J=5.47 Hz) 7.40 (2H, q, J=5.47 Hz) 7.32 (1H, td, J=7.91, 5.86 Hz) 7.24-7.28 (1H, m) 7.06-7.20 (4H, m) 6.92-7.01 (1H, m) 6.87 (1H, d, J=5.66 Hz) 6.54 (1H, d, J=3.51 Hz) 5.23-5.31 (1H, m) 2.93-3.19 (2H, m) 2.48 (3H, s).

IC$_{50}$ (p70S6K) "+++"

168. 3-(1H-Pyrrolo[2,3-b]pyridin-4-ylamino)-thiophene-2-carboxylic acid [1-(3-chloro-phenyl)-2-methylamino-ethyl]-amide

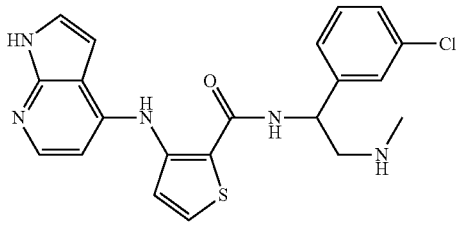 [SMILES: CNCC(NC(=O)c1sccc1Nc1ccnc2[nH]ccc12)c1cccc(Cl)c1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide followed by removal of the Boc protecting group with HCl/dioxane. LCMS m/e 426 (M+H) $^1$H NMR (400 MHz, DMSO-d6) ppm 11.50 (1H, br s) 10.06 (1H, br s) 8.00 (1H, d, J=5.47 Hz) 7.83 (1H, d, J=5.27 Hz) 7.41-7.55 (3H, m) 7.23-7.37 (5H, m) 6.74 (1H, d, J=5.47 Hz) 6.40 (1H, dd, J=3.51, 1.76 Hz) 5.13 (1H, m) 2.85 (1H, dd, J=12.30, 8.59 Hz) 2.66-2.74 (2H, m) 2.42 (2H, q, J=7.09 Hz).

IC$_{50}$ (p70S6K) "+++"

169. 3-(1H-Pyrrolo[2,3-b]pyridin-4-ylamino)-thiophene-2-carboxylic acid (2-methylamino-1-phenyl-ethyl)-amide

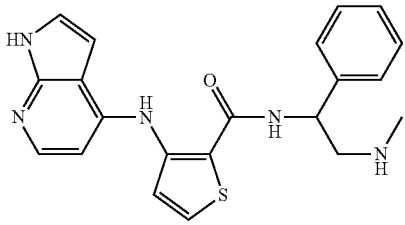 [SMILES: CNCC(NC(=O)c1sccc1Nc1ccnc2[nH]ccc12)c1ccccc1]

This compound was prepared in an analogous manner as 3-(1H-Pyrrolo[2,3-b]pyridin-4-ylamino)-thiophene-2-carboxylic acid [2-dimethylamino-1-(2-methoxy-phenyl)-ethyl]-amide followed by removal of the Boc protecting group with HCl/dioxane. LCMS m/e 392 (M+H) $^1$H NMR (400 MHz, CHLOROFORM-d) ppm 10.35 (1H, br s) 10.00 (1H, s) 8.11 (1H, d, J=5.47 Hz) 7.37-7.42 (1H, m) 7.30-7.37 (5H, m) 7.20-7.28 (2H, m) 7.16 (1H, d, J=3.71 Hz) 6.98 (1H, d, J=6.83 Hz) 6.85 (1H, d, J=5.66 Hz) 6.55 (1H, d, J=3.71 Hz) 5.24 (1H, q, J=5.99 Hz) 2.88-3.11 (2H, m) 2.39-2.45 (3H, m).

IC$_{50}$ (p70S6K) "+++"

3-(1H-Pyrrolo[2,3-b]pyridin-4-ylamino)-thiophene-2-carboxylic acid ((S)-2-azido-1-phenyl-ethyl)-amide (building block)

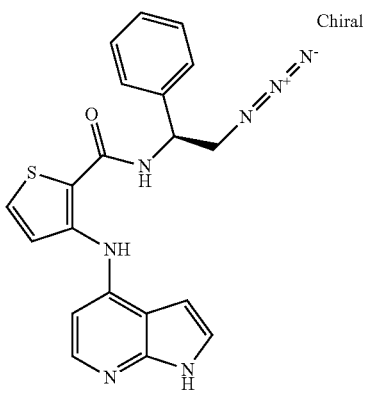 [SMILES: [N-]=[N+]=NC[C@@H](NC(=O)c1sccc1Nc1ccnc2[nH]ccc12)c1ccccc1]

To a solution of 3-(1H-pyrrolo[2,3-b]pyridin-4-ylamino)thiophene-2-carboxylic acid (130.00 mg; 0.50 mmol; 1.00 eq.), (1S)-2-azido-1-phenylethanamine (129.67 mg; 0.55 mmol; 1.10 eq.), n,n-diisopropylethylamine (0.33 ml; 2.01 mmol; 4.00 eq.) in DMF (2.00 ml), O-(7-azabenzotriazol-1-yl)-n,n,n',n'-tetramethyluronium hexafluoro-phosphate (209.70 mg; 0.55 mmol; 1.10 eq.) was added. The resulting mixture was stirred at room temperature for 1 hour. The reaction mixture was poured into water. The solid was too tiny to be filtered. The aqueous mixture was extracted with ethyl acetate to afford the title compound in 79% yield. LCMS: m/e 404 (M+H). $^1$H NMR (DMSO-d$_6$): ppm 11.56 (1H, br, s.), 10.25 (1H, s.), 8.72 (1H, d, J=8.44 Hz), 8.02 (1H, d, J=5.48 Hz), 7.85 (1H, d, J=5.52 Hz), 7.50 (1H, d, J=5.48 Hz), 7.42-7.44 (1H, m), 7.26-7.35 (4H, m), 6.81 (1H, d, J=5.16 Hz), 6.40 (1H, dd, J=3.28, 1.84 Hz), 5.27-5.32 (1H, m), 3.79 (1H, dd, J=12.84, 9.52 Hz), 3.60 (1H, dd, J=12.48, 4.76 Hz).

3-(1H-Pyrrolo[2,3-b]pyridin-4-ylamino)-thiophene-2-carboxylic acid [(S)-2-azido-1-(3-fluoro-phenyl)-ethyl]-amide (building block)

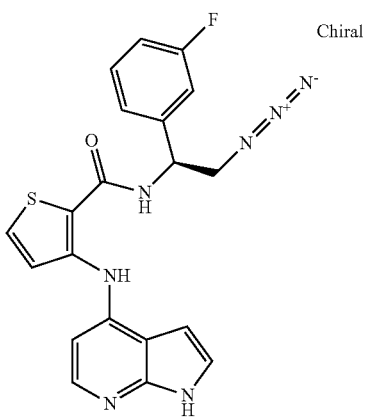 [SMILES: [N-]=[N+]=NC[C@@H](NC(=O)c1sccc1Nc1ccnc2[nH]ccc12)c1cccc(F)c1]

The title compound was prepared in an analogous manner as 3-(1H-Pyrrolo[2,3-b]pyridin-4-ylamino)-thiophene-2- carboxylic acid ((S)-2-azido-1-phenyl-ethyl)-amide in 71% yield. LCMS: m/e 422 (M+H). $^1$H NMR (DMSO-d$_6$): ppm 11.56 (1H, br, s.), 10.23 (1H, s.), 8.73 (1H, d, J=8.44 Hz), 8.02 (1H, d, J=5.48 Hz), 7.86 (1H, d, J=5.48 Hz), 7.51 (1H, d, J=5.48 Hz), 7.35-7.42 (1H, m), 7.27-7.33 (2H, m), 7.08-7.14 (1H, m), 6.83 (1H, d, J=5.12 Hz), 6.41 (1H, dd, J=3.68, 2.20 Hz), 5.30-5.35 (1H, m), 3.77 (1H, dd, J=12.44, 9.52 Hz), 3.61 (1H, dd, J=12.44, 5.12 Hz).

170. 3-(1H-Pyrrolo[2,3-b]pyridin-4-ylamino)-thiophene-2-carboxylic acid ((S)-2-amino-1-phenyl-ethyl)-amide

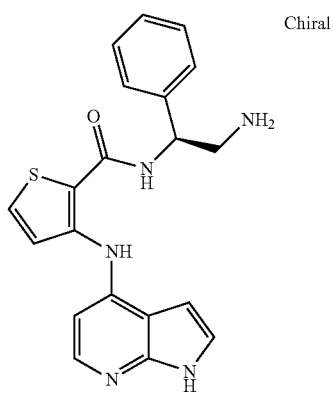 [SMILES: NC[C@@H](NC(=O)c1sccc1Nc1ccnc2[nH]ccc12)c1ccccc1]

A solution of 3-(1H-Pyrrolo[2,3-b]pyridin-4-ylamino)-thiophene-2-carboxylic acid ((S)-2-azido-1-phenyl-ethyl)-amide (130.00 mg; 0.32 mmol; 1.00 eq.) in methanol (50.00 ml) was subjected to hydrogenation with 10% palladium on carbon via H-Cube at 1 mL/min. After completion the solution was concentrated in vacuo. The crude was purified by Yamazen (basic condition, 0.1% NH4OH in Water/ACN) to afford the title compound as white solid in 66% yield. LCMS: m/e 378 (M+H). $^1$H NMR (DMSO-d$_6$): ppm 11.53 (1H, br. s.), 8.00 (1H, d, J=5.48 Hz), 7.82 (1H, d, J=5.12 Hz), 7.45 (1H, d, J=5.48 Hz), 7.26-7.33 (5H, m), 7.18-7.22 (1H, m), 6.75 (1H, d, J=5.52 Hz), 6.39 (1H, d, J=3.28 Hz), 4.96 (1H, dd, J=8.08, 5.52 Hz), 2.78-2.88 (2H, m).

IC$_{50}$ (p70S6K) "+++"

171. 3-(1H-Pyrrolo[2,3-b]pyridin-4-ylamino)-thiophene-2-carboxylic acid [(S)-2-amino-1-(3-fluoro-phenyl)-ethyl]-amide

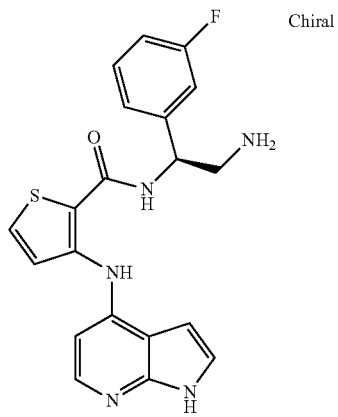 [SMILES: NC[C@@H](NC(=O)c1sccc1Nc1ccnc2[nH]ccc12)c1cccc(F)c1]

The title compound was prepared in an analogous manner as 3-(1H-Pyrrolo[2,3-b]pyridin-4-ylamino)-thiophene-2-carboxylic acid ((S)-2-amino-1-phenyl-ethyl)-amide in 65% yield. LCMS: m/e 396 (M+H) $^1$H NMR (DMSO-d 6) ppm 11.53 (1H, br. s.), 10.20 (1H, s), 8.00 (1H, d, J=5.48 Hz), 7.83 (1H, d, J=5.52 Hz), 7.46 (1H, d, J=5.48 Hz), 7.33 (1H, dd, J=14.32, 7.72 Hz), 7.28 (1H, d, J=2.50 Hz), 7.16 (1H, d, J=7.68 Hz), 7.01-7.06 (1H, m), 6.77 (1H, d, J=5.52 Hz), 6.39 (1H, d, J=3.68 Hz), 4.98 (1H, dd, J=7.68, 5.88 Hz), 2.78-2.88 (2H, m).

IC$_{50}$ (p70S6K) "+++"

3-(7H-Pyrrolo[2,3-d]pyrimidin-4-ylamino)-thiophene-2-carboxylic acid methyl ester (building block)

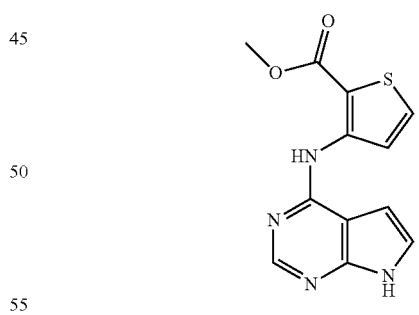

A suspension of 6-chloro-7-deazapurine (750 mg; 4.88 mmol), methyl 3-amino-2-thiophenecarboxylate (1.15 g; 7.33 mmol) and concentrated hydrochloric acid (410 µL; 4.9 mmol) in tert-butanol (15 mL) was microwaved at 75° C. for 3 h. The reaction mixture was diluted with methanol (15 mL) and filtered. The aqua solid was washed with methanol and dried under vacuo to afford the hydrochloric salt of 3-(7H-pyrrolo[2,3-d]pyrimidin-4-ylamino)-thiophene-2-carboxylic acid methyl ester (900 mg, 59%) as a green-gray solid (HPLC: 99%, RT: 6.50 min). $^1$H NMR (DMSO-d6) 12.47 (br s, 1H), 10.68 (br s, 1H), 8.44 (s, 1H), 8.08 (br s, 1H), 8.02 (d, J=5.5 Hz, 1H), 7.47 (dd, J=3.3, 2.2 Hz, 1H), 6.66 (br s, 1H), 3.83 (s, 3H); MS (m/z) 275 [M+H]$^+$.

172. 3-(7H-Pyrrolo[2,3-d]pyrimidin-4-ylamino)-thiophene-2-carboxylic acid benzylamide

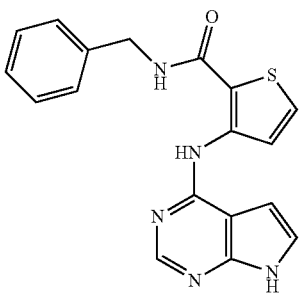 [SMILES: O=C(NCc1ccccc1)c1sccc1Nc1ncnc2[nH]ccc12]

To a solution of benzylamine (99 μl; 98 mg; 0.91 mmol) in anhydrous toluene (3 mL) placed in a sealed tube under nitrogen was added a solution of trimethylaluminum (365 μl; 2 M; 0.73 mmol) in toluene. The colorless solution was stirred at 25° C. for 1 h, before 3-(7H-pyrrolo[2,3-d]pyrimidin-4-ylamino)-thiophene-2-carboxylic acid methyl ester (50 mg; 0.18 mmol) was added and the resulting yellow suspension was heated to 105° C. overnight. The reaction mixture was allowed to cool down before water (0.1 mL) was added. The resulting blue suspension was stirred at 25° C. for 2 h, diluted with methanol and purified by chromatography on a SP1 Biotage system, using dichloromethane and methanol as eluents to afford 3-(7H-pyrrolo[2,3-d]pyrimidin-4-ylamino)-thiophene-2-carboxylic acid benzylamide (26 mg, 39%) as a gray solid (HPLC: 95%, RT: 6.04 min). $^1$H NMR (DMSO-d6) 11.96 (br s, 1H), 11.39 (s, 1H), 8.82 (t, J=5.9 Hz, 1H), 8.50 (d, J=5.1 Hz, 1H), 8.38 (s, 1H), 7.79 (d, J=5.5 Hz, 1H), 7.36-7.33 (m, 5H), 7.27-7.22 (m, 1H), 6.43 (dd, J=3.3, 1.8 Hz, 1H), 4.50 (d, J=5.9 Hz, 2H); MS (m/z) 350 [M+H]$^+$.

IC$_{50}$ (p70S6K) "+++"

173. 3-(7H-Pyrrolo[2,3-d]pyrimidin-4-ylamino)-thiophene-2-carboxylic acid 3-chloro-benzylamide

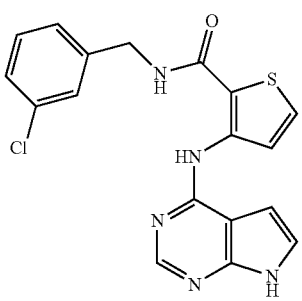 [SMILES: O=C(NCc1cccc(Cl)c1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using 3-chlorobenzylamine instead of benzylamine and obtained in 15% yield (HPLC: 94%, RT: 6.54 min). $^1$H NMR (DMSO-d6) 11.98 (br s, 1H), 11.33 (s, 1H), 8.61 (t, J=6.0 Hz, 1H), 8.50 (d, J=5.5 Hz, 1H), 8.39 (s, 1H), 7.81 (d, J=5.5 Hz, 1H), 7.41-7.29 (m, 5H), 6.43 (dd, J=3.7, 1.8 Hz, 1H), 4.50 (d, J=5.9 Hz, 2H); MS (m/z) 384 [M+H]$^+$ ($^{35}$Cl).

IC$_{50}$ (p70S6K) "+++"

174. 3-(7H-Pyrrolo[2,3-d]pyrimidin-4-ylamino)-thiophene-2-carboxylic acid phenethylamide

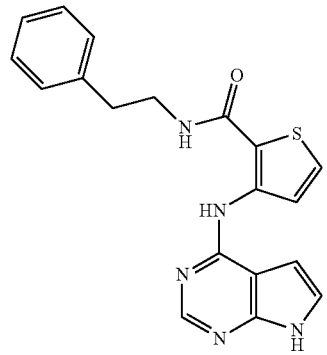 [SMILES: O=C(NCCc1ccccc1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using phenethylamine instead of benzylamine and obtained in 25% (HPLC: 90%, RT: 6.36 min). $^1$H NMR (DMSO-d6) 11.96 (br s, 1H), 11.38 (s, 1H), 8.47 (d, J=5.5 Hz, 1H), 8.38 (s, 1H), 8.32 (t, J=5.5 Hz, 1H), 7.75 (d, J=5.1 Hz, 1H), 7.36 (dd, J=3.7, 2.6 Hz, 1H), 7.33-7.18 (m, 5H), 6.46 (dd, J=3.7, 1.8 Hz, 1H), 3.54-3.47 (m, 2H), 2.87 (dd, J=8.1, 7.0 Hz, 2H); MS (m/z) 364 [M+H]$^+$.

IC$_{50}$ (p70S6K) "+++"

175. 3-(7H-Pyrrolo[2,3-d]pyrimidin-4-ylamino)-thiophene-2-carboxylic acid [2-(3-fluorophenyl)-ethyl]-amide

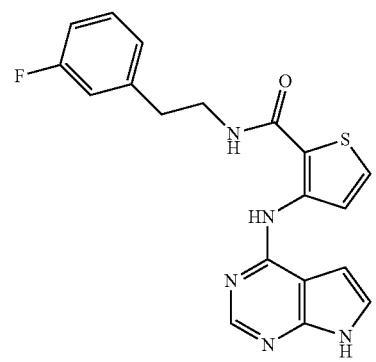 [SMILES: O=C(NCCc1cccc(F)c1)c1sccc1Nc1ncnc2[nH]ccc12]

To a solution of 3-fluorophenethylamine (130 μL; 134 mg; 0.97 mmol) in anhydrous toluene (3 mL) placed in a microwave tube under nitrogen was added a solution of trimethylaluminum (390 μL; 2.00 M; 0.77 mmol) in toluene. The colorless solution was stirred at 25° C. for 15 min, before 3-(7H-pyrrolo[2,3-d]pyrimidin-4-ylamino)-thiophene-2-carboxylic acid benzylamide (60 mg; 0.19 mmol), was added. The resulting green solution was stirred for 15 min under a flow of nitrogen, and microwaved to 120° C. for 30 min. The reaction mixture was allowed to cool down before water (0.1 mL) was added. The resulting beige suspension was stirred at 25° C. for 2 h, diluted with methanol and purified by chromatography on a SP1 Biotage system, using dichloromethane and methanol as eluents to afford 3-(7H-pyrrolo[2,3-d]pyrimidin-4-ylamino)-thiophene-2-carboxylic acid [2-(3-fluorophenyl)-ethyl]-amide (9 mg, 12%) as a white solid (HPLC: 98%, RT: 6.33 min). ¹H NMR (DMSO-d6) 11.97 (br s, 1H), 11.37 (s, 1H), 8.48 (d, J=5.5 Hz, 1H), 8.38 (s, 1H), 8.33 (t, J=5.5 Hz, 1H), 7.75 (d, J=5.5 Hz, 1H), 7.37 (dd, J=3.7, 2.6 Hz, 1H), 7.33 (t, J=7.7 Hz, 1H), 7.13-7.08 (m, 2H), 7.03 (td, J=8.1, 2.6 Hz, 1H), 6.45 (dd, J=3.7, 1.8 Hz, 1H), 3.53 (q, J=6.6 Hz, 2H), 2.90 (t, J=7.1 Hz, 2H); MS (m/z) 382 [M+H]⁺.

IC$_{50}$ (p70S6K) "+++"

3-(7H-Pyrrolo[2,3-d]pyrimidin-4-ylamino)-furan-2-carboxylic acid methyl ester (building block)

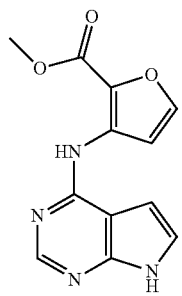 [SMILES: COC(=O)c1occc1Nc1ncnc2[nH]ccc12]

A suspension of 6-chloro-7-deazapurine (100.00 mg; 0.65 mmol), methyl 3-amino-2-furoate (138 mg; 0.98 mmol) and concentrated hydrochloric acid (55 µL; 0.65 mmol) in tert-butanol (2 mL) was microwaved at 75° C. for 3 h. The reaction mixture was diluted with methanol (2 mL) and purified by chromatography on a SP1 Biotage system, using dichloromethane and methanol as eluents to afford 3-(7H-pyrrolo[2,3-d]pyrimidin-4-ylamino)-furan-2-carboxylic acid methyl ester (30 mg, 18%) as a white solid. (HPLC: 99%, RT: 5.43 min). ¹H NMR (DMSO-d6) 12.03 (br s, 1H), 8.99 (br s, 1H), 8.40 (s, 1H), 7.90 (d, J=2.2 Hz, 1H), 7.71 (d, J=1.8 Hz, 1H), 7.38 (dd, J=3.3, 2.2 Hz, 1H), 6.60 (dd, J=3.3, 1.8 Hz, 1H), 3.90 (s, 3H); MS (m/z) 259 [M+H]⁺.

176. 3-(7H-Pyrrolo[2,3-d]pyrimidin-4-ylamino)-furan-2-carboxylic acid 3-chloro-benzylamide

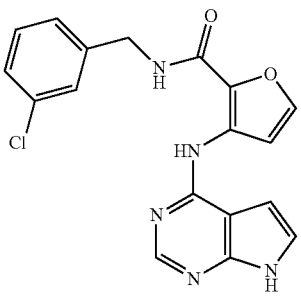 [SMILES: O=C(NCc1cccc(Cl)c1)c1occc1Nc1ncnc2[nH]ccc12]

The title compound was prepared in an analogous manner as 3-(7H-pyrrolo[2,3-d]pyrimidin-4-ylamino)-thiophene-2-carboxylic acid 3-chloro-benzylamide using 3-(7H-pyrrolo[2,3-d]pyrimidin-4-ylamino)-furan-2-carboxylic acid methyl ester instead of 3-(7H-pyrrolo[2,3-d]pyrimidin-4-ylamino)-thiophene-2-carboxylic acid methyl ester and obtained in 9% yield. ¹H NMR (DMSO-d6) 11.97 (br s, 1H), 9.67 (s, 1H), 9.01 (t, J=6.2 Hz, 1H), 8.38 (s, 1H), 7.83 (d, J=1.8 Hz, 1H), 7.73 (d, J=1.8 Hz, 1H), 7.41-7.30 (m, 5H), 6.45 (d, J=2.2 Hz, 1H), 4.49 (d, J=5.9 Hz, 2H); MS (m/z) 368 [M+H]⁺ (³⁵Cl).

IC$_{50}$ (p70S6K) "+++"

177. Benzyl-(2-{[3-(7H-pyrrolo[2,3-d]pyrimidin-4-ylamino)-furan-2-carbonyl]-amino}-ethyl)-carbamic acid tert-butyl ester)

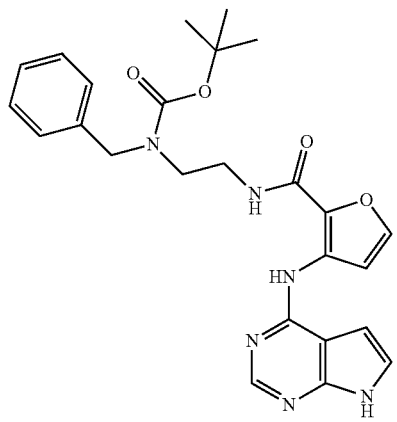 [SMILES: CC(C)(C)OC(=O)N(CCNC(=O)c1occc1Nc1ncnc2[nH]ccc12)Cc1ccccc1]

The title compound was prepared in an analogous manner as 3-(7H-pyrrolo[2,3-d]pyrimidin-4-ylamino)-furan-2-carboxylic acid 3-chloro-benzylamide using (2-aminoethyl)-benzyl carbamic acid tert-butyl ester instead of 3-chlorobenzylamine and obtained in 8% yield (HPLC: 90%, RT: 6.60 min). ¹H NMR (DMSO-d6) 11.99 (br s, 1H), 9.80 (br s, 1H), 8.44 (br s, 1H), 8.38 (s, 1H), 7.80 (br s, 1H), 7.71 (br s, 1H), 7.37 (dd, J=3.3, 2.6 Hz, 1H), 7.33 (d, J=7.3 Hz, 2H), 7.28-7.21 (m, 3H), 6.42 (br s, 1H), 4.44 (s, 2H), 3.40 (br s, 2H), 1.34 (s, 9H); MS (m/z) 477 [M+H]⁺.

IC$_{50}$ (p70S6K) "+"

5-Methyl-3-(7H-pyrrolo[2,3-d]pyrimidin-4-ylamino)-thiophene-2-carboxylic acid methyl ester (building block)

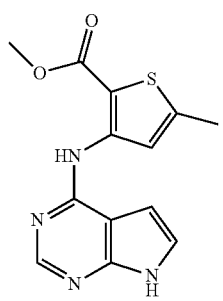

The title compound was prepared in an analogous manner as 3-(7H-pyrrolo[2,3-d]pyrimidin-4-ylamino)-thiophene-2-carboxylic acid methyl ester using methyl 3-amino-5-methylthiophene-2-carboxylate instead of methyl 3-amino-2-thiophenecarboxylate and obtained in 45% yield (HPLC: 99%, RT: 6.89 min). ¹H NMR (DMSO-d6) 12.40 (br s, 1H), 10.58 (br s, 1H), 8.44 (s, 1H), 7.96 (br s, 1H), 7.47 (dd, J=3.1, 2.6 Hz, 1H), 6.63 (dd, J=3.3, 1.5 Hz, 1H), 3.82 (s, 3H), 2.55 (s, 3H); MS (m/z) 289 [M+H]+.

178. 5-Methyl-3-(7H-pyrrolo[2,3-d]pyrimidin-4-ylamino)-thiophene-2-carboxylic acid 3-chloro-benzylamide

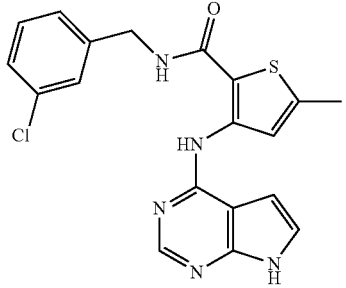 [SMILES: Cc1cc(Nc2ncnc3[nH]ccc23)c(C(=O)NCc2cccc(Cl)c2)s1]

The title compound was prepared in an analogous manner as 3-(7H-pyrrolo[2,3-d]pyrimidin-4-ylamino)-thiophene-2-carboxylic acid 3-chloro-benzylamide using 5-methyl-3-(7H-pyrrolo[2,3-d]pyrimidin-4-ylamino)-thiophene-2-carboxylic acid methyl ester instead of 3-(7H-pyrrolo[2,3-d]pyrimidin-4-ylamino)-thiophene-2-carboxylic acid methyl ester and obtained in 50% yield (HPLC: 98%, RT: 3.85 min). $^1$H NMR (DMSO-d6) 11.98 (br s, 1H), 11.39 (s, 1H), 8.68 (t, J=6.0 Hz, 1H), 8.39 (s, 1H), 8.28 (d, J=1.1 Hz, 1H), 7.40-7.28 (m, 5H), 6.41 (dd, J=3.3, 1.8 Hz, 1H), 4.48 (d, J=5.9 Hz, 2H), 2.55 (s, 3H); MS (m/z) 398 [M+H]+ ($^{35}$Cl).

IC$_{50}$ (p70S6K) "++"

179. 3-(7H-Pyrrolo[2,3-d]pyrimidin-4-ylamino)-thiophene-2-carboxylic acid [2-(4-fluoro-phenyl)-ethyl]-amide

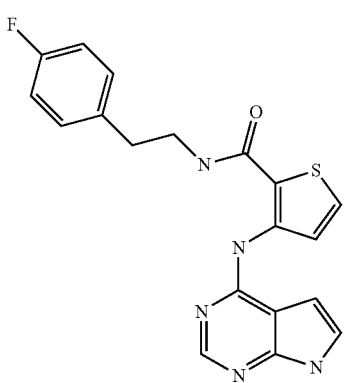 [SMILES: O=C(NCCc1ccc(F)cc1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using 4-fluorophenethylamine instead of benzylamine and obtained in 14% yield (HPLC: 92%, RT: 6.36 min). $^1$H NMR (DMSO-d6) 11.97 (br s, 1H), 11.37 (s, 1H), 8.47 (d, J=5.4 Hz, 1H), 8.38 (s, 1H), 8.31 (t, J=5.7 Hz, 1H), 7.75 (d, J=5.4 Hz, 1H), 7.37 (dd, J=3.4, 2.4 Hz, 1H), 7.32-7.26 (m, 2H), 7.16-7.08 (m, 2H), 6.45 (dd, J=3.6, 1.9 Hz, 1H), 3.49 (dd, J=14.3, 6.4 Hz, 2H), 2.86 (t, J=7.6 Hz, 2H); MS (m/z) 382 [M+H]+.

IC$_{50}$ (p70S6K) "+++"

180. 3-(7H-Pyrrolo[2,3-d]pyrimidin-4-ylamino)-thiophene-2-carboxylic acid [2-(4-bromo-phenyl)-ethyl]-amide

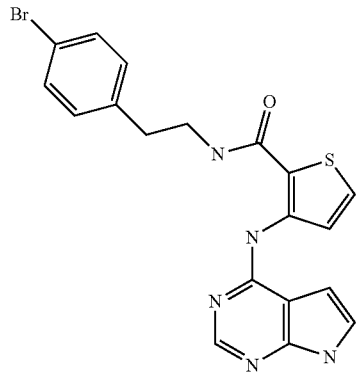 [SMILES: O=C(NCCc1ccc(Br)cc1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using 4-bromophenethylamine instead of benzylamine and obtained in 20% yield (HPLC: 60%, RT: 6.81 min). $^1$H NMR (DMSO-d6) 11.98 (br s, 1H), 11.37 (s, 1H), 8.47 (d, J=5.5 Hz, 1H), 8.38 (s, 1H), 8.32 (t, J=5.5 Hz, 1H), 7.75 (d, J=5.1 Hz, 1H), 7.50-7.47 (m, 2H), 7.37 (dd, J=3.3, 2.2 Hz, 1H), 7.25-7.21 (m, 2H), 6.45 (dd, J=3.6, 1.8 Hz, 1H), 3.54-3.47 (m, 2H), 2.85 (t, J=7.0 Hz, 2H); MS (m/z) 442 [M+H]+.

IC$_{50}$ (p70S6K) "+++"

181. 3-(7H-Pyrrolo[2,3-d]pyrimidin-4-ylamino)-thiophene-2-carboxylic acid (2-o-tolyl-ethyl)-amide

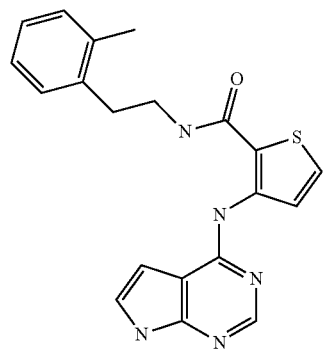 [SMILES: Cc1ccccc1CCNC(=O)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using 2-methylphenethylamine instead of benzylamine and obtained in 39% yield (HPLC: 95%, RT: 6.67 min). $^1$H NMR (DMSO-d6) 11.98 (br s, 1H), 11.43 (s, 1H), 8.48 (d, J=5.5 Hz, 1H), 8.42-8.36 (m, 2H), 7.76 (d, J=5.5 Hz, 1H), 7.37 (dd, J=3.3, 2.2 Hz, 1H), 7.18-7.10 (m, 4H), 6.46 (dd, J=3.7, 1.8 Hz, 1H), 3.47-3.43 (m, 2H), 2.86 (t, J=7.9 Hz, 2H), 2.36 (s, 3H); MS (m/z) 378 [M+H]+.

IC$_{50}$ (p70S6K) "+++"

182. 3-(7H-Pyrrolo[2,3-d]pyrimidin-4-ylamino)-thiophene-2-carboxylic acid [2-(3-chloro-phenyl)-ethyl]-amide

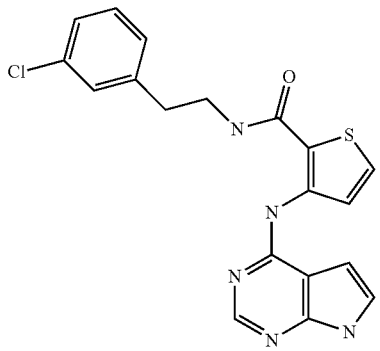 [SMILES: O=C(NCCc1cccc(Cl)c1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using 3-chlorophenethylamine instead of benzylamine and obtained in 32% yield. $^1$H NMR (DMSO-d6) 11.98 (br s, 1H), 11.37 (s, 1H), 8.48 (d, J=5.5 Hz, 1H), 8.38 (s, 1H), 8.33 (t, J=5.5 Hz, 1H), 7.76 (d, J=5.5 Hz, 1H), 7.38-7.23 (m, 5H), 6.45 (dd, J=3.3, 1.8 Hz, 1H), 3.55-3.50 (m, 2H), 2.89 (t, J=7.5 Hz, 2H); MS (m/z) 398 [M+H]$^+$.

IC$_{50}$ (p70S6K) "+++"

183. 3-(7H-Pyrrolo[2,3-d]pyrimidin-4-ylamino)-thiophene-2-carboxylic acid (2-benzylamino-ethyl)-amide

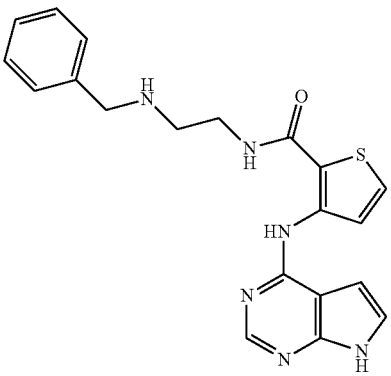 [SMILES: O=C(NCCNCc1ccccc1)c1sccc1Nc1ncnc2[nH]ccc12]

The title compound was prepared in an analogous manner as 3-(7H-pyrrolo[2,3-d]pyrimidin-4-ylamino)-thiophene-2-carboxylic acid benzylamide using N-benzylethane-1,2-diamine instead of benzylamine and obtained in 61% yield. $^1$H NMR (DMSO-d6) 11.96 (br s, 1H), 11.41 (s, 1H), 8.46 (d, J=5.5 Hz, 1H), 8.38 (s, 1H), 8.19-8.14 (m, 1H), 7.75 (d, J=5.5 Hz, 1H), 7.38-7.18 (m, 7H), 6.46-6.43 (m, 1H), 3.73 (s, 2H) 3.37 (dd, J=12.4, 6.6 Hz, 2H), 2.89 (t, J=6.6 Hz, 2H); MS (m/z) 393 [M+H]$^+$.

IC$_{50}$ (p70S6K) "+++"

184. 3-{[3-(7H-Pyrrolo[2,3-d]pyrimidin-4-ylamino)-thiophene-2-carbonyl]-amino}-piperidine-1-carboxylic acid tert-butyl ester

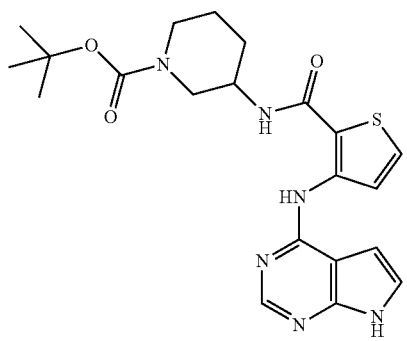 [SMILES: CC(C)(C)OC(=O)N1CCCC(NC(=O)c2sccc2Nc2ncnc3[nH]ccc23)C1]

The title compound was prepared in an analogous manner as 3-(7H-pyrrolo[2,3-d]pyrimidin-4-ylamino)-thiophene-2-carboxylic acid benzylamide using tert-butyl 3-aminopiperidine-1-carboxylate instead of benzylamine and obtained in 14% yield. $^1$H NMR (DMSO-d6) 11.96 (br s, 1H), 11.39 (br s, 1H), 8.47 (d, J=5.8 Hz, 1H), 8.38 (s, 1H), 8.09-8.01 (m, 1H), 7.78 (d, J=4.8 Hz, 1H), 7.38-7.14 (m, 1H), 6.48-6.43 (m, 1H), 3.91-3.75 (m, 3H), 2.80-2.62 (m, 3H), 1.92-1.84 (m, 1H), 1.75-1.66 (m, 1H), 1.65-1.54 (m, 1H), 1.40 (s, 9H); MS (m/z) 443 [M+H]$^+$.

IC$_{50}$ (p70S6K) "++"

185. 3-(7H-Pyrrolo[2,3-d]pyrimidin-4-ylamino)-thiophene-2-carboxylic acid (2-methylamino-ethyl)-amide

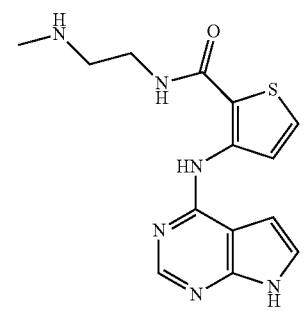 [SMILES: CNCCNC(=O)c1sccc1Nc1ncnc2[nH]ccc12]

To a solution of tert-butyl (2-aminoethyl)(methyl)carbamate (158 μl; 154 mg; 0.88 mmol) in anhydrous toluene (3 mL) placed in a sealed tube under nitrogen was added a solution of trimethylaluminum (354 μl; 2 M; 0.71 mmol) in toluene. The colorless solution was stirred at 25° C. for 1 h, before 3-(7H-pyrrolo[2,3-d]pyrimidin-4-ylamino)-thiophene-2-carboxylic acid methyl ester (55 mg; 0.18 mmol) was added and the resulting yellow suspension was heated to 105° C. overnight. The reaction mixture was allowed to cool down before water (0.1 mL) was added. The resulting gray suspension was stirred at 25° C. for 2 h, diluted with methanol and purified by chromatography on a SP1 Biotage system, using hexane and ethyl acetate as eluents to afford crude tert-butyl methyl[2-({[3-(7H-pyrrolo[2,3-d]pyrimidin-4-ylamino)-2-thienyl]

carbonyl}amino)ethyl]carbamate as a white solid. The solid was suspended in methanol (1 mL) in a 5 mL flask with magnetic stir bar. To the white suspension was added hydrochloric acid (0.21 mL, 2.0N in diethyl ether, 0.42 mmol). The resulting solution was stirred at 25° C. overnight and the resulting precipitate was collected by filtration. The precipitate was purified using preparative HPLC to afford 3-(7H-Pyrrolo[2,3-d]pyrimidin-4-ylamino)-thiophene-2-carboxylic acid (2-methylamino-ethyl)-amide (1 mg, 2%) as a brown solid. $^1$H NMR (MeOH-d4) 8.55 (d, J=5.5 Hz, 1H), 8.40 (s, 1H), 7.66 (d, J=5.2 Hz, 1H), 7.29 (d, J=3.7 Hz, 1H), 6.61 (d, J=3.3 Hz, 1H), 3.73-3.67 (m, 2H), 3.34-3.28 (m, 2H), 2.75 (s, 3H); MS (m/z) 317 [M+H]$^+$.

IC$_{50}$ (p70S6K) "++"

186. 3-(7H-Pyrrolo[2,3-d]pyrimidin-4-ylamino)-thiophene-2-carboxylic acid piperidin-3-ylamide

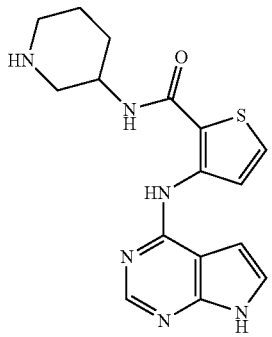 [SMILES: O=C(NC1CCCNC1)c1sccc1Nc1ncnc2[nH]ccc12]

To a 20 mL flask with magnetic stir bar was added 3-{[3-(7H-Pyrrolo[2,3-d]pyrimidin-4-ylamino)-thiophene-2-carbonyl]-amino}-piperidine-1-carboxylic acid tert-butyl ester (100 mg, 0.23 mmol) in dichloromethane (2 mL). To the stirred solution was added trifluoroacetic acid (2.0 mL, 26.0 mmol) and the solution was stirred at 25° C. for 1 h. The solution was concentrated on a rotary evaporator and purified by preparative HPLC to afford 3-(7H-Pyrrolo[2,3-d]pyrimidin-4-ylamino)-thiophene-2-carboxylic acid piperidin-3-ylamide as a yellow solid (14 mg, 13%) (HPLC: 99%, RT: 2.81 min). $^1$H NMR (DMSO-d6) 12.02 (br s, 1H), 11.30 (s, 1H), 8.68-8.52 (m, 1H), 8.47 (d, J=5.5 Hz, 1H), 8.40 (s, 1H), 8.23 (d, J=7.7 Hz, 1H), 7.82 (d, J=5.5 Hz, 1H), 7.38 (dd, J=3.3, 2.2 Hz, 1H), 6.43 (dd, J=3.6, 1.8 Hz, 1H), 4.31-4.18 (m, 1H), 3.40-3.17 (m, 2H), 2.89-2.77 (m, 2H), 1.96-1.85 (m, 2H), 1.74-1.60 (m, 2H); MS (m/z) 343 [M+H]$^+$.

IC$_{50}$ (p70S6K) "+++"

187. 3-(5-Methyl-7H-pyrrolo[2,3-d]pyrimidin-4-ylamino)-thiophene-2-carboxylic acid 3-chloro-benzylamide

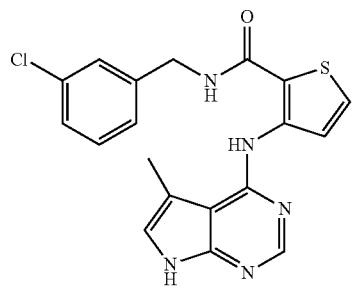 [SMILES: Cc1c[nH]c2ncnc(Nc3ccsc3C(=O)NCc3cccc(Cl)c3)c12]

Trimethyl aluminum (0.35 mL, 0.69 mmol, 2M in toluene) was added to a solution of 3-(5-methyl-7H-pyrrolo[2,3-d]pyrimidin-4-ylamino)-thiophene-2-carboxylic acid methyl ester (50 mg, 0.17 mmol) and 3-chlorobenzylamine (0.11 mL, 0.87 mmol) in toluene (2 mL), and stirred overnight at 70° C. The reaction mixture was cooled to room temperature, diluted with H$_2$O and EtOAC, and filtered through an Extrelut column. The column was washed with EtOAC and the filtrate was concentrated. The crude product was purified via Biotage eluting with a gradient of 0 to 100% EtOAC in hexanes to provide the desire product (34 mg, 49% yield) as an off-white solid. LC-MS (M+H=398, obsd.=398).

IC$_{50}$ (p70S6K) "+++"

Biological Activity p70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 µM ATP in an assay buffer containing 100 mM Hepes (pH 7.5), 5 mM MgCl2, 1 mM DTT, 0.015% Brij and 1 µM of the substrate peptide FITC-AHA-AKRRRLSS-LRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analysed on a Caliper Life Sciences Lab Chip 3000, using a pressure of −1.4 psi, and upstream and downstream voltages of −3000 and −700 respectively. Product peaks are resolved before substrate peaks on the resulting chromatograms.

To assess the inhibitory potential of the compounds, IC50-values were determined, as shown in Table 1 above.

The invention claimed is:

1. A compound of Formula (I):

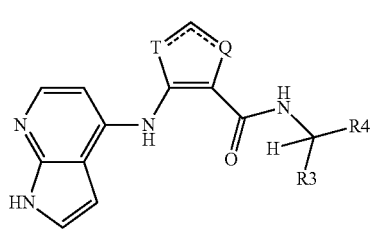

(I)

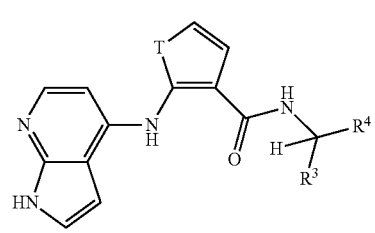

(II)

and pharmaceutically acceptable salts, thereof,
wherein:
T, Q are S or CH, with the proviso that if T is S, Q is CH, and if Q is S, T is CH,
----- denotes the presence or absence of a bond, with the proviso that one of the two dashed lines is always a bond, whereas the other one is always absent,
$R^3$ is H or A,
$R^4$ is A or Ar, or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is (fluoro-benzoylamino)-benzyl, (benzoylamino)-benzyl, (chloro-azabenzoylamino)-benzyl, (thiophenylmethyl)amino-ethyl, (indolylmethyl)amino-methyl, (1-phenyl-ethylamino)-methyl, benzyloxy-methyl, phenylamino-methyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, benzoylamino-methyl, 1-hydroxy-1-phenyl-methyl, (furanylmethylsulfanyl)-methyl or benzenesulfonylamino-methyl,
$R^3$ and $R^4$ together with the C atom to which they are attached, may form Ar, or cyclic A which may be unsubstituted or substituted by COO(LA) or CONH(LA),
Ar is a mono- or bicyclic aromatic homo- or heterocycle having 1 to 4 N, O and/or S atoms and 5 to 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, CONH(LAr), $CONA_2$, NHCOA, NHCO(LAr), NHCONHA, $NHCONH_2$, $NHSO_2A$, CHO, COA, $SO_2NH_2$, $SO_2A$ and/or $SO_2Hal$,
A is unbranched or branched, linear or cyclic alkyl having 1, 2, 3, 4, 5, 6, 7 or 8 C atoms, in which one or two $CH_2$ groups may be replaced by an O or S atom and/or by an NH, N(LA), $SO_2$, CONH, NHCO or —CH═CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$, $N_3$, $NO_2$ or CN,
LA is unbranched or branched, linear alkyl having 1, 2, 3 or 4 C atoms,
LAr is a monocyclic aromatic homo- or heterocycle having 1 or 2 N, O and/or S atoms and 5 to 7 skeleton atoms, which may be unsubstituted or mono-, di- or trisubstituted by Hal, LA, OH, O(LA), $NH_2$ or NH(LA),
Hal is F, Cl, Br or I.
2. The compounds according to claim 1 which conforms to Formulae (II):

and pharmaceutically acceptable salts, thereof,
in which T is S, and the remaining substituents have the meaning indicated for Formula (I) according to claim 1.
3. The compounds according to claim 1 which conform to Formulae (IV):

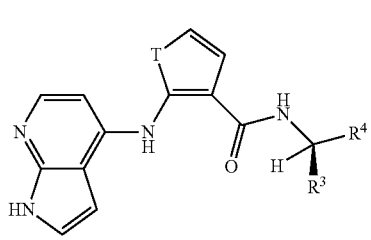

(IV)

and pharmaceutically acceptable salts, solvates or prodrugs thereof, in which T is S, and the remaining substituents have the meaning indicated for Formula (I) according to claim 1.
4. The compounds according to claim 2, in which the residues not designated in greater detail have the meaning indicated for the Formula (I) according to claim 1, but in which:
in Subformula A
T is S,
in Subformula F
T is S,
$R^3$ is H, hydroxymethyl, aminomethyl, azidomethyl or cyanomethyl,
in Subformula G
T is S,
$R^4$ is phenyl or benzyl, which may be unsubstituted or, independently of one another, mono-, di- or trisubstituted by methyl, methoxy, $CF_3$, $OCF_3$, amino, Cl or F; or
$R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or
$R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl,
in Subformula N
T is S,
$R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, in Subformula T T is S, $R^3$ is hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F, in Subformula U T is S, $R^3$ is H, $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, in Subformula V T is S, $R^3$ and $R^4$ together with the C atom to which they are attached, form piperidinyl, phenyl, pyrrolidinyl, tetrahydrofuranyl, each of which may be unsubstituted or, independently of one another, mono-, di- or trisubstituted by methyl, methoxy, $CF_3$, $OCF_3$, amino, Cl or F, in Subformula W T is S, $R^3$ is H, and the remaining residues have the meaning as indicated for Formula (I), and pharmaceutically acceptable salts, thereof.

5. The compounds according to claim 3, in which the residues not designated in greater detail have the meaning indicated for the Formula (I) according to claim 1, but in which:

in Subformula A

T is S, in Subformula F

T is S, $R^3$ is H, hydroxymethyl, aminomethyl, azidomethyl or cyanomethyl, in Subformula G T is S, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, in Subformula N T is S, $R^3$ is H, hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F; or $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, in Subformula T T is S, $R^3$ is hydroxymethyl, aminomethyl, azidomethyl or cyanomethyl, $R^4$ is phenyl or benzyl, which may be unsubstituted or, independently of one another, mono-, di- or trisubstituted by methyl, methoxy, $CF_3$, $OCF_3$, amino, Cl or F, in Subformula U T is S, $R^3$ is H, $R^4$ is benzylamino-methyl, wherein the phenyl ring may be unsubstituted or, independently of one another, mono-, di- or trisubstituted by methyl, methoxy, $CF_3$, $OCF_3$, amino, Cl or F; or $R^4$ is aminomethyl, (fluoro-benzoylamino)-benzyl, (benzoylamino)-benzyl, (chloro-azabenzoylamino)-benzyl, pyrrolidinyl, (thiophenylmethyl)amino-ethyl, (indolylmethyl)amino-methyl, (1-phenyl-ethylamino)-methyl, benzyloxy-methyl, phenylamino-methyl, isobutyl, (bis-furan-3-ylmethyl-amino)-methyl, [furanylmethyl)amino]methyl, [pyrrolylmethyl)amino]methyl, thiophenyl-methyl, (sulfamoyl-phenyl)-methyl, cyclohexenyl-methyl, benzoylamino-methyl, 1-hydroxy-1-phenyl-methyl, (furanylmethylsulfanyl)-methyl or benzenesulfonylamino-methyl, in Subformula V T is S, R³ and R⁴ together with the C atom to which they are attached, form piperidinyl, phenyl, pyrrolidinyl, tetrahydrofuranyl, each of which may be unsubstituted or, independently of one another, mono-, di- or trisubstituted by methyl, methoxy, CF₃, OCF₃, amino, Cl or F, in Subformula W T is S, R³ is H, and the remaining residues have the meaning as indicated for Formula (I), and pharmaceutically acceptable salts, thereof.

6. The compound according to claim 1, wherein the compound is selected from the group consisting of:

3-(7H-Pyrrolo[2,3-d]pyrimidin-4-ylamino)-thiophene-2-carboxylic acid [2-(3-fluoro-phenyl)-ethyl]amide, 3-(7H-Pyrrolo[2,3-d]pyrimidin-4-ylamino)-thiophene-2-carboxylic acid phenethyl-amide, 3-(7H-Pyrrolo[2,3-d]pyrimidin-4-ylamino)-thiophene-2-carboxylic acid [2-(3-chloro-phenyl)-ethyl]-amide, 3-(7H-Pyrrolo[2,3-d]pyrimidin-4-ylamino)-thiophene-2-carboxylic acid [2-(4-fluoro-phenyl)-ethyl]amide, 3-(7H-Pyrrolo[2,3-d]pyrimidin-4-ylamino)-thiophene-2-carboxylic acid [2-(4-bromo-phenyl)-ethyl]-amide, 3-(7H-Pyrrolo[2,3-d]pyrimidin-4-ylamino)-thiophene-2-carboxylic acid (2-o-tolyl-ethyl)-amide, 3-(7H-Pyrrolo[2,3-d]pyrimidin-4-ylamino)-thiophene-2-carboxylic acid (2-benzylamino-ethyl)-amide, 3-(1H-Pyrrolo[2,3-b]pyridin-4-ylamino)-thiophene-2-carboxylic acid (2-benzylamino-ethyl)-amide, 3-(1H-Pyrrolo[2,3-b]pyridin-4-ylamino)-thiophene-2-carboxylic acid [2-(4-fluoro-phenyl)-ethyl]amide, 3-(7H-Pyrrolo[2,3-d]pyrimidin-4-ylamino)-thiophene-2-carboxylic acid piperidin-3-ylamide, 3-(1H-Pyrrolo[2,3-b]pyridin-4-ylamino)-thiophene-2-carboxylic acid pyrrolidin-3-ylamide, 3-(1H-Pyrrolo[2,3-b]pyridin-4-ylamino)-thiophene-2-carboxylic acid (2-cyclohex-1-enyl-ethyl)-amide, 3-(1H-Pyrrolo[2,3-b]pyridin-4-ylamino)-thiophene-2-carboxylic acid [2-(4-sulfamoyl-phenyl)-ethyl]-amide, 3-(1H-Pyrrolo[2,3-b]pyridin-4-ylamino)-thiophene-2-carboxylic acid [2-(3-trifluoromethyl-phenyl)-ethyl]-amide, 3-(1H-Pyrrolo[2,3-b]pyridin-4-ylamino)-thiophene-2-carboxylic acid [2-(3-chloro-phenyl)-ethyl]amide, 3-(1H-Pyrrolo[2,3-b]pyridin-4-ylamino)-thiophene-2-carboxylic acid (2-thiophen-2-yl-ethyl)-amide, 3-(1H-Pyrrolo[2,3-b]pyridin-4-ylamino)-thiophene-2-carboxylic acid [2-(3-fluoro-phenyl)-ethyl]-amide, 3-(1H-Pyrrolo[2,3-b]pyridin-4-ylamino)-thiophene-2-carboxylic acid [2-(4-fluoro-phenyl)-ethyl]-amide, 3-(1H-Pyrrolo[2,3-b]pyridin-4-ylamino)-thiophene-2-carboxylic acid [2-(furan-2-ylmethylsulfanyl)-ethyl]-amide, 3-(1H-Pyrrolo[2,3-b]pyridin-4-ylamino)-thiophene-2-carboxylic acid (2-o-tolyl-ethyl)-amide, 3-(1H-Pyrrolo[2,3-b]pyridin-4-ylamino)-thiophene-2-carboxylic acid [2-(3-methoxy-phenyl)-ethyl]amide, 3-(1H-Pyrrolo[2,3-b]pyridin-4-ylamino)-thiophene-2-carboxylic acid [2-(4-bromo-phenyl)-ethyl]-amide, 3-(1H-Pyrrolo[2,3-b]pyridin-4-ylamino)-thiophene-2-carboxylic acid [2-(4-methoxy-phenyl)-ethyl]amide, 3-(1H-Pyrrolo[2,3-b]pyridin-4-ylamino)-thiophene-2-carboxylic acid (2-benzylamino-ethyl)-amide, 3-(1H-Pyrrolo[2,3-b]pyridin-4-ylamino)-thiophene-2-carboxylic acid 3-chloro-benzylamide, 3-(1H-Pyrrolo[2,3-b]pyridin-4-ylamino)-thiophene-2-carboxylic acid (2-phenylamino-ethyl)-amide, 3-(1H-Pyrrolo[2,3-b]pyridin-4-ylamino)-thiophene-2-carboxylic acid (4-chloro-phenyl)-amide, 3-(1H-Pyrrolo[2,3-b]pyridin-4-ylamino)-thiophene-2-carboxylic acid (4-methoxy-phenyl)-amide, 3-(1H-Pyrrolo[2,3-b]pyridin-4-ylamino)-thiophene-2-carboxylic acid (4-fluoro-phenyl)-amide, 3-(1H-Pyrrolo[2,3-b]pyridin-4-ylamino)-thiophene-2-carboxylic acid [2-(4-methoxy-benzylamino)-ethyl]-amide, 3-(1H-Pyrrolo[2,3-b]pyridin-4-ylamino)-thiophene-2-carboxylic acid {2-[(pyridin-2-ylmethyl)-amino]-ethyl}-amide, 3-(1H-Pyrrolo[2,3-b]pyridin-4-ylamino)-thiophene-2-carboxylic acid (2-amino-ethyl)-amide, S-[3-(1H-Pyrrolo[2,3-b]pyridin-4-ylamino)-thiophene-2-carboxylic acid (2-hydroxy-1-phenyl-ethyl)-amide], 3-(1H-Pyrrolo[2,3-b]pyridin-4-ylamino)-thiophene-2-carboxylic acid {2-[(thiophen-3-ylmethyl)-amino]-ethyl}-amide, 3-(1H-Pyrrolo[2,3-b]pyridin-4-ylamino)-thiophene-2-carboxylic acid [2-(bis-furan-3-ylmethyl-amino)-ethyl]-amide, 3-(1H-Pyrrolo[2,3-b]pyridin-4-ylamino)-thiophene-2-carboxylic acid [2-(2-trifluoromethoxy-benzylamino)-ethyl]-amide, 3-(1H-Pyrrolo[2,3-b]pyridin-4-ylamino)-thiophene-2-carboxylic acid [2-(3-methoxy-benzylamino)-ethyl]-amide, 3-(1H-Pyrrolo[2,3-b]pyridin-4-ylamino)-thiophene-2-carboxylic acid [2-(3-trifluoromethoxy-benzylamino)-ethyl]-amide, 3-(1H-Pyrrolo[2,3-b]pyridin-4-ylamino)-thiophene-2-carboxylic acid [2-(4-trifluoromethoxy-benzylamino)-ethyl]-amide, 3-(1H-Pyrrolo[2,3-b]pyridin-4-ylamino)-thiophene-2-carboxylic acid [2-(4-trifluoromethyl-benzylamino)-ethyl]-amide, 3-(1H-Pyrrolo[2,3-b]pyridin-4-ylamino)-thiophene-2-carboxylic acid {2-[(furan-3-ylmethyl)-amino]-ethyl}-amide, 3-(1H-Pyrrolo[2,3-b]pyridin-4-ylamino)-thiophene-2-carboxylic acid {2-[(1H-pyrrol-2-ylmethyl)-amino]-ethyl}-amide, 3-(1H-Pyrrolo[2,3-b]pyridin-4-ylamino)-thiophene-2-carboxylic acid [2-(3-methyl-benzylamino)-ethyl]-amide, 3-(1H-Pyrrolo[2,3-b]pyridin-4-ylamino)-thiophene-2-carboxylic acid [2-(3-chloro-benzylamino)-ethyl]-amide, 3-(1H-Pyrrolo[2,3-b]pyridin-4-ylamino)-thiophene-2-carboxylic acid [2-(2-fluoro-benzylamino)-ethyl]-amide, 3-(1H-Pyrrolo[2,3-b]pyridin-4-ylamino)-thiophene-2-carboxylic acid {2-[(1H-indol-5-ylmethyl)-amino]-ethyl}-amide, 3-(1H-Pyrrolo[2,3-b]pyridin-4-ylamino)-thiophene-2-carboxylic acid [2-(2-methoxy-benzylamino)-ethyl]-amide, 3-(1H-Pyrrolo[2,3-b]pyridin-4-ylamino)-thiophene-2-carboxylic acid [2-(4-fluoro-benzylamino)-ethyl]-amide, 3-(1H-Pyrrolo[2,3-b]pyridin-4-ylamino)-thiophene-2-carboxylic acid [2-(3-chloro-4-fluoro-benzylamino)-ethyl]-amide, 3-(1H-Pyrrolo[2,3-b]pyridin-4-ylamino)-thiophene-2-carboxylic acid (2-benzyloxy-ethyl)-amide,
3-(1H-Pyrrolo[2,3-b]pyridin-4-ylamino)-thiophene-2-carboxylic acid (2-benzoylamino-ethyl)-amide,
2-(1H-Pyrrolo[2,3-b]pyridin-4-ylamino)-thiophene-3-carboxylic acid (2-benzylamino-ethyl)-amide,
2-(1H-Pyrrolo[2,3-b]pyridin-4-ylamino)-thiophene-3-carboxylic acid ((S)-2-hydroxy-1-phenyl-ethyl)-amide,
3-(1H-Pyrrolo[2,3-b]pyridin-4-ylamino)-thiophene-2-carboxylic acid (2-azido-1-phenyl-ethyl)-amide,
3-(1H-Pyrrolo[2,3-b]pyridin-4-ylamino)-thiophene-2-carboxylic acid (2-amino-1-phenyl-ethyl)-amide,
3-(1H-Pyrrolo[2,3-b]pyridin-4-ylamino)-thiophene-2-carboxylic acid (2-amino-2-phenyl-ethyl)-amide,
3-(1H-Pyrrolo[2,3-b]pyridin-4-ylamino)-thiophene-2-carboxylic acid ((S)-1-benzyl-2-hydroxy-ethyl)-amide,
3-(1H-Pyrrolo[2,3-b]pyridin-4-ylamino)-thiophene-2-carboxylic acid 3-amino-benzylamide,
3-(1H-Pyrrolo[2,3-b]pyridin-4-ylamino)-thiophene-2-carboxylic acid [2-(4-chloro-3-trifluoromethyl-benzylamino)-ethyl]-amide,
3-(1H-Pyrrolo[2,3-b]pyridin-4-ylamino)-thiophene-2-carboxylic acid 3-methoxybenzylamide,
3-(1H-Pyrrolo[2,3-b]pyridin-4-ylamino)-thiophene-2-carboxylic acid 4-chloro-3-trifluoromethyl-benzylamide,
3-(1H-Pyrrolo[2,3-b]pyridin-4-ylamino)-thiophene-2-carboxylic acid (2-hydroxy-2-phenyl-ethyl)-amide,
3-(1H-Pyrrolo[2,3-b]pyridin-4-ylamino)-thiophene-2-carboxylic acid 3-(4-fluoro-benzoylamino)-benzylamide,
2-(1H-Pyrrolo[2,3-b]pyridin-4-ylamino)-thiophene-3-carboxylic acid pyrrolidin-3-ylamide,
2-(1H-Pyrrolo[2,3-b]pyridin-4-ylamino)-thiophene-3-carboxylic acid piperidin-3-ylamide,
3-(1H-Pyrrolo[2,3-b]pyridin-4-ylamino)-thiophene-2-carboxylic acid [2-amino-1-(3-fluoro-phenyl)-ethyl]-amide,
3-(1H-Pyrrolo[2,3-b]pyridin-4-ylamino)-thiophene-2-carboxylic acid [2-amino-1-(2-methoxy-phenyl)-ethyl]-amide,
2-(1H-Pyrrolo[2,3-b]pyridin-4-ylamino)-thiophene-3-carboxylic acid [2-amino-1-(3-fluoro-phenyl)-ethyl]-amide,
2-(1H-Pyrrolo[2,3-b]pyridin-4-ylamino)-thiophene-3-carboxylic acid [2-amino-1-(2-methoxy-phenyl)-ethyl]-amide,
2-(1H-Pyrrolo[2,3-b]pyridin-4-ylamino)-thiophene-3-carboxylic acid [2-amino-1-(3,4-dimethoxy-phenyl)-ethyl]-amide,
2-(1H-Pyrrolo[2,3-b]pyridin-4-ylamino)-thiophene-3-carboxylic acid 3-amino-benzylamide,
2-(1H-Pyrrolo[2,3-b]pyridin-4-ylamino)-thiophene-3-carboxylic acid benzylamide 3-(1H-Pyrrolo[2,3-b]pyridin-4-ylamino)-thiophene-2-carboxylic acid [2-amino-1-(3,4-dimethoxy-phenyl)-ethyl]-amide, 2-(1H-Pyrrolo[2,3-b]pyridin-4-ylamino)-thiophene-3-carboxylic acid ((S)-2-azido-1-phenyl-ethyl)-amide,
3-(1H-Pyrrolo[2,3-b]pyridin-4-ylamino)-thiophene-2-carboxylic acid ((R)-2-cyano-1-phenyl-ethyl)-amide,
2-(1H-Pyrrolo[2,3-b]pyridin-4-ylamino)-thiophene-3-carboxylic acid (cyano-phenyl-methyl)-amide,
2-(1H-Pyrrolo[2,3-b]pyridin-4-ylamino)-thiophene-3-carboxylic acid ((S)-1-hydroxymethyl-3-methyl-butyl)-amide,
2-(1H-Pyrrolo[2,3-b]pyridin-4-ylamino)-thiophene-3-carboxylic acid ((S)-1-hydroxymethyl-2-phenyl-ethyl)-amide,
3-(1H-Pyrrolo[2,3-b]pyridin-4-ylamino)-thiophene-2-carboxylic acid ((R)-2-carbamoyl-1-phenyl-ethyl)-amide,
2-(1H-Pyrrolo[2,3-b]pyridin-4-ylamino)-thiophene-3-carboxylic acid 3-chloro-4-trifluoromethyl-benzylamide,
3-(1H-Pyrrolo[2,3-b]pyridin-4-ylamino)-thiophene-2-carboxylic acid (2-amino-1-p-tolyl-ethyl)-amide,
3-(1H-Pyrrolo[2,3-b]pyridin-4-ylamino)-thiophene-2-carboxylic acid [2-amino-1-(3-methoxy-phenyl)-ethyl]-amide,
3-(1H-Pyrrolo[2,3-b]pyridin-4-ylamino)-thiophene-2-carboxylic acid [2-amino-1-(3-chloro-phenyl)-ethyl]-amide,
3-(1H-Pyrrolo[2,3-b]pyridin-4-ylamino)-thiophene-2-carboxylic acid [2-amino-1-(3,4-dichloro-phenyl)-ethyl]-amide,
2-(1H-Pyrrolo[2,3-b]pyridin-4-ylamino)-thiophene-3-carboxylic acid (2-amino-1-p-tolyl-ethyl)-amide,
2-(1H-Pyrrolo[2,3-b]pyridin-4-ylamino)-thiophene-3-carboxylic acid [2-amino-1-(3-methoxy-phenyl)-ethyl]-amide,
2-(1H-Pyrrolo[2,3-b]pyridin-4-ylamino)-thiophene-3-carboxylic acid [2-amino-1-(3,4-dichloro-phenyl)-ethyl]-amide,
2-Chloro-N-[3-({[3-(1H-pyrrolo[2,3-b]pyridin-4-ylamino)-thiophene-2-carbonyl]-amino}-methyl)-phenyl]-isonicotinamide,
2-(1H-Pyrrolo[2,3-b]pyridin-4-ylamino)-thiophene-3-carboxylic acid [2-amino-1-(3-chloro-phenyl)-ethyl]-amide,
3-(1H-Pyrrolo[2,3-b]pyridin-4-ylamino)-thiophene-2-carboxylic acid [2-(1-phenyl-ethylamino)-ethyl]-amide,
3-(1H-Pyrrolo[2,3-b]pyridin-4-ylamino)-thiophene-2-carboxylic acid [2-amino-1-(4-trifluoromethyl-phenyl)-ethyl]-amide,
2-(1H-Pyrrolo[2,3-b]pyridin-4-ylamino)-thiophene-3-carboxylic acid [2-amino-1-(4-trifluoromethyl-phenyl)-ethyl]-amide,
(S)-[3-(1H-Pyrrolo[2,3-b]pyridin-4-ylamino)-thiophene-2-carboxylic acid[2-(1,3-dioxo-1,3-dihydro-isoindol-2-yl)-1-phenyl-ethyl]-amide],
(S)-2-(1H-Pyrrolo[2,3-b]pyridin-4-ylamino)-thiophene-3-carboxylic acid[2-(1,3-dioxo-1,3-dihydro-isoindol-2-yl)-1-phenyl-ethyl]-amide,
3-(1H-Pyrrolo[2,3-b]pyridin-4-ylamino)-thiophene-2-carboxylic acid [2-(4-methyl-benzylamino)-ethyl]-amide,
3-(1H-Pyrrolo[2,3-b]pyridin-4-ylamino)-thiophene-2-carboxylic acid [2-(3-chloro-4-methoxy-benzylamino)-ethyl]-amide,
2-(1H-Pyrrolo[2,3-b]pyridin-4-ylamino)-thiophene-3-carboxylic acid ((R)-2-cyano-1-phenyl-ethyl)-amide,
2-(1H-Pyrrolo[2,3-b]pyridin-4-ylamino)-thiophene-3-carboxylic acid ((S)-2-amino-1-phenyl-ethyl)-amide,
2-Pyrrolidin-1-yl-N-[3-({[3-(1H-pyrrolo[2,3-b]pyridin-4-ylamino)-thiophene-2-carbonyl]-amino}-methyl)-phenyl]-isonicotinamide,
2-Dimethylamino-N-[3-({[3-(1H-pyrrolo[2,3-b]pyridin-4-ylamino)-thiophene-2-carbonyl]-amino}-methyl)-phenyl]-isonicotinamide, 2-(4-Methyl-piperazin-1-yl)-N-[3-({[3-(1H-pyrrolo[2,3-b]pyridin-4-ylamino)-thiophene-2-carbonyl]-amino}-methyl)-phenyl]-isonicotinamide, 3-(1H-Pyrrolo[2,3-b]pyridin-4-ylamino)-thiophene-2-carboxylic acid [1-(3-fluoro-phenyl)-2-methylamino-ethyl]-amide, 3-(1H-Pyrrolo[2,3-b]pyridin-4-ylamino)-thiophene-2-carboxylic acid [1-(3-chloro-phenyl)-2-methylamino-ethyl]-amide, 3-(1H-Pyrrolo[2,3-b]pyridin-4-ylamino)-thiophene-2-carboxylic acid (2-methylamino-1-phenyl-ethyl)-amide, 3-(1H-Pyrrolo[2,3-b]pyridin-4-ylamino)-thiophene-2-carboxylic acid ((S)-2-amino-1-phenyl-ethyl)-amide, 3-(1H-Pyrrolo[2,3-b]pyridin-4-ylamino)-thiophene-2-carboxylic acid [(S)-2-amino-1-(3-fluoro-phenyl)-ethyl]-amide, 3-(7H-Pyrrolo[2,3-d]pyrimidin-4-ylamino)-thiophene-2-carboxylic acid benzylamide, 3-(7H-Pyrrolo[2,3-d]pyrimidin-4-ylamino)-thiophene-2-carboxylic acid [2-(3-fluorophenyl)-ethyl]-amide, 3-(7H-Pyrrolo[2,3-d]pyrimidin-4-ylamino)-thiophene-2-carboxylic acid [2-(3-chloro-phenyl)-ethyl]-amide, 3-(5-Methyl-7H-pyrrolo[2,3-d]pyrimidin-4-ylamino)-thiophene-2-carboxylic acid 3-chloro-benzylamide and pharmaceutically acceptable salts, thereof.

7. A pharmaceutical composition comprising a compound according to claim 1, or a pharmaceutically acceptable salt, thereof, as active ingredient, together with a pharmaceutically acceptable carrier.

8. A pharmaceutical composition comprising a compound according to claim 6, or a pharmaceutically acceptable salt, thereof, as active ingredient, together with a pharmaceutically acceptable carrier.

9. Set (kit) consisting of separate packs of:
a) an effective amount of a compound according to claim 1 or a pharmaceutically acceptable salt, thereof, and
b) an effective amount of a further medicament active ingredient.

10. Set (kit) consisting of separate packs of:
a) an effective amount of a compound according to claim 6 or a pharmaceutically acceptable salt, thereof, and
b) an effective amount of a further medicament active ingredient.

* * * * *